US011078502B2

(12) United States Patent
Mookerjee et al.

(10) Patent No.: US 11,078,502 B2
(45) Date of Patent: Aug. 3, 2021

(54) METHOD AND CELL LINE FOR PRODUCTION OF POLYKETIDES IN YEAST

(71) Applicant: Hyasynth Biologicals Inc., Montreal (CA)

(72) Inventors: Shoham Mookerjee, Montreal (CA); Alexander James Campbell, Montreal (CA); Zachary Douglas Wiltshire, Montreal (CA); Kevin John Chen, Montreal (CA)

(73) Assignee: Hyasynth Biologicals Inc., Montreal (CA)

( * ) Notice: Subject to any disclaimer, the term of this patent is extended or adjusted under 35 U.S.C. 154(b) by 0 days.

(21) Appl. No.: 16/486,618

(22) PCT Filed: Feb. 19, 2018

(86) PCT No.: PCT/CA2018/050190

§ 371 (c)(1),
(2) Date: Aug. 16, 2019

(87) PCT Pub. No.: WO2018/148849

PCT Pub. Date: Aug. 23, 2018

(65) Prior Publication Data

US 2019/0367953 A1 Dec. 5, 2019

Related U.S. Application Data

(60) Provisional application No. 62/460,526, filed on Feb. 17, 2017.

(51) Int. Cl.

| | |
|---|---|
| ***C12N 1/15*** | (2006.01) |
| ***C12N 15/54*** | (2006.01) |
| ***C12N 9/10*** | (2006.01) |
| ***C12P 7/22*** | (2006.01) |
| ***C07K 14/395*** | (2006.01) |
| ***C12N 9/04*** | (2006.01) |
| ***C12N 9/12*** | (2006.01) |
| ***C12N 9/00*** | (2006.01) |
| ***C12N 15/52*** | (2006.01) |

(52) U.S. Cl.

CPC .............. *C12P 7/22* (2013.01); *C07K 14/395* (2013.01); *C12N 9/0006* (2013.01); *C12N 9/1029* (2013.01); *C12N 9/1085* (2013.01); *C12N 9/1288* (2013.01); *C12N 9/93* (2013.01); *C12N 15/52* (2013.01); *C12Y 205/01041* (2013.01); *C12Y 101/01001* (2013.01); *C12Y 203/01* (2013.01); *C12Y 207/08007* (2013.01); *C12Y 602/01001* (2013.01)

(58) Field of Classification Search

None

See application file for complete search history.

(56) References Cited

U.S. PATENT DOCUMENTS

| | | | |
|---|---|---|---|
| 7,361,482 | B2 | 4/2008 | Chang et al. |
| 7,361,483 | B2 | 4/2008 | Kuzuyama et al. |
| 8,124,390 | B2 | 2/2012 | Kuzuyama et al. |
| 8,884,100 | B2 | 11/2014 | Page et al. |
| 9,359,625 | B2 | 6/2016 | Winnicki et al. |
| 9,394,510 | B2 | 7/2016 | Peet et al. |
| 9,670,494 | B2 | 6/2017 | Nielsen et al. |
| 9,765,308 | B2 | 9/2017 | Page et al. |
| 2008/0020438 | A1 | 1/2008 | Matsuda et al. |
| 2012/0122180 | A1 | 5/2012 | Austin et al. |
| 2013/0197248 | A1 | 8/2013 | Nielsen et al. |
| 2014/0141476 | A1 | 5/2014 | Page et al. |
| 2014/0330032 | A1 | 11/2014 | Lynch et al. |
| 2016/0010126 | A1 | 1/2016 | Poulos et al. |
| 2016/0138056 | A1 | 5/2016 | Jensen et al. |

FOREIGN PATENT DOCUMENTS

| | | | |
|---|---|---|---|
| EP | 1338603 | A2 | 8/2003 |
| WO | 03072602 | A2 | 9/2003 |
| WO | 2006060839 | A2 | 6/2006 |
| WO | 2006081537 | A2 | 8/2006 |
| WO | 2011127589 | A1 | 10/2011 |
| WO | 2012017083 | A1 | 2/2012 |
| WO | 2013006953 | A1 | 1/2013 |
| WO | 2014018982 | A1 | 1/2014 |
| WO | 2014207113 | A1 | 12/2014 |
| WO | 2015032911 | A1 | 3/2015 |

(Continued)

OTHER PUBLICATIONS

AB164375 Nucleic Acid Sequence, NCBI [online database], Sequence Deposited Mar. 28, 2008 (Mar. 28, 2008), Retrieved from the internet: [URL: https://www.ncbi.nlm.nih.gov/nuccore/AB164375].

Austin et al., "Biosynthesis of Dictyostelium Discoideum Differentiation-Inducing Factor by a Hybild Type I Fatty Acid-Type III Polyketide Synthase," Nature Chemical Biology, Sep. 2006, vol. 2 (9), pp. 494-502.

(Continued)

*Primary Examiner* — Rebecca E Prouty

(74) *Attorney, Agent, or Firm* — Fish & Richardson P.C.

(57) ABSTRACT

A method and cell line for producing polyketides in yeast. The method applies, and the cell line includes, a yeast cell transformed with a polyketide synthase coding sequence. The polyketide synthase enzyme catalyzes synthesis of olivetol or methyl-olivetol, and may include *Dictyostelium discoideum* polyketide synthase ("DiPKS"). Wild type DiPKS produces methyl-olivetol only. DiPKS may be modified to produce olivetol only or a mixture of both olivetol and methyl-olivetol. The yeast cell may be modified to include a phosphopantethienyl transferase for increased activity of DiPKS. The yeast cell may be modified to mitigate mitochondrial acetaldehyde catabolism for increasing malonyl-CoA available for synthesizing olivetol or methyl-olivetol.

40 Claims, 7 Drawing Sheets

Specification includes a Sequence Listing.

(56) References Cited

FOREIGN PATENT DOCUMENTS

| | | | |
|---|---|---|---|
| WO | 2016010827 | A1 | 1/2016 |
| WO | 2016159869 | A1 | 10/2016 |
| WO | 2017139496 | A1 | 8/2017 |
| WO | 2017161041 | A1 | 9/2017 |
| WO | 2018200888 | A1 | 11/2018 |

OTHER PUBLICATIONS

Baba et al., "Yeast Coq5 C-Methyltransferase is Required for Stability of Other Polypeptides Involved in Coenzyme Q Biosynthesis," The Journal of Biological Chemistry, Mar. 2004, vol. 279 (11), pp. 10052-10059.

Bonitz et al., "Evolutionary Relationships of Microbial homatic Prenyltransferases," PLoS One, Nov. 2011, vol. 6 (11), pp. e27336.

Carvalho et al., "Designing Microorganisms for Heterologous Biosynthesis of Cannabinoids," FEMS Yeast Research, Jun. 2017, vol. 17 (4), pp. 1-11, ISSN 1567-1356.

Chambon et al., "Isolation and Properties of Yeast mutants Affected in Farnesyl Diphosphate Synthetase," Current Genetics, Jul. 1990, vol. 18 (1), pp. 41-46.

Cheon et al., "A Biosynthetic Pathway for Hexanoic Add Production in Kluyveromyces Marxianus," Journal of Biotechnology, Jul. 2014, vol. 182-183, pp. 30-36.

Degenhardt et al., "Chapter 2. The Biosynthesis of Cannabinoids" Dec. 2017, pp. 13-23.

Fellermeier et al., "Biosynthesis of Cannabinoids. Incorporation Experiments With (13)C-Labeled Glucoses," European Journal of Biochemistry, Mar. 2001, vol. 268 (6), pp. 1596-1604.

Fellermeier, "Prenylation of Olivetolate by a Hemp Transferase Yields Cannabigerolic Add, the Precursor of Tetrahydrocannabinol," FEBS Letters, May 1998, vol. 427 (2), pp. 283-285.

Fischer et al., "Metabolic Engineering of Monoterpene Synthesis in Yeast," Biotechnology and Bioengineering, vol. 108 (8), pp. 1883-1892.

Flagfeldt et al., "Characterization of Chromosomal Integration Sites for Heterologous Gene Expression in *Saccharomyces cerevisiae*," Yeast, Oct. 2009, vol. 26 (10), pp. 545-551.

Flemming et al., "Chemistry and Biological Activity of Tetrahydrocannabinol and its Derivatives," Topics in Heterocyclic Chamistry, Bioactive Heterocycles IV, Aug. 2007, vol. 10, pp. 1-42.

Gagne et al., "Identification of Otivablio Acid Cyclase From Cannabis Sativa Reveals a Unique Catalytic Route to Plant Polyketides," Proceedings of the National Academy of Sciences of the United States of America, Jul. 2012, vol. 109 (31), pp. 12811-12816.

Gagne., "The Polyketide Origins of Cannabinoids in Cannabis Saliva," A Thesis Submitted to the College of Graduate Studies and Research in Partial Fulfillment of the Requirements for the Degree of Doctor of Philosophy in the Department of Biology, University of Saskatchewan, 2013, 263 pages.

Ghosh et al., "Dissecting the Functional Role of Polyketide Synthases in Dictyostelium Discoideum: Biosynthesis of the Differentiation Regulating Factor 4-methyl-5-pentylbenzene-1,3-diol," The Journal of Biological Chemistry, Apr. 2008, vol. 283 (17), pp. 11348-11354, ISSN 0021-9258.

Gietz et al., "High-Efficiency Yeast Transformation Using the LiAc/SS Carrier DNA/PEG Method," Nature Protocols, 2007, vol. 2 (1), pp. 31-34.

Gietz et al., "Yeast Transformation by the LiAc/SS Carrier DNA/PEG Method," Methods in Molecular Biology, 2014, vol. 1205. https://doi.org/10.1007/978-1-4939-1363-3_1.

Huang et al., "Effect of Organic Acids on the Growth and Lipid Accumulation of Oleagincus Yeast Trichosporon Fermentans," Biotechnology for Biofuels, Jan. 2012, vol. 5 (1), pp. 4.

Hunkova et al., "Toxic Effects of Fatty Acids on Yeast Cells: Dependence of Inhibitory Effects on Fatty Acid Concentration," Biotechnology and Bioengineering, Nov. 1977, vol. 19 (11), pp. 1623-1641.

International Patent Application No. PCT/CA2018/050190, International Search Report and Written Opinion dated May 31, 2018.

International Patent Appllcation No. PCT/CA2018/50190, International Preliminary Report on Patentability dated Jul. 5, 2019.

Jensen et al., "EasyClone: Method for Iterative Chromosomal Integration of Multiple Genes in *Saccharomyces cerevisiae*," FEMS Yeast Research, Mar. 2014, vol. 14(2), pp. 238-248. https://doi.org/10.1111/1567-1364.12118.

Kaminska et al., "The Isoprenoid Biosynthetic Pathway in *Saccharomyces cerevisiae* is Affected in a maf1-1 Mutant With Altered tRNA Synthesis" FEMS Yeast Rearch, Mar. 2002, vol. 2 (1), pp. 31-37.

Kim et al., "Characterization of NpgA, A 4'-Phosphopantetheinyl Transferase of Aspergillus Nidulans, and Evidence of Its Involvement in Fungal Growth and Formation of Conidia and Cleistothecia for Development" Journal of Microbiology, Jan. 2015, vol. 53 (1), pp. 21-31.

Krivoruchko et al., "Microbial Acetyl-CoA Metabolism and Metabolic Engineering," Metabolic Engineenng, Mar. 2015, vol. 28, pp. 28-42.

Kuzuyama, et al., "Structural Basis for the Promiscuous Biosynthetic Prenylation of Aromatic Natural Products," Nature, Jun. 2005, vol. 435 (7044), pp. 983-987.

Liu et al., "Overproduction of Geraniol by Enhanced Precursor Supply in *Saccharomyres cerevisiae*," Journal of Biotechnology, Dec. 2013, vol. 168 (4), pp. 446-451.

NCBI GenBank online database under Accession No. NC 007087.3, Jan. 2010.

NCBI GenBank online database under accession No. NCBI AB187169, Oct. 2015.

Oswald et al., "Monoterpenoid Biosysnthesis in *Saccharomyces cerevisiae*," FEMS Yeast Research, May 2007, vol. 7(3), pp. 413-421. https://doi.org/10.1111/j.1567-1364.2006.00172.x.

Pamplaniyil, "Identification, Isolation and Functional Characterization of Prenyltransferases in *Cannabis saliva* L.," Faculty of Biochemical and Chemical Engineering, The Technical University of Dortmund, Dissertation, 2016, 139 pages.

Razdan, "Structure-Activty Relabonships in Cannabinoids," Pharmacological Reviews, Jun. 1986, vol. 38 (2), pp. 75-149.

Ro et al., "Production of the Antimalarial Drug Precursor Artemisinic Acid in Engineered Yeast," Nature Letters, Apr. 2006, vol. 440(7086), pp. 940-943.

Ryan et al., "CRISPR-Cas9 Genorne Engineering in *Saccharomyces cerevisiae* Cells," CAD Spring Harbor Protocols, Jun. 2016, vol. 2016(6). https://doi.org/10.1101/pdb.prot086827.

Schreckenbach., "Enzymatische Oligomerisierung von Alkendiphosphaten," Martin Luther University Halle—Wittenberg, Dissertation, 2017, 159 pages.

Shi et al., "Improving Production of Malonyl Coenzyme A-Derived Metabolites by Abolishing Snf1-Dependent Regulation of Acc1" American Society for Microbiology, May 2014, vol. 5 (3), pp. e01130-14.

Shiba et al., "Engineering of the Pyruvate Dehydrogenase Bypass in *Saccharomyces cerevisiae* for High-Level Production of Isoprenoids," Metabolic Engineering, Mar. 2007, vol. 9 (2), pp. 160-168.

Skiba et al., "Domain Organization and Active Site Architecture of a Polyketide Synthase C-Methyltransferase," ACS Chemical Biology, Dec. 2016, vol. 11 (12), pp. 3319-3327.

Stout et al., "The Hexanoyl-CoA Precursor for Cannabinoid Biosysnthesis if Formed by an Acyl-activating Enzyme in Cannabis Sativa Trichomes," The Plant Journal, Aug. 2012, vol. 71 (3), pp. 353-365.

Suguyama et al., "Metabolic Engineering for the Production of Prenylated Polyphenols in Transgenic Legume Plants Using Bacterial and Plant Prenyltransferases," Metabolic Engineering, Nov. 2011, vol. 13 (6), pp. 629-637.

Taura et al., "Characterization of Olivetol Synthase, A Polyketide Synthase Putatively Involved in Cannabinoid Biosynthetic Pathway," FEBS Letters, Jun. 2009, vol. 583 (12), pp. 2061-2066, ISSN 0014-5793.

Taura et al., "First Direct Evidence for the Mechanism of .DELTA. 1-tetrahydrocannabinoilic Acid Biosynthesis," Journal of the American Chemical Society, Sep. 1995, vol. 117, pp. 9766-9767.

(56) References Cited

OTHER PUBLICATIONS

Tello et al., "The ABBA Family of Aromatic Prenyltransferase: Broadening Natural Product Devesity," Cellular and Molecular Life Sciences, May 2008, vol. 64 (10), pp. 1459-1463.
Viegas et al., "Inhibition of Yeast Growth by Octanoic and Decanoic Acids Produced during Ethanolic Fermentation," Applied and Environmental Microbiology, Jan. 1989, vol. 55 (1), pp. 21-28.
Zirpel et al., "Engineering Yeasts as Platform Organisms for Cannabinoid Biosynthesis," Journal of Biotechnology, Oct. 2017, vol. 259, pp. 204-212, ISSN 0168-1656.
Zirpel et al., "Production of DELTA 9-Tetrahydrocannabinolic Acid From Cannabigerolic Acid by Whole Cells of Pichia (Komagataella) Pastoris Expressing DELTA 9-Tetrahydrocannabinolic Add Synthase From *Cannabis sativa* L," Biotechnology letters, Sep. 2015, vol. 37 (9), pp. 1869-1875.
Taura et al., "Characterization of Olivetol Synthase, a Polyketide Synthase Putatively Involved in Cannabinoid Biosynthetic Pathway," FEBS Letters 583 (2009) 2061-2066, (available online on May 19, 2009).
European Patent Application No. 18754640.3, Supplementary European Search Report dated Nov. 30, 2020.
Hanus et al.. "Phytocannabinoids: A Unified Critical Inventory," Natural Product Reports, Nov. 23, 2016, vol. 33 (12), pp. 1357-1392.
Singapore Patent Application No. SG11201907459Y, Search Report and Written opinion dated Nov. 30, 2020.
Stehle et al., "Biotechnological Synthesis of Tetrahydrocannabinolic Acid Heterologe Biosynthese Der Tetrahydrocannabinolsäure," Pharmakon, Mar. 2017, vol. 5(2). pp. 142-147.
Zucko et al., "Polyketide Synthase Genes and the Natural Products Potential of Dictyostelium Discoideum," Bioinformatics, 2007, vol. 23(19), pp. 2543-2549.

KS | AT | DH | C-MET | ER | KR | ACP | TYPE III
Fig. 7
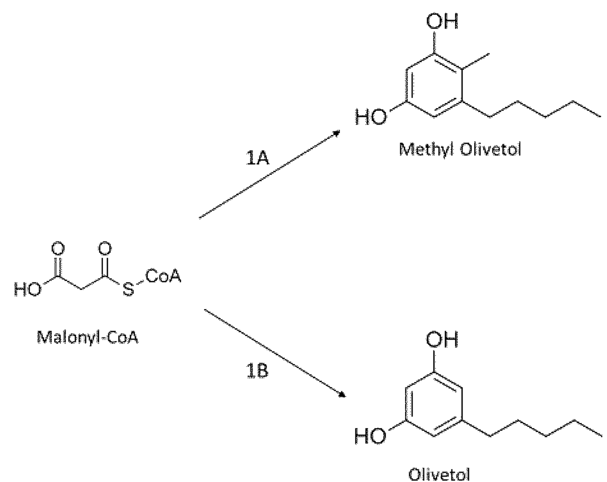
Fig. 8
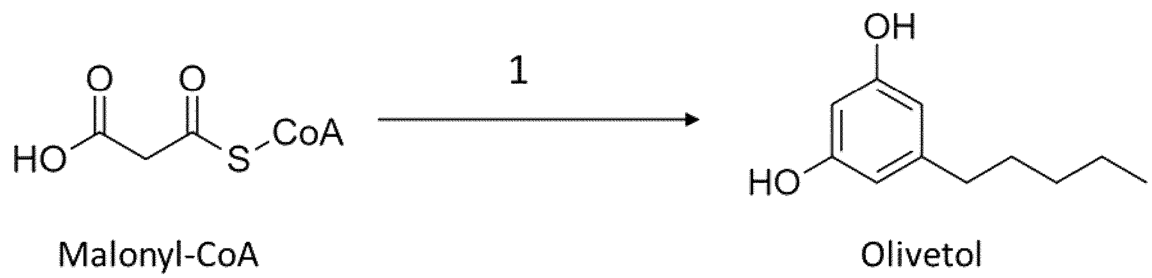
Fig. 9

METHOD AND CELL LINE FOR PRODUCTION OF POLYKETIDES IN YEAST

CROSS REFERENCE TO RELATED APPLICATIONS

This application is a 371 national stage filing of international application PCT/CA2018/050190, filed Feb. 19, 2018, which claims the benefit of priority of U.S. Provisional Patent Application No. 62/460,526, entitled METHOD AND CELL LINE FOR PRODUCTION OF PHYTOCANNABINOIDS IN YEAST, filed Feb. 17, 2017, which is hereby incorporated by reference in its entirety.

FIELD

The present disclosure relates generally to production of polyketides in yeast.

BACKGROUND

Polyketides are precursors to many valuable secondary metabolites in plants. For example, phytocannabinoids, which are naturally produced in *Cannabis sativa*, other plants, and some fungi, have significant commercial value. Over 105 phytocannabinoids are known to be biosynthesized in *C. sativa*, or result from thermal or other decomposition from phytocannabinoids biosynthesized in *C. sativa*. While the *C. sativa* plant is also a valuable source of grain, fiber, and other material, growing *C. sativa* for phytocannabinoid production, particularly indoors, is costly in terms of energy and labour. Subsequent extraction, purification, and fractionation of phytocannabinoids from the *C. sativa* plant is also labour and energy intensive.

Phytocannabinoids are pharmacologically active molecules that contribute to the medical and psychotropic effects of *C. sativa*. Biosynthesis of phytocannabinoids in the *C. sativa* plant scales similarly to other agricultural projects. As with other agricultural projects, large scale production of phytocannabinoids by growing *C. sativa* requires a variety of inputs (e.g. nutrients, light, pest control, $CO_2$, etc.). The inputs required for cultivating *C. sativa* must be provided. In addition, cultivation of *C. sativa*, where allowed, is currently subject to heavy regulation, taxes, and rigorous quality control where products prepared from the plant are for commercial use, further increasing costs. Phytocannabinoid analogues are pharmacologically active molecules that are structurally similar to phytocannabinoids. Phytocannabinoid analogues are often synthesized chemically, which can be labour intensive and costly. As a result, it may be economical to produce the phytocannabinoids and phytocannabinoid analogues in a robust and scalable, fermentable organism. *Saccharomyces cerevisiae* is an example of a fermentable organism that has been used to produce industrial scales of similar molecules.

The time, energy, and labour involved in growing *C. sativa* for production of naturally-occurring phytocannabinoids provides a motivation to produce transgenic cell lines for production of phytocannabinoids by other means. Polyketides, including olivetolic acid and its analogues are valuable precursors to phytocannabinoids.

SUMMARY

It is an object of the present disclosure to obviate or mitigate at least one disadvantage of previous approaches to producing phytocannabinoids outside of the *C. sativa* plant, and of previous approaches to producing phytocannabinoid analogues. Many of the 105 phytocannabinoids found in *Cannabis sativa* may be biosynthesized from olivetolic acid or olivetol. Phytocannabinoids and their analogues may also be chemically synthesized from olivetol and other reagents. Olivetol and olivetolic acid may also be used in pharmaceutical or nutritional product development as well. As a consequence it may be desirable to improve yeast-based production of olivetol, olivetolic acid or analogues of either olivetol or olivetolic acid. Similarly, an approach that allows for production of phytocannabinoid analogues without the need for labour-intensive synthesis may be desirable.

The methods and cells lines provided herein may apply and include *Saccharomyces cerevisiae* that has been transformed to include a gene for *Dictyostelium discoideum* polyketide synthase ("DiPKS"). DiPKS is a fusion protein consisting of both a type I fatty acid synthase ("FAS") and a polyketide synthase ("PKS") and is referred to as a hybrid "FAS-PKS" protein. DiPKS catalyzes synthesis of methyl-olivetol from malonyl-CoA. The reaction has a 6:1 stoichiometric ratio of malonyl-CoA to methyl-olivetol. Downstream prenyltransferase enzymes catalyzes synthesis of methyl cannabigerol ("meCBG") from methyl-olivetol and geranyl pyrophosphate ("GPP"), similarly to synthesis of cannabigerolic acid ("CBGa") from olivetolic acid and GPP. Hexanoic acid is toxic to *S. cerevisiae*. Hexanoyl-CoA is a precursor for synthesis of olivetol by *Cannabis Sativa* olivetolic acid synthase ("OAS"). As a result, when using DiPKS rather than OAS, hexanoic acid need not be added to the growth media, which may result in increased growth of the *S. cerevisiae* cultures and greater yield of meCBG compared with yields of CBG when using OAS. In addition, in *C. sativa*, the olivetol is carboxylated in the presence of olivetolic acid cyclase ("OAC") or another polyketide cyclase into olivetolic acid, which feeds into the CBGa synthesis metabolic pathway, beginning with prenylation of olivetolic acid catalyzed by in *C. sativa* by a membrane-bound prenyltransferase. The option to produce olivetol or methyl-olivetol rather than olivetolic acid may facilitate preparation of decarboxylated species of phytocannabinoids and methylated analogues of phytocannabinoids.

For some applications, meCBG and methylated downstream phytocannabinoid analogues that can be synthesized from meCBG (similarly to downstream phytocannabinoids being synthesized from CBGa in *C. sativa*) may be valuable. In other cases, phytocannabinoids structurally identical to the decarboxylated forms of naturally-occurring phytocannabinoids may be more desirable. For production of phytocannabinoids that are structurally identical to the decarboxylated forms of naturally-occurring phytocannabinoids, DiPKS may be modified relative to wild type DiPKS to reduce methylation of olivetol, resulting in synthesis of either both olivetol and methyl-olivetol Synthesis of olivetol and methyl-olivetol may be facilitated by increased levels of malonyl-CoA in the cytosol. The *S. cerevisiae* may have overexpression of native acetaldehyde dehydrogenase and expression of a mutant acetyl-CoA synthase or other gene, the mutations resulting in lowered mitochondrial acetaldehyde catabolism. Lowering mitochondrial acetaldehyde catabolism by diverting the acetaldehyde into acetyl-CoA production increases malonyl-CoA available for synthesizing olivetol. Acc1 is the native yeast malonyl CoA synthase. The *S. cerevisiae* may have overexpression of Acc1 or modification of Acc1 for increased activity and increase available malonyl-CoA. The *S. cerevisiae* may include modified expression of Maf1 or other regulators of tRNA biosynthesis. Overexpressing native Maf1 has been shown to reduce loss of isopentyl pyrophosphate ("IPP") to tRNA biosynthesis and thereby improve monoterpene yields in yeast. IPP is an intermediate in the mevalonate pathway. Upc2 is an activator for sterol biosynthesis in *S. cerevisiae*, and a Glu888Asp mutation of Upc2 may increase monoterpene production in yeast. The *S. cerevisiae* may include a co-factor loading enzyme to increase the activity of DiPKS. Other species of yeast, including *Yarrowia lipolytica, Kluyveromyces marxianus, Kluyveromyces lactis, Rhodosporidium toruloides, Cryptococcus curvatus, Trichosporon pullulan* and *Lipomyces lipoferetc*, may be applied.

In a first aspect, herein provided is a method and cell line for producing polyketides in yeast. The method applies, and the cell line includes, a yeast cell transformed with a polyketide synthase coding sequence. The polyketide synthase enzyme catalyzes synthesis of olivetol or methyl-olivetol, and may include *Dictyostelium discoideum* polyketide synthase ("DiPKS"). Wild type DiPKS produces methyl-olivetol only. DiPKS may be modified to produce olivetol only or a mixture of both olivetol and methyl-olivetol. The yeast cell may be modified to include a phosphopantetheinyl transferase for increased activity of DiPKS. The yeast cell may be modified to mitigate mitochondrial acetaldehyde catabolism for increasing malonyl-CoA available for synthesizing olivetol or methyl-olivetol.

In a further aspect, herein provided is a method of producing a polyketide, the method comprising: providing a yeast cell comprising a first polynucleotide coding for a polyketide synthase enzyme and propagating the yeast cell for providing a yeast cell culture. Tpolyketide synthase enzyme is for producing at least one species of polyketide from malonyl-CoA, the polyketide having structure I:

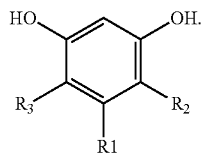

On structure I, R1 is a pentyl group. On structure I, R2 is H, carboxyl, or methyl. On structure I, R3 is H, carboxyl, or methyl.

In some embodiments, the polyketide synthase enzyme comprises a DiPKS polyketide synthase enzyme from *D. discoideum*. In some embodiments, the first polynucleotide comprises a coding sequence for the DiPKS polyketide synthase enzyme with a primary structure having between 80% and 100% amino acid residue sequence homology with a protein coded for by a reading frame defined by bases 535 to 9978 of SEQ ID NO: 13. In some embodiments, the first polynucleotide has between 80% and 100% base sequence homology with bases 535 to 9978 of SEQ ID NO: 13. In some embodiments, the at least one species of polyketide comprises a polyketide with a methyl group at R2. In some embodiments, he DiPKS polyketide synthase enzyme comprises a mutation affecting an active site of a C-Met domain for mitigating methylation of the at least one species of polyketide, resulting in the at least one species of polyketide comprising a first polyketide wherein R2 is methyl and R3 is H, and a second polyketide wherein R2 is H and R3 is H. In some embodiments, the DiPKS polyketide synthase comprises a DiPKS$^{G1516D;\ G1518A}$ polyketide synthase. In some embodiments, the first polynucleotide comprises a coding sequence for the DiPKS$^{G1516D;\ G1518A}$ polyketide synthase enzyme with a primary structure having between 80% and 100% amino acid residue sequence homology with a protein coded for by a reading frame defined by bases 523 to 9966 of SEQ ID NO: 9. In some embodiments, the first polynucleotide has between 80% and 100% base sequence homology with bases 523 to 9966 of SEQ ID NO: 9. In some embodiments, the DiPKS polyketide synthase comprises a DiPKS$^{G1516R}$ polyketide synthase. In some embodiments, the first polynucleotide comprises a coding sequence for the DiPKS$^{G1516R}$ polyketide synthase enzyme with a primary structure having between 80% and 100% amino acid residue sequence homology with a protein coded for by a reading frame defined by bases 523 to 9966 of SEQ ID NO: 10. In some embodiments, the first polynucleotide has between 80% and 100% base sequence homology with bases 523 to 9966 of SEQ ID NO: 10. In some embodiments, the DiPKS polyketide synthase enzyme comprises a mutation reducing activity at an active site of a C-Met domain of the DiPKS polyketide synthase enzyme, for preventing methylation of the at least one species of polyketide, resulting in the at least one species of polyketide having a hydrogen R2 group and a hydrogen R3 group. In some embodiments, the yeast cell comprises a second polynucleotide coding for a phosphopantetheinyl transferase enzyme for increasing the activity of DiPKS. In some embodiments, the phosphopantetheinyl transferase comprises NpgA phosphopantetheinyl transferase enzyme from *A. nidulans*. In some embodiments, wherein the second polynucleotide comprises a coding sequence for the NpgA phosphopantetheinyl transferase enzyme from *A. nidulans* with a primary structure having between 80% and 100% amino acid residue sequence homology with a protein coded for by a reading frame defined by bases 1170 to 2201 of SEQ ID NO: 8. In some embodiments, the second polynucleotide has between 80% and 100% base sequence homology with bases 1170 to 2201 of SEQ ID NO: 8.

In some embodiments, the polyketide synthase enzyme comprises an active site for synthesizing the at least one species of polyketide from malonyl-CoA without a longer chain ketyl-CoA. In some embodiments, the at least one species of polyketide comprises at least one of olivetol, olivetolic acid, methyl-olivetol, or methyl-olivetolic acid.

In some embodiments, R2 is H and R3 is H.

In some embodiments, R2 is carboxyl and R3 is H.

In some embodiments, R2 is methyl and R3 is H.

In some embodiments, R2 is carboxyl and R3 is methyl

In some embodiments, the yeast cell comprises a genetic modification to increase available malonyl-CoA. In some embodiments, the genetic modification comprises increased expression of Maf1. In some embodiments, the yeast cell comprises a second polynucleotide including a coding sequence for Maf1 with a primary structure having between 80% and 100% amino acid residue sequence homology with a protein coded for by a reading frame defined by bases 936 to 2123 of SEQ ID NO: 6. In some embodiments, the second polynucleotide further comprises a promoter sequence, a terminator sequence and integration sequences, and has between 80% and 100% base sequence homology with SEQ ID NO: 6. In some embodiments, the genetic modification comprises cytosolic expression of an aldehyde dehydrogenase and an acetyl-CoA synthase. In some embodiments, the yeast cell comprises a second polynucleotide including a coding sequence for Acs$^{L641P}$ from *S. enterica* with a primary structure having between 80% and 100% amino acid residue sequence homology with a protein coded for by a reading frame defined by bases 3938 to 5893 of SEQ ID NO:

2, and a coding sequence for Ald6 from *S. cerevisiae* with a primary structure having between 80% and 100% amino acid residue sequence homology with a protein coded for by a reading frame defined by bases 1494 to 2999 of SEQ ID NO 2. In some embodiments, the second polynucleotide further comprises a promoter sequence, a terminator sequence and integration sequences, and has between 80% and 100% base sequence homology with bases 51 to 7114 SEQ ID NO: 2. In some embodiments, the genetic modification comprises increased expression of malonyl-CoA synthase. In some embodiments, the yeast cell comprises a second polynucleotide including a coding sequence for a coding sequence for Acc1$^{S659A;\ S1167A}$ from *S. cerevisiae*. In some embodiments, the second polynucleotide includes a coding sequence for the Acc1$^{S659A;\ S1167A}$ enzyme, with a portion thereof having a primary structure with between 80% and 100% amino acid residue sequence homology with a protein portion coded for by a reading frame defined by bases 9 to 1716 of SEQ ID NO: 5. In some embodiments, the second polynucleotide further comprises a promoter sequence, a terminator sequence and integration sequences, and has between 80% and 100% base sequence homology with SEQ ID NO: 5. In some embodiments, the genetic modification comprises increased expression of an activator for sterol biosynthesis. In some embodiments, the yeast cell comprises a second polynucleotide including a coding sequence for Upc2$^{E888D}$ from *S. cerevisiae* with a primary structure having between 80% and 100% amino acid residue sequence homology with a protein coded for by a reading frame defined by bases 975 to 3701 of SEQ ID NO: 7. In some embodiments, the second polynucleotide further comprises a promoter sequence, a terminator sequence and integration sequences, and has between 80% and 100% base sequence homology with SEQ ID NO: 7

In some embodiments, the method includes extracting the at least one species of polyketide from the yeast cell culture.

In a further aspect, herein provided is a yeast cell for producing at least one species of polyketide. The yeast cell includes a first polynucleotide coding for a polyketide synthase enzyme.

In some embodiments, features of one or more of the yeast cell, the first polynucleotide, or the second polynucleotide described herein are included in the yeast cell.

In a further aspect, herein provided is a method of transforming a yeast cell for production of at least one species of polyketide, the method comprising introducing a first polynucleotide coding for a polyketide synthase enzyme into the yeast cell line.

In some embodiments, features of one or more of the yeast cell, the first polynucleotide, or the second polynucleotide described herein are introduced into the yeast cell.

In a further aspect, herein provided is a method of producing a polyketide, the method comprising: providing a yeast cell comprising a first polynucleotide coding for a polyketide synthase enzyme and propagating the yeast cell for providing a yeast cell culture. The polyketide synthase enzyme is for producing at least one species of polyketide from malonyl-CoA, the polyketide having structure II:

II

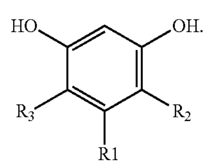

On structure II, R1 is an alkyl group having 1, 2, 3, 4 or 5 carbons. On structure II, R2 is H, carboxyl, or methyl. On structure II, R3 is H, carboxyl, or methyl.

In some embodiments, features of one or more of the yeast cell, the first polynucleotide, or the second polynucleotide described herein are applied to the method.

In a further aspect, herein provided is a polynucleotide comprising a coding sequence for a DiPKSG1516D; G1518A polyketide synthase. In some embodiments, the polynucleotide of claim 45 wherein the DiPKSG1516D; G1518A polyketide synthase enzyme has a primary structure with between 80% and 100% amino acid residue sequence homology with a protein coded for by a reading frame defined by bases 523 to 9966 of SEQ ID NO: 9. In some embodiments, the polynucleotide has between 80% and 100% base sequence homology with bases 523 to 9966 of SEQ ID NO: 9.

In a further aspect, herein provided is a polynucleotide comprising a coding sequence for a DiPKSG1516R polyketide synthase. In some embodiments, the DiPKS$^{G1516R}$ polyketide synthase enzyme has a primary structure with between 80% and 100% amino acid residue sequence homology with a protein coded for by a reading frame defined by bases 523 to 9966 of SEQ ID NO: 10. In some embodiments, the polynucleotide has between 80% and 100% base sequence homology with bases 523 to 9966 of SEQ ID NO: 10.

In a further aspect, herein provided is a DiPKS$^{G1516D;\ G1518A}$ polyketide synthase with a primary structure having between 80% and 100% amino acid residue sequence homology with a protein coded for by a reading frame defined by bases 523 to 9966 of SEQ ID NO: 9.

In a further aspect, herein provided is a DiPKS$^{G1516R}$ polyketide synthase with a primary structure having between 80% and 100% amino acid residue sequence homology with a protein coded for by a reading frame defined by bases 523 to 9966 of SEQ ID NO: 10.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

FIG. 7 is a schematic of functional domains in DiPKS, with mutations to a C-methyl transferase that for lowering methylation of olivetol;

FIG. 8 is a schematic of biosynthesis of methyl-olivetol and olivetol in a transformed yeast cell by DiPKS$^{G1516D; G1518A}$;

FIG. 9 is a schematic of biosynthesis of olivetol in a transformed yeast cell by DiPKS$^{G1516R}$;

DETAILED DESCRIPTION

Generally, the present disclosure provides methods and yeast cell lines for producing olivetol similar to the olivetolic acid that is naturally biosynthesized in the *Cannabis sativa plant*, and for producing methyl-olivetol. The olivetol and methyl-olivetol may be produced in transgenic yeast. The methods and cell lines provided herein include application of genes for enzymes absent from the *C. sativa* plant. Compared with approaches that use *C. sativa* OAS and OAC, the methods and cell lines provided herein result in olivetol and methyl-olivetol being synthesized rather than olivetolic acid, which may provide one or more benefits including biosynthesis of decarboxylated phytocannabinoids, biosynthesis of methylated phytocannabinoid analogues, and biosynthesis production of phytocannabinoids without an input of hexanoic acid, which is toxic to *Saccharomyces cerevisiae* and other species of yeast.

The qualifier "decarboxylated" as used herein references a form of a phytocannabinoid or phytocannabinoid analogue lacking an acid group at, e.g. positions 2 or 4 of Δ9-tetrahydrocannabinol ("THC"), or an equivalent location in other phytocannabinoids or analogues corresponding to position 4 of olivetolic acid, which is the precursor to biosynthesis of CBGa in *C. sativa*. Acid forms of phytocannabinoids are biosynthesized from olivetolic acid in *C. sativa*. When the acid forms of phytocannabinoids are heated, the bond between the aromatic ring of the phytocannabinoid and the carboxyl group is broken. Decarboxylation results from heating carboxylated phytocannabinoids produced in *C. sativa*, which occurs rapidly during combustion or heating to temperatures generally above about 110° C. For simplicity, as used herein, "decarboxylated" refers to phytocannabinoids lacking the acid groups whether or not the phytocannabinoid included an acid group that was lost during true decarboxylation, or was biosynthesized without the carboxyl group.

Figure 1:
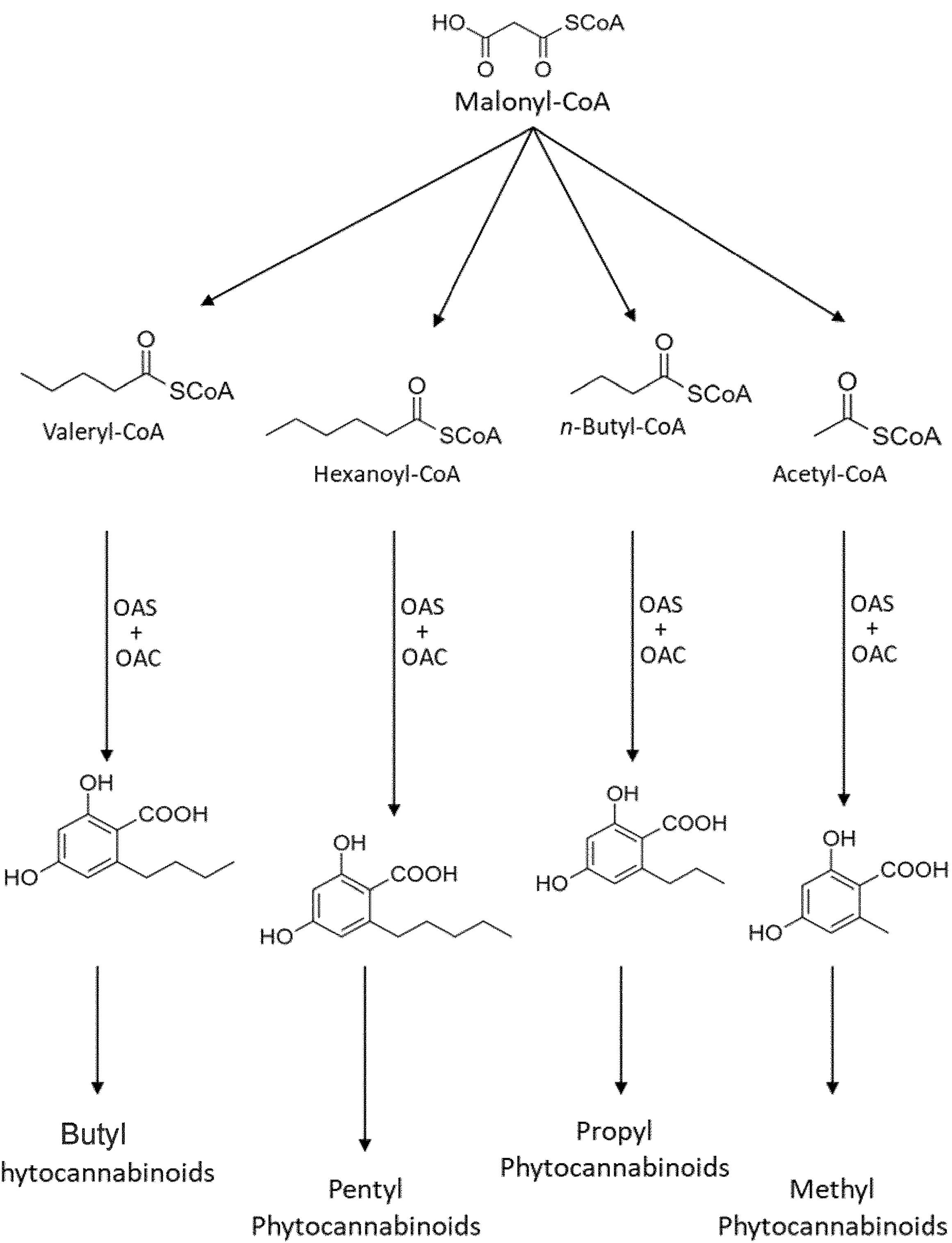
FIG. 1 is a schematic of biosynthesis of olivetolic acid and related compounds with different alkyl group chain lengths in *C. sativa;*

FIG. 1 shows biosynthesis of olivetolic acid from polyketide condensation products of malonyl-CoA and hexanoyl-CoA, as occurs in in *C. sativa*. Olivetolic acid is a metabolic precursor to CBGa. CBGa is a precursor to a large number of downstream phytocannabinoids as described in further detail below. In most varieties of *C. sativa*, the majority of phytocannabinoids are pentyl-cannabinoids, which are biosynthesized from olivetolic acid, which is in turn synthesized from malonyl-CoA and hexanoyl-CoA at a 2:1 stoichiometric ratio. Some propyl-cannabinoids are observed, and are often identified with a "v" suffix in the widely-used three letter abbreviations (e.g. tetrahydrocannabivarin is commonly referred to as "THCv", cannabidivarin is commonly referred to as "CBDv", etc.). FIG. 1 also shows biosynthesis of divarinolic acid from condensation of malonyl-CoA with n-butyl-CoA, which would provide downstream propyl-phytocannabinoids.

FIG. 1 also shows biosynthesis of orsellinic acid from condensation of malonyl-CoA with acetyl-CoA, which would provide downstream methyl-phytocannabinoids. The term "methyl-phytocannabinoids" in this context means their alkyl side chain is a methyl group, where most phytocannabinoids have a pentyl group on the alkyl side chain and varinnic phytocannabinoids have a propyl group on the alkyl side chain. The context in which meCBG and other methylated phytocannabinoid analogues are called "methylated" is different from and parallel to use of "methyl" as a prefix in "methyl-phytocannabinoids" and in FIG. 1. Similarly, since olivetol has a side chain of defined length (otherwise it would be one of the other three polyketides shown in FIG. 1 and not "olivetol"), methyl-olivetol is a reference to methylation on the ring and not to a shorter side chain.

FIG. 1 also shows biosynthesis of 2,4-diol-6-propylbenzenoic acid from condensation of malonyl-CoA with valeryl-CoA, which would provide downstream butyl-phytocannabinoids.

Figure 2:
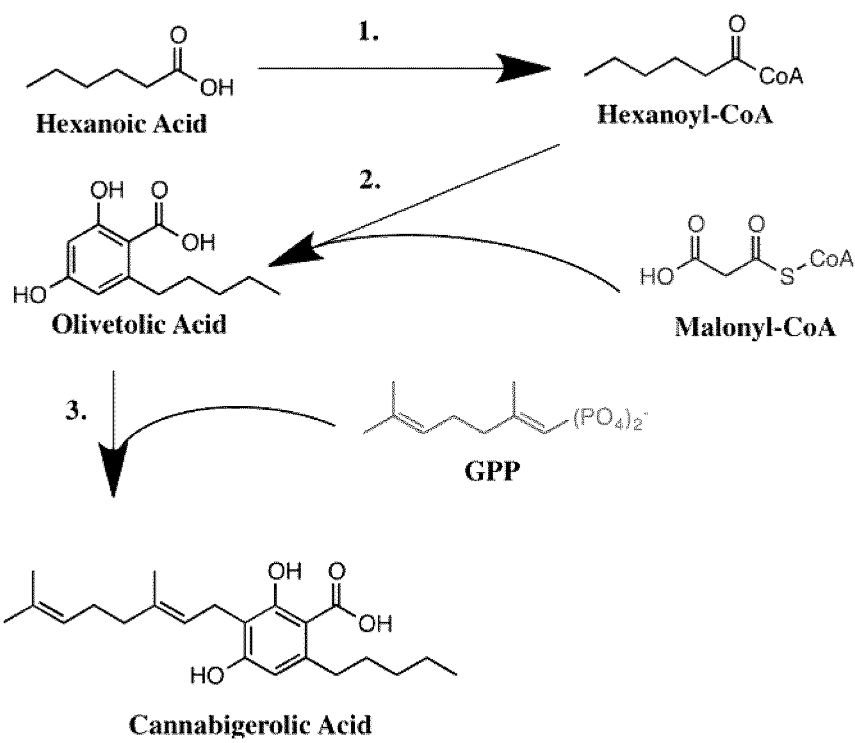
FIG. 2 is a schematic of biosynthesis of CBGa from hexanoic acid, malonyl-CoA, and geranyl pyrophosphate in *C. sativa;*

FIG. 2 shows biosynthesis of CBGa from hexanoic acid, malonyl-CoA, and geranyl pyrophosphate ("GPP") in *C. sativa*, including the olivetolic acid biosynthesis step shown in FIG. 1. Hexanoic acid is activated with coenzyme A by hexanoyl-CoA synthase ("Hex1; Reaction 1 in FIG. 2). Polyketide synthase (also called olivetolic acid synthase "OAS" despite synthesizing olivetol and not olivetolic acid) and OAC together catalyze production of olivetolic acid from hexanoyl CoA and malonyl-CoA (Reaction 2 in FIG. 2). Prenyltransferase combines olivetolic acid with GPP, providing CBGa Step 3 in FIG. 2).

Figure 3:
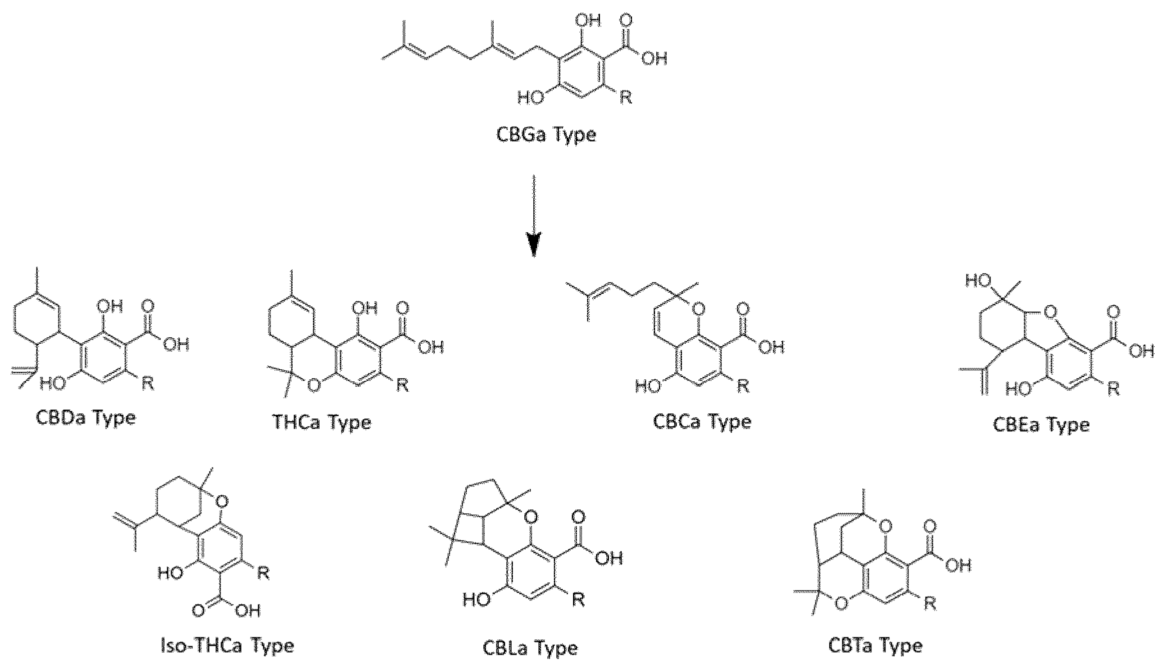
FIG. 3 is a schematic of biosynthesis of downstream phytocannabinoids in the acid form from CBGa in *C. sativa;*

FIG. 3 shows biosynthesis of downstream acid forms of phytocannabinoids in *C. sativa* from CBGa. CBGa is oxidatively cyclized into Δ9-tetrahydrocannabinolic acid ("THCa") by THCa synthase. CBGa is oxidatively cyclized into cannabidiolic acid ("CBDa") by CBDa synthase. Other phytocannabinoids are also synthesized in *C. sativa*, such as cannabichromenic acid ("CBCa"), cannabielsoinic acid ("CBEa"), iso-tetrahydrocannabinolic acid ("iso-THCa"), cannabicyclolic acid ("CBLa"), or cannabicitrannic acid ("CBTa") by other synthase enzymes, or by changing conditions in the plant cells in a way that affects the enzymatic activity in terms of the resulting phytocannabinoid structure. The acid forms of each of these general phytocannabinoid types are shown in FIG. 3 with a general "R" group to show the alkyl side chain, which would be a 5-carbon chain where olivetolic acid is synthesized from hexanoyl-CoA and malonyl-CoA. In some cases, the carboxyl group is alternatively found on a ring position opposite the R group from the position shown in FIG. 3 (e.g. positions 4 of THC rather than position 2 as shown in FIG. 3, etc.). The decarboxylated forms of the acid forms of the phytocannabinoids shown in FIG. 3 are, respectively, THC, cannabidiol ("CBD"), cannabichromene ("CBC"), cannabielsoin ("CBE"), iso-tetrahydrocannabinol ("iso-THC"), cannabicyclol ("CBL"), or cannabicitran ("CBT").

Figure 4:
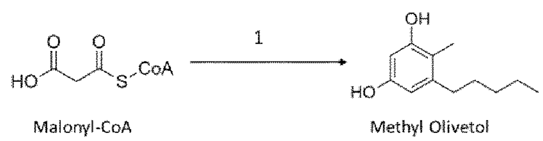
FIG. 4 is a schematic of biosynthesis of olivetolic acid in a transformed yeast cell by DiPKS.

FIG. 4 shows a biosynthetic pathway in transgenic yeast for production of methyl-olivetol from malonyl-CoA. A strain of yeast as provided herein for producing methyl-olivetol as shown in FIG. 4 may include the DiPKS enzyme, which supports production of polyketides from malonyl-CoA only, with no requirement for hexanoic acid from the media. As above, DiPKS includes functional domains similar to domains found in a fatty acid synthase, a methyltransferase domain, and a Pks III domain (see FIG. 7), and is accordingly referred to as a FAS-PKS enzyme. Examples of yeast strains including a codon optimized synthetic sequence coding for the wildtype DiPKS gene are provided as “HB80” and “HB98”, each of which are described in Table 3.

Figure 5:
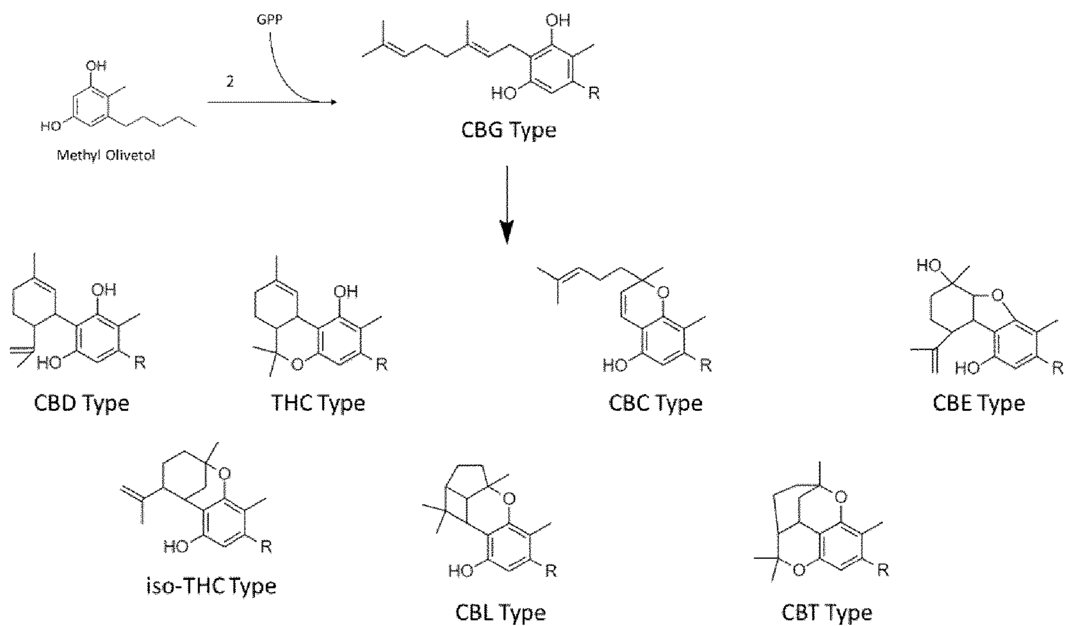
FIG. 5 is a schematic of biosynthesis of meCBG and downstream methylated phytocannabinoid analogues in a transformed yeast cell from methyl-olivetol.
Figure 6:
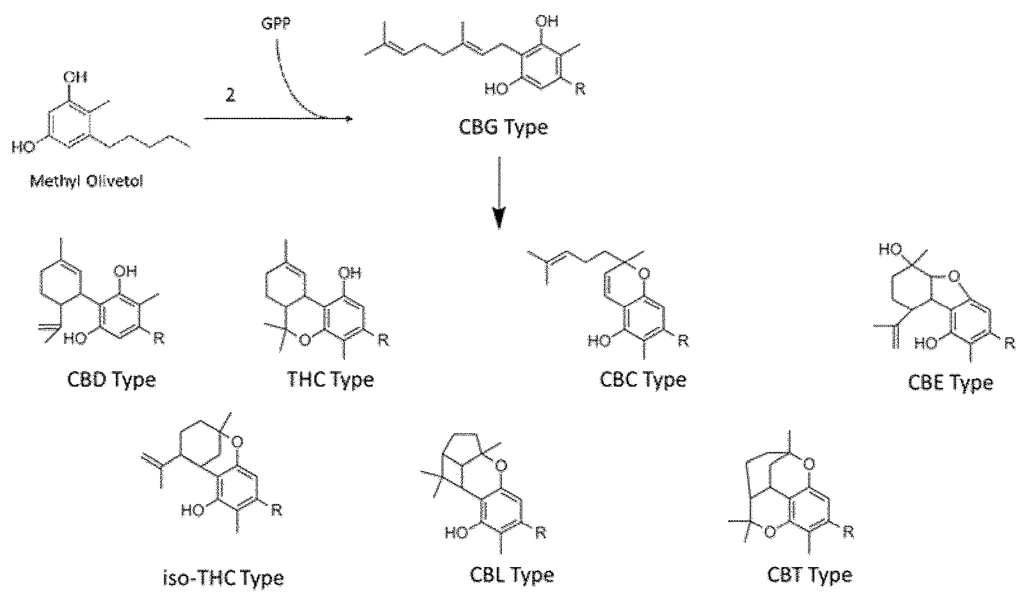
FIG. 6 is a schematic of biosynthesis of meCBG and downstream methylated phytocannabinoid analogues in a transformed yeast cell from methyl-olivetol.

FIGS. 5 and 6 show prenylation of the methyl-olivetol with GPP as a prenyl group donor, providing meCBG (Reaction 2 in FIGS. 5 and 6, following Reaction 1 from FIG. 4). Application of DiPKS rather than OAS facilitates production of phytocannabinoids and phytocannabinoid analogues without hexanoic acid supplementation. Since hexanoic acid is toxic to *S. cerevisiae*, eliminating a requirement for hexanoic acid in the biosynthetic pathway for CBG or meCBG may provide greater yields of CBG or meCBG than the yields of CBG in a yeast cell expressing OAS and Hex1.

FIGS. 5 and 6 show downstream methylated phytocannabinoid analogues corresponding to methyl-tetrahydrocannabinol (“meTHC”), methyl-cannabidiol (“meCBD”), methyl-cannabichromene (“meCBC”), methyl-cannabielsoin (“meCBE”), iso-methyl-tetrahydrocannabinol (“iso-meTHC”), methyl-cannabicyclol (“meCBL”), or methyl-cannabicitran (“meCBT”), which are methylated analogues of THC, CBD, CBC, CBE, iso-THC, CBL, and CBT, respectively, that may be prepared when methyl-olivetol is provided as a precursor chemical rather than olivetolic acid or olivetol. The decarboxylated forms of each of these methylated phytocannabinoid analogues are shown in FIGS. 5 and 6 with a general “R” group to show the alkyl side chain, which would be a 5-carbon chain where synthesis results from hexanoyl-CoA and malonyl-CoA, or malonyl-CoA only.

Other than meCBD, a portion of the structure each of the downstream phytocannabinoid anaologues shown in FIGS. 5 and 6 includes rotationally constrained groups bonded with the aromatic ring. As a result, each of the downstream phytocannabinoid analogues shown in FIGS. 5 and 6 other than meCBD may be synthesized from meCBG in one of two rotational isomers. Depending on the rotational isomer of meCBG during synthesis, the methyl group in the resulting cyclized methylated phytocannabinoid analogues may be at the positions shown for the isomers of meTHC, meCBC, meCBE, iso-meTHC, meCBL, or meCBT in FIG. 5, or at the at the positions shown for the isomers of meTHC, meCBC, meCBE, iso-meTHC, meCBL, or meCBT in FIG. 6. References to meTHC, meCBC, meCBE, iso-meTHC, meCBL, or meCBT herein include either or both of the isomers shown in FIGS. 5 and 6.

DiPKS includes a C-methyltransferase domain that methylates olivetol at position 4 on the aromatic ring. As a result, any downstream prenylation would be of methyl-olivetol, resulting in meCBG, a phytocannabinoid analogue, rather than CBGa, which is known to be synthesized in *C. sativa*. Any downstream reactions that may produce phytocannabinoids when using CBGa or CBG as an input would correspondingly produce the decarboxylated species of methylated phytocannabinoid analogues shown in FIGS. 5 and 6, whereas unmethylated acid form of phytocannabinoids would be produced in *C. sativa* (as in FIG. 3). If OAC or another polyketide cyclase were included, the methyl-olivetol may be converted by the OAC or the other polyketide cyclase into meCBGa, as the methylation and carboxylation carbons may be at differing positions. For example, meTHC synthesized from meCBG may be methylated at carbon 4, and could be carboxylated to methyl-tetrahydrocannabinolic acid (“meTHCa”) with the carboxyl group of THCa may be at position 2. Alternatively, meTHC synthesized from meCBG may be methylated at carbon 2, in which case the carboxyl group of THCa may be at position 4. THCa is observed in *C. sativa* with the carboxyl group at the 2 position, or at the 4 position.

FIG. 7 is a schematic of the functional domains of DiPKS showing β-ketoacyl-synthase (“KS”), acyl transacetylase (“AT”), dehydratase (“DH”), C-methyl transferase (“C-Met”), enoyl reductase (“ER”), ketoreductase (“KR”), and acyl carrier protein (“ACP”). The “Type III” domain is a type 3 polyketide synthase. The KS, AT, DH, ER, KR, and ACP portions provide functions typically associated with a fatty acid synthase. The C-Met domain provides the catalytic activity for methylating olivetol at carbon 4. The C-Met domain is crossed out in FIG. 7, schematically illustrating modifications to DiPKS protein that inactivate the C-Met domain and mitigate or eliminate methylation functionality. The Type III domain catalyzes iterative polyketide extension and cyclization of a hexanoic acid thioester transferred to the Type III domain from the ACP.

FIG. 8 shows a biosynthetic pathway in transgenic yeast for production of both meCBG and CBG from malonyl-CoA and GPP. A strain of yeast as provided herein for producing both CBG and meCBG as shown in FIG. 8 may include the gene for a prenyltransferase and a gene for a mutant DiPKS with a lowered activity at the C-Met domain, as shown schematically in FIG. 7. The C-Met domain of the DiPKS protein includes amino acid residues 1510 to 1633 of DiPKS. The C-Met domain includes three motifs. The first motif includes residues 1510 to 1518. The second motif includes residues 1596 to 1603. The third motif includes residues 1623 to 1633. Disruption of one or more of these three motifs may result in lowered activity at the C-Met domain.

An example of a yeast strain expressing a modified DiPKS with lowered activity in the C-Met domain is provided as “HB80A” in Example III below. HB80A includes a modification in a yeast-codon optimized gene coding for the wildtype DiPKS protein. HB80A includes modifications in the DiPKS gene such that the DiPKS protein is modified in the first motif of the C-Met domain. As a result of these modifications to the DiPKS gene, the DiPKS protein has substitutions of Gly1516Asp and Glyl518Ala. HB80A includes DiPKS$^{G1516D; G1518A}$, and as a result catalyzes both step 1A and 1B of FIG. 8, and produces both methyl-olivetol and olivetol.

FIG. 8 shows production of both methyl-olivetol from malonyl-CoA (Reaction 1A in FIG. 8) and of olivetol from malonyl-CoA (Reaction 1B in FIG. 8). Reactions 1A and 1B are each catalyzed by DiPKS$^{G1516D; G1518A}$. The Gly1516Asp and Glyl518Ala substitutions are in the active site of the C-Met domain and diminish catalysis by DiPKS$^{G1516D; G1518A}$ of methylation on the 4 position of the olivetol ring, allowing a portion of the input malonyl-CoA to be catalyzed according to reaction 1B rather than reaction 1A. A promiscuous αββα prenyltransferase could then catalyze prenylation of both the methyl-olivetol with GPP and the olivetol with GPP, resulting in production of both meCBG (Reaction 2 in FIGS. 5 and 6) and CBG through prenylation of olivetol, similar to reaction 3 in FIG. 2 but without the acid group. Any downstream reactions to produce other phytocannabinoids would then correspondingly produce a mixture of methylated phytocannabinoid analogues and species with no functional group at the 4 position on the aromatic ring of CBG (or a corresponding position in downstream phytocannabinoids), whereas acid forms would be produced in *C. sativa.*

FIG. 9 shows a biosynthetic pathway in transgenic yeast for production of olivetol only, and no methyl-olivetol, from malonyl-CoA. A strain of yeast as provided herein for producing olivetol only as shown in FIG. 9 may include the gene for a mutant DiPKS with a lowered activity at the C-Met domain, as shown schematically in FIG. 7.

Examples of yeast strains expressing a modified DiPKS with essentially no activity in the C-Met domain are provided as "HB135", "HB137", and "HB138" in Examples VI and VII below. Each of HB135, HB137 and HB138 includes a modification in a yeast-codon optimized gene coding for the wildtype DiPKS protein. HB135, HB137 and HB138 each include a modification of the DiPKS gene such that the DiPKS protein is modified in the first motif of the C-Met domain. As a result of this modification to the DiPKS gene, the DiPKS protein has substitutions of Gly1516Arg.

$DipKs^{G1516R}$ catalyzes reaction 1 in FIG. 9. The Gly1516Arg substitution is in the active site of the C-Met domain and diminish catalysis by $DiPKS^{G1516R}$ of methylation on the 4 position of the olivetol ring. The input of malonyl-CoA is catalyzed according to reaction 1 of FIG. 9. Any downstream reactions to produce other phytocannabinoids would then correspondingly produce phytocannabinoid species with no functional group at the 4 position on the aromatic ring of CBG, or a corresponding position in downstream phytocannabinoids, whereas acid forms would be produced in *C. sativa.*

Increasing Availability of Biosynthetic Precursors

The biosynthetic pathways shown in FIGS. 4, 8 and 9 each require malonyl-CoA to produce methyl-olivetol only, both methyl-olivetol and olivetol, and olivetol only, respectively. Yeast cells may be mutated, genes from other species may be introduced, genes may be upregulated or downregulated, or the yeast cells may be otherwise genetically modified to increase the availability of malonyl-CoA or other input metabolites required to support the biosynthetic pathways of any of FIG. 4, 8 or 9.

The yeast strain may be modified for increasing available malonyl-CoA. Lowered mitochondrial acetaldehyde catabolism results in diversion of the acetaldehyde from ethanol catabolism into acetyl-CoA production, which in turn drives production of malonyl-CoA and downstream polyketides and terpenoids. *S. cerevisiae* may be modified to express an acetyl-CoA synthase from *Salmonella enterica* with a substitution modification of Leucine to Proline at residue 641 ("$Acs^{L641P}$") and with aldehyde dehydrogenase 6 from *S. cerevisiae* ("Ald6"). The Leu641Pro mutation removes downstream regulation of Acs, providing greater activity with the $Acs^{L641P}$ mutant than the wild type Acs. Together, cytosolic expression of these two enzymes increases the concentration of acetyl-CoA in the cytosol. Greater acetyl-CoA concentrations in the cytosol result in lowered mitochondrial catabolism, bypassing mitochondrial pyruvate dehydrogenase ("PDH"), providing a PDH bypass. As a result, more acetyl-CoA is available for malonyl-CoA production. SEQ ID NO: 2 is plasmid based on the pGREG plasmid and including a DNA sequence coding for the genes for Ald6 and $SeAcs^{L641P}$, promoters, terminators, and integration site homology sequences for integration into the *S. cerevisiae* genome at Flagfeldt-site 19 by recombination applying clustered regularly interspaced short palindromic repeats ("CRISPR"). As shown in Table 2 below (by the term "PDH bypass"), each of base strains "HB82", "HB100", "HB106", and "HB110". have a portion of SEQ ID NO: 2 from bases 1494 to 2999 that code for Ald6 under the $TDH_3$ promoter, and a portion of SEQ ID NO: 2 from bases 3948 to 5893 that code for $SeAcs^{L641P}$ under the $Tef1_P$ promoter. Similarly, each modified yeast strain based on any of HB82, HB100, HB106, or HB110 includes a polynucleotide coding for Ald6 and $SeAcs^{L641P}$.

Another approach to increasing cytosolic malonyl-CoA is to upregulate Acc1, which is the native yeast malonyl-CoA synthase. The promoter sequence of the Acc1 gene was replaced by a constitutive yeast promoter for the PGK1 gene. The promoter from the PGK1 gene allows multiple copies of Acc1 to be present in the cell. The native Acc1 promoter allows only a single copy of the protein to be present in the cell at a time. The native promoter region was marked is shown in SEQ ID NO: 3. The modified promoter region is shown in SEQ ID NO: 4.

In addition to upregulating expression of Acc1, *S. cerevisiae* may include one or more modifications of Acc1 to increase Acc1 activity and cytosolic acetyl-CoA concentrations. Two mutations in regulatory sequences were identified in literature that remove repression of Acc1, resulting in greater Acc1 expression and higher malonyl-CoA production. SEQ ID NO: 5 is a polynucleotide that may be used to modify the *S. cerevisiae* genome at the native Acc1 gene by homologous recombination. SEQ ID NO: 5 includes a portion of the coding sequence for the Acc1 gene with Ser659Ala and Ser1167Ala modifications. As a result, the *S. cerevisiae* transformed with this sequence will express $Acc1^{S659A; S1167A}$. A similar result may be achieved, for example, by integrating a sequence with the Tef1 promoter, the Acc1 with Ser659Ala and Ser1167Ala modifications, and the Prm9 terminator at any suitable site. The end result would be that Tef1, $Acc1^{S659A; S1167A}$, and Prm9 are flanked by genomic DNA sequences for promoting integration into the *S. cerevisiae* genome. This was attempted at Flagfeldt site 18 but due to the size of the construct, the approach with SEQ ID NO: 5 described above was followed instead.

*S. cerevisiae* may include modified expression of Maf1 or other regulators of tRNA biosynthesis. Overexpressing native Maf1 has been shown to reduce loss of IPP to tRNA biosynthesis and thereby improve monoterpene yields in yeast. IPP is an intermediate in the mevalonate pathway. SEQ ID NO: 6 is a polynucleotide that was integrated into the *S. cerevisiae* genome at Maf1-site 5 for genomic integration of Maf1 under the Tef1 promoter. SEQ ID NO: 6 includes the Tef1 promoter, the native Maf1 gene, and the Prm9 terminator. Together, Tef1, Maf1, and Prm9 are flanked by genomic DNA sequences for promoting integration into the *S. cerevisiae* genome. As shown in Table 2 below, base strains HB100, HB106, and HB110 express Maf1 under the Tef1 promoter. Similarly, each modified yeast strain based on any of HB100, HB106, or HB110 includes a polynucleotide including a coding sequence for Maf1 under the Tef1 promoter.

Upc2 is an activator for sterol biosynthesis in *S. cerevisiae*. A Glu888Asp mutation of Upc2 increases monoterpene production in yeast. SEQ ID NO: 7 is a polynucleotide that may be integrated into the genome to provide expression of $Upc2^{E888D}$ under the Tef1 promoter. SEQ ID NO: 7 includes the Tef1 promoter, the $Upc2^{E888D}$ gene, and the Prm9 terminator. Together, Tef1, $Upc2^{E888D}$, and Prm9 are flanked by genomic DNA sequences for promoting integration into the *S. cerevisiae* genome.

Any of the above genes, $Acs^{L641P}$, Ald6, Maf1, $Acc1^{S659A; S1167A}$ or $Upc2^{E888D}$, may be expressed from a plasmid or integrated into the genome of *S. cerevisiae*. Genome integration may be through homologous recombination, including CRISPR recombination, or any suitable approach. The promoter of Acc1 may be similarly modified through recombination. The coding and regulatory sequences in each of SEQ ID NO: 2, SEQ ID NO: 4, SEQ ID NO: 5, SEQ ID NO: 6, or SEQ ID NO: 7 may be included in a plasmid for expression (e.g. pYES, etc.) or a linear polynucleotide for integration into the *S. Cerevisiae* genome. Each of base strains HB82, HB100, HB106, or HB110 includes one or more integrated SEQ ID NO: 2, SEQ ID NO: 4, SEQ ID NO: 6, or SEQ ID NO: 8 (see Table 2 below). Integration of SEQ ID NO: 5, or SEQ ID NO: 7 may be applied by similar approaches.

Increased DiPKS Function

As shown in FIG. 7, DiPKS includes an ACP domain. The ACP domain of DiPKS requires a phosphopantetheine group as a co-factor. NpgA is a 4'-phosphopantethienyl transferase from *Aspergillus nidulans*. A codon-optimized copy of NpgA for *S. cerevisiae* may be introduced into *S. cerevisiae* and transformed into the *S. cerevisiae*, including by homologous recombination. An NpgA gene cassette was integrated into the genome of *Saccharomyces cerevisiae* at Flagfeldt site 14 to create strain HB100. The sequence of the integrated DNA is shown in SEQ ID NO: 8, and includes the Tef1 Promoter, the NpgA coding sequence and the Prm9 terminator. Together the Tef1p, NpgA, and Prm9t are flanked by genomic DNA sequences promoting integration into Flagfeldt site 14 in the *S. cerevisiae* genome. As shown in Table 2 below, base strains HB100, HB106, and HB110 include this integrated cassette. Alternatively, bases 636 to 2782 of SEQ ID NO: 8 may be included on an expression plasmid as in strain HB98.

Expression of NpgA provides the *A. nidulans* phosphopantetheinyl transferase for greater catalysis of loading the phosphopantetheine group onto the ACP domain of DiPKS. As a result, the reaction catalyzed by DiPKS (reaction 1 in FIG. 4) may occur at greater rate, providing a greater amount of methyl-olivetol.

Modification of DiPKS

DiPKS may be modified to reduce or eliminate the activity of C-Met.

SEQ ID NO: 9 is a modified form of a synthetic sequence for DIPKS that is codon optimized for yeast in which DiPKS includes a Gly1516Asp substitution and a Gly1518Ala substitution that together disrupt the activity of the C-met domain. Results of DiPKs$^{G1516D,\ G1518A}$ expression in *S. cerevisiae* cultures are provided below in relation to Example II, which includes strain HB80A. Other modifications may be introduced into DiPKS to disrupt or eliminate the entire active site of C-Met or all of C-Met. Each of these modified DiPKS enzymes may be introduced into *S. cerevisiae* as described for wild type DiPKS.

SEQ ID NO: 10 is a modified form of a synthetic sequence for DIPKS that is codon optimized for yeast in which DiPKS includes a Gly1516Arg substitution that disrupts the activity of the C-met domain. Results of DiPKS$^{G1516R}$ expression in *S. cerevisiae* cultures are provided below in relation to Example VI, which includes strain HB135 and Example VII, which includes strains HB135, HB137 and HB138.

In addition to DiPKS$^{G1516D,\ G1518A}$ and DiPKS$^{G1516R}$ specifically, other modifications were introduced into DiPKS to disrupt or eliminate the entire active site of C-Met or all of C-Met: (a) substitution of motif 1 with GGGSGGGSG, (b) a Gly1516Arg substitution in motif 1 and substitution of motif 2 with GGGSGGGS, (c). a Glu1634Ala, which is just outside motif 3 and disrupts tertiary structure at an active site in the C-Met domain, and (d). disruption of an active site in the C-Met domain by a His1608Gln substitution. Codon optimized sequences for each of (a) to (d) were introduced into yeast on expression plasmids, similarly to expression of DiPKS$^{G1516D,\ G1518A}$ and DiPKS$^{G1516R}$, into base strain HB100. In each case, no production of olivetol was observed. Substitution of either motif 1 or motif 2 with GGGSGGGS eliminated production of methyl-olivetol as well. A culture of yeast expressing the DiPKS$^{G1634A}$ mutant provided 2.67 mg methyl-olivetol per I of culture in one example batch. A culture of yeast expressing the DiPKS$^{H1608N}$ mutants provided 3.19 mg methyl-olivetol per I of culture in one example batch.

Transforming and Growing Yeast Cells

Details of specific examples of methods carried out and yeast cells produced in accordance with this description are provided below as Examples I to VII. Each of these seven specific examples applied similar approaches to plasmid construction, transformation of yeast, quantification of strain growth, and quantification of intracellular metabolites. These common features across the seven examples are described below, followed by results and other details relating to one or more of the seven examples.

Plasmid Construction

Plasmids assembled to apply and prepare examples of the methods and yeast cells provided herein are shown in Table 1. In Table 1, for the expression plasmids pYES, and pYES2, SEQ ID NOs 11 and 12 respectively provide the plasmids as a whole without an expression cassette. The expression cassettes of SEQ ID NOs: 8 to 10, 13 and 14 can be included in to prepare the plasmids indicated in Table 1. SEQ ID NO: 2 is the pGREG plasmid including a cassette for the PDH bypass genes.

TABLE 1

Plasmids and Cassettes Used to Prepare Yeast Strains

| Plasmid | Cassette | Description |
|---|---|---|
| pYES | (none) | LEU auxotroph; ampicillin resistance; SEQ ID NO: 11 |
| pYES2 | (none) | URA auxotroph; ampicillin resistance; SEQ ID NO: 12 |
| pPDH | Bases 1 to 7214 from SEQ ID NO: 2 | High copy amplification plasmid with PDH Bypass genes for acetaldehyde dehydrogenase (Ald6) and acetyl-CoA synthase (Acs$^{L641P}$) assembled in pGREG 505/G418 flanked by integration site homology sequences as follows: |

TABLE 1-continued

| Plasmids and Cassettes Used to Prepare Yeast Strains | | |
|---|---|---|
| Plasmid | Cassette | Description |
| | | C1-506-BclV-Site 19 UP region-L0<br>L0-TDH3$_P$-L1-Ald6-L2-Adh1$_T$-LTP1<br>LTP1-Tef1$_P$-L3-Acs$^{L641P}$-L4-Prm9$_T$-LTP2<br>LTP2-Site 19 down region-C6-506 |
| pNPGa | SEQ ID NO: 8 | High copy NpgA expression plasmid in pYES2 with:<br>LV3-Tef1$_P$-L1-NpgA-L2-Prm9$_T$-LV5 |
| pDiPKSm1 | SEQ ID NO: 9 | High copy DiPKS$^{G1516D;\ G1518A}$ expression plasmid in pYES2 with: LV3-Gal1-L1-DiPKS$^{G1516D;\ G1518A}$-L2-Prm9$_T$-LV5 |
| pDIPKSm2 | SEQ ID NO: 10 | High copy DIPKS$^{G1516R}$ expression plasmid in pYES2 with:<br>LV3-Gal1-L1-DiPKS$^{G1516R}$-L2-Prm9t$_T$-LV5 |
| pDiPKS | SEQ ID NO: 13 | High copy DiPKS expression plasmid in pYES2 with:<br>LV3-Gal1-L1-DiPKS-L2-Prm9$_T$-LV5 |
| pCRISPR | SEQ ID NO: 14 | High copy Cas9 endonuclease and targeted gRNA expression plasmid in pYES2 with:<br>LV3-Tef1$_P$-Cas9-Adh1$_T$-LTP1<br>LTP1-gRNA-LV5 |

Plasmids for introduction into *S. cerevisiae* were amplified by polymerase chain reaction ("PCR") with primers from Operon Eurofins and Phusion HF polymerase (ThermoFisher F-530S) according to the manufacturer's recommended protocols using an Eppendorf Mastercycler ep Gradient 5341.

All plasmids were assembled using overlapping DNA parts and transformation assisted recombination in *S. cerevisiae*. The plasmids were transformed into *S. cerevisiae* using the lithium acetate heat shock method as described by Gietz, R. D. and Schiestl, R. H., "High-efficiency yeast transformation using the LiAc/SS carrier DNA/PEG method." *Nat. Protoc.* 2, 31-34 (2007). The pNPGa, pDiPKSm1, pDiPKSm2, pCRISPR, pDiPKS, and pPDH plasmids were assembled yeast strain HB25, which is a uracil auxotroph. Transformed *S. cerevisiae* cells were selected by auxotrophic selection on agar petri dishes. Colonies recovered from the petri dishes were grown up in liquid selective media for 16 hrs at 30° C. while being shaken at 250 RPM.

After growth in liquid selective media, the transformed *S. cerevisiae* cells were collected and the plasmid DNA was extracted. The extracted plasmid DNA was transformed into *Escherichia coli*. Transformed *E. coli* were selected for by growing on agar petri dishes including ampicillin. The *E. coli* were cultured to amplify the plasmid. The plasmid grown in the *E. coli* was extracted and sequenced with Sanger dideoxy sequencing to verify accurate construction. The sequence-verified plasmid was then used for genome modification or stable transformation of the *S. cerevisiae.*

Genome Modification of *S. cerevisiae*

The *S. cerevisiae* strains described herein may be prepared by stable transformation of plasmids or genome modification. Genome modification may be accomplished through homologous recombination, including by methods leveraging CRISPR.

Methods applying CRISPR were applied to delete DNA from the *S. cerevisiae* genome and introduce heterologous DNA into the *S. cerevisiae* genome. Guide RNA ("gRNA") sequences for targeting the Cas9 endonuclease to the desired locations on the *S. cerevisiae* genome were designed with Benchling online DNA editing software. DNA splicing by overlap extension ("SOEing") and PCR were applied to assemble the gRNA sequences and amplify a DNA sequence including a functional gRNA cassette.

The functional gRNA cassette, a Cas9-expressing gene cassette, and the pYes2 (URA) plasmid were assembled into the pCRISPR plasmid and transformed into *S. cerevisiae* for facilitating targeted DNA double-stranded cleavage. The resulting DNA cleavage was repaired by the addition of a linear fragment of target DNA.

Genome modification of *S. cerevisiae* was based on strain HB42, which is a Uracil auxotroph based in turn on strain HB25, and which includes an integration of the CDS for an Erg20$^{K197E}$ protein. This integration was for other purposes not directly relevant to production of methyl-olivetol or olivetol, but which may be useful when also synthesizing CBG or meCBG, which requires GPP. The Erg20$^{K197E}$ mutant protein increases GPP levels in the cell.

Bases 51 to 7114 of SEQ ID NO: 2 were integrated into the HB42 strain by CRISPR to provide the HB82 base strain with the PDH bypass genes in *S. cerevisiae*. The pPDH plasmid was sequence verified after assembly in *S. cerevisiae*. The sequence-verified pPDH plasmid was grown in *E. coli*, purified, and digested with BciV1 restriction enzymes. As in Table 1, digestion by BciV1 provided a polynucleotide including the genes for Ald6 and SeAcs$^{L641P}$, promoters, terminators, and integration site homology sequences for integration into the *S. cerevisiae* genome at PDH-site 19 by Cas9. The resulting linear PDH bypass donor polynucleotide, shown in bases 51 to 7114 of SEQ ID NO: 2, was purified by gel separation.

With both PDH bypass genes (Ald6 and Acs$^{L641P}$) on the single PDH bypass polynucleotide, the PDH bypass donor polynucleotide was co-transformed into *S. cerevisiae* with pCRISPR. Transformation was by the lithium acetate heat shock method as described by Gietz. The pCRISPR plasmid expresses Cas9, which is targeted to a selected location of *S. cerevisiae* the genome by a gRNA molecule. At the location, the Cas9 protein creates a double stranded break in the DNA. The PDH bypass donor polynucleotide was used as a donor polynucleotide in the CRISPR reaction. The PDH bypass donor polynucleotide including Ald6, Acs$^{L641P}$, promoters, and terminators was integrated into the genome at the site of the break, Site 19, by homologous recombination, resulting in strain HB82.

The NpgA donor polynucleotide shown in SEQ ID NO: 8 was prepared and amplified. DNA SOEing was used to create a single donor DNA fragment from three polynucleotides for NpgA integration. The first polynucleotide was the 5' region of genomic homology that allows the donor to recombine into the genome at a specific locus. The second polynucleotide coded for the NpgA gene cassette. The NpgA gene cassette includes the Tef1 promoter, the NpgA coding sequence and the Prm9 terminator. The third polynucleotide included the 3' region for genomic homology to facilitate targeted integration into the *S. cerevisiae* genome.

The NpgA donor polynucleotide was co-transformed with the pCRISPR plasmid into strain HB82. The pCRISPR plasmid was expressed and endonuclease Cas9 was targeted to a location on the *S. cerevisiae* genome by a gRNA molecule. At the location, the Cas9 protein created a double stranded break in the DNA and the NpgA donor polynucleotide was integrated into the genome at the break by homologous recombination to provide the HB100 base strain.

The Maf1 donor polynucleotide shown in SEQ ID NO: 6 was prepared and amplified. DNA SOEing was used to create a single donor DNA fragment from three polynucleotides for Maf1 integration. The first polynucleotide was the 5' region of genomic homology that allows the donor to recombine into the genome at a specific locus. The second polynucleotide coded for the Maf1 gene cassette. The Maf1 gene cassette includes the Tef1 promoter, the Maf1 coding sequence and the Prm9 terminator. The third polynucleotide included the 3' region for genomic homology to facilitate targeted integration into the *S. cerevisiae* genome.

The Maf1 donor polynucleotide was co-transformed with the pCRISPR plasmid into the HB100 strain. The pCRISPR plasmid may be expressed and endonuclease Cas9 was targeted to a location on the *S. cerevisiae* genome by a gRNA molecule. At the location, the Cas9 protein may create a double stranded break in the DNA and the Maf1 donor polynucleotide may be integrated into the genome at the break by homologous recombination. Stable transformation of the Maf1 donor polynucleotide into the HB100 strain provides the HB106 base strain.

The Acc1-PGK1p donor polynucleotide shown in SEQ ID NO: 6 was prepared and amplified. DNA SOEing was used to create a single donor DNA fragment from three polynucleotides for Acc1-PGK1 integration. The first polynucleotide was the 5' region of genomic homology that allows the donor to recombine into the genome at a specific locus. The second polynucleotide coded for the PGK1 promoter region. The third polynucleotide included the 3' region for genomic homology to facilitate targeted integration into the *S. cerevisiae* genome.

The Acc1-PGK1 donor polynucleotide was co-transformed with the pCRISPR plasmid. The pCRISPR plasmid was expressed and endonuclease Cas9 was targeted to a location on the *S. cerevisiae* genome by a gRNA molecule. At the location, the Cas9 protein created a double stranded break in the DNA and the Acc1-PGK1 donor polynucleotide was integrated into the genome at the break by homologous recombination. Stable transformation of donor polynucleotide into the HB100 strain provides the HB110 base strain with Acc1 under regulation of the PGK1 promoter.

Table 2 provides a summary of the base strains that were prepared by genome modification of *S. cerevisiae*. Each base strain shown in Table 2 is a leucine and uracil auxotroph, and none of them include a plasmid.

TABLE 2

Base Transformed Strains Prepared for Polyketide Production

| Strain | Modification | Integration |
|---|---|---|
| HB82 | PDH bypass | SEQ ID NO: 2 |
| HB100 | PDH bypass, NPGa (site 14) | SEQ ID NOs: 2, 8 |
| HB106 | PDH bypass, NPGa (site 14), Maf1 (site 5) | SEQ ID NOs: 2, 8, 6 |
| HB110 | PDH bypass, NPGa (site 14), Maf1 (site 5), Acc1 promoter replaced with $PGK1^{P}$ | SEQ ID NOs: 2, 8, 6, 4 |

Stable Transformation for Strain Construction

Plasmids were transformed into *S. cerevisiae* using the lithium acetate heat shock method as described by Gietz.

Transgenic *S. cerevisiae* HB80, HB98, HB102, HB135, HB137 and HB138 were prepared from the HB42, HB100, HB106 and HB110 bases strain by transformation of HB42 with expression plasmids, and HB80A was prepared by transformation of HB80, as shown below in Table 3. HB80, HB98 and HB102 each include and express DiPKS. HB80A includes and expresses $DiPKS^{G1516D;\ G1518A}$. HB135, HB137 and HB138 each include and express $DiPKS^{G1516R}$. HB98 includes and expresses DiPKS and NPGa from a plasmid.

TABLE 3

Strains including plasmids expressing polyketide synthase

| Strain | Base Strain | Plasmid |
|---|---|---|
| HB80 | HB42 | pDiPKS |
| HB80A | HB80 | pDIPKSml |
| HB98 | HB42 | pDiPKS<br>pNPGa |
| HB102 | HB100 | pDIPKS |
| HB135 | HB100 | pDIPKSm2 |
| HB137 | HB106 | pDIPKSm2 |
| HB138 | HB110 | pDIPKSm2 |

Yeast Growth and Feeding Conditions

Yeast cultures were grown in overnight cultures with selective media to provide starter cultures. The resulting starter cultures were then used to inoculate triplicate 50 ml cultures to an optical density at having an absorption at 600 nm ("$A_{600}$") of 0.1.

Yeast was cultured in media including YNB+2% raffinose+2% galactose+1.6 g/L 4DO*. "4DO*" refers to yeast synthetic dropout media supplement lacking leucine and uracil. "YNB" is a nutrient broth including the chemicals listed in the first two columns side of Table 4. The chemicals listed in the third and fourth columns of Table 4 are included in the 4DO* supplement.

TABLE 4

YNB Nutrient Broth and 4DO* Supplement

| YNB | | 4DO* | |
|---|---|---|---|
| Chemical | Concentration | Chemical | Concentration |
| Ammonium Sulphate | 5 g/L | Adenine | 18 mg/L |
| Biotin | 2 μg/L | p-Aminobenzoic acid | 8 mg/L |
| Calcium pantothenate | 400 μg/L | Alanine | 76 mg/ml |
| Folic acid | 2 μg/L | Arginine | 76 mg/ml |
| Inositol | 2 mg/L | Asparagine | 76 mg/ml |
| Nicotinic acid | 400 μg/L | Aspartic Acid | 76 mg/ml |
| p-Aminobenzoic acid | 200 μg/L | Cysteine | 76 mg/ml |
| Pyridoxine HCl | 400 μg/L | Glutamic Acid | 76 mg/ml |
| Riboflavin | 200 μg/L | Glutamine | 76 mg/ml |
| Thiamine HCL | 400 μg/L | Glycine | 76 mg/ml |
| Citric acid | 0.1 g/L | Histidine | 76 mg/ml |
| Boric acid | 500 μg/L | myo-Inositol | 76 mg/ml |
| Copper sulfate | 40 μg/L | Isoleucine | 76 mg/ml |
| Potassium iodide | 100 μg/L | Lysine | 76 mg/ml |
| Ferric chloride | 200 μg/L | Methionine | 76 mg/ml |
| Magnesium sulfate | 400 μg/L | Phenylalanine | 76 mg/ml |
| Sodium molybdate | 200 μg/L | Proline | 76 mg/ml |
| Zinc sulfate | 400 μg/L | Serine | 76 mg/ml |
| Potassium phosphate monobasic | 1.0 g/L | Threonine | 76 mg/ml |
| Magnesium sulfate | 0.5 g/L | Tryptophan | 76 mg/ml |
| Sodium chloride | 0.1 g/L | Tyrosine | 76 mg/ml |
| Calcium chloride | 0.1 g/L | Valine | 76 mg/ml |

Quantification of Metabolites

Intracellular metabolites were extracted from the *S. cerevisiae* cells using methanol extraction. One mL of liquid culture was spun down at 12,000×g for 3 minutes. 250 μL of the resulting supernatant was used for extracellular metabolite quantification. The resulting cell pellet was suspended in 200 μl of −40° C. 80% methanol. The mixture was vortexed and chilled on ice for 10 minutes. After chilling on ice for 10 minutes, the mixture was spun down at 15,000×g at 4° C. for 14 minutes. The resulting supernatant was collected. An additional 200 μl of −40° C. 80% methanol was added to the cell debris pellet and the mixture was vortexed and chilled for 10 minutes on ice. After chilling on ice for 10 minutes, the mixture was spun down at 15,000×g at 4° C. for 14 minutes. The resulting 200 μl of supernatant was added to the previously collected 200 μl of supernatant, providing a total of 400 μl of 80% methanol with intracellular metabolites.

Intracellular metabolites were quantified using high performance liquid chromatography ("HPLC") and mass spectrometry ("MS") methods. An Agilent 1260 autosampler and HPLC system connected to a ThermoFinnigan LTQ mass spectrometer was used. The HPLC system included a Zorbax Eclipse C18 2.1 μm×5.6 mm×100 mm column.

The metabolites were injected in 10 μl samples using the autosampler and separated on the HPLC using at a flow rate of 1 ml/min. The HPLC separation protocol was 20 mins total with (a) 0-2 mins of 98% Solvent A and 2% Solvent B; (b) 2-15 mins to get to 98% solvent B; (c) 15-16.5 minutes at 98% solvent B; (d) 16.5-17.5 minutes to get to 98% A; and (e) a final 2.5 minutes of equilibration at 98% Solvent A. Solvent A was acetonitrile+0.1% formic acid in MS water and solvent B was 0.1% formic acid in MS water.

After HPLC separation, samples were injected into the mass spectrometer by electrospray ionization and analyzed in positive mode. The capillary temperature was held at 380° C. The tube lens voltage was 30 V, the capillary voltage was 0 V, and the spray voltage was 5 kV. Similarly, after HPLC-MS/MS, olivetol was analyzed as a parent ion at 181.2 and a daughter ion at 111, while methyl-olivetol analyzed as a parent ion at 193.2 and a daughter ion at 125.

Different concentrations of known standards were injected to create a linear standard curve. Standards for olivetol and methyl-olivetol standards were purchased from Sigma Aldrich.

Example I

The yeast strain HB80 as described above in Table 3 was cultured in the YNB+2% raffinose+2% galactose+1.6 g/L 4DO* media. Production of methyl-olivetol from raffinose and galactose was observed, demonstrating direct production in yeast of methyl-olivetol. The methyl-olivetol was produced at concentrations of 3.259 mg/L.

Example II

The yeast strain HB80A as described above in Table 3 was cultured in the YNB+2% raffinose+2% galactose+1.6 g/L 4DO* media. Production of both olivetol and methyl-olivetol from raffinose and galactose, catalyzed by DiPKS$^{G1516D; G1518A}$, was observed. This data demonstrates direct production in yeast of both olivetol and methyl-olivetol without inclusion of hexanoic acid.

Figure 10:
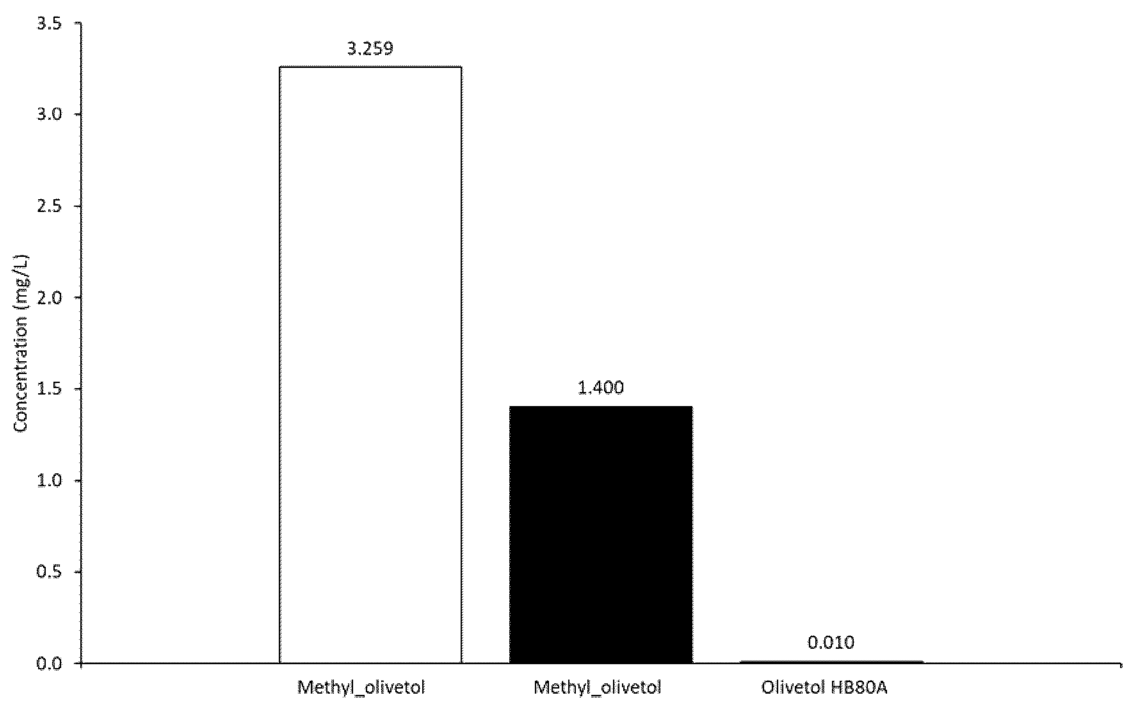
FIG. 10 shows production of methyl-olivetol by DiPKS, and of both methyl-olivetol and olivetol by DiPKS$^{G1516D; G1518A}$.

FIG. 10 shows concentrations of methyl-olivetol produced by HB80 ("Methyl_Olivetol HB80") from Example I, and of both olivetol and methyl-olivetol produced by HB80A ("Methyl_Olivetol HB80A" and "Olivetol HB80A", respectively). Samples of culture were taken at 72 hours. HB80A produces a majority of methyl-olivetol (1.4 mg methyl-olivetol per L of culture compared with 0.010 mg per L of culture olivetol), and produced less methyl-olivetol and olivetol combined than methyl-olivetol that is produced by HB80 (3.26 mg/L).

Example III

The yeast strain HB98 as described above in Table 3 was cultured in the YNB+2% raffinose+2% galactose+1.6 g/L 4DO* media. Production of methyl-olivetol from raffinose and galactose, catalyzed by DiPKS, was observed. This data demonstrates increased methyl-olivetol production compared with HB80 as described in Example I, and also without inclusion of hexanoic acid.

Figure 11:
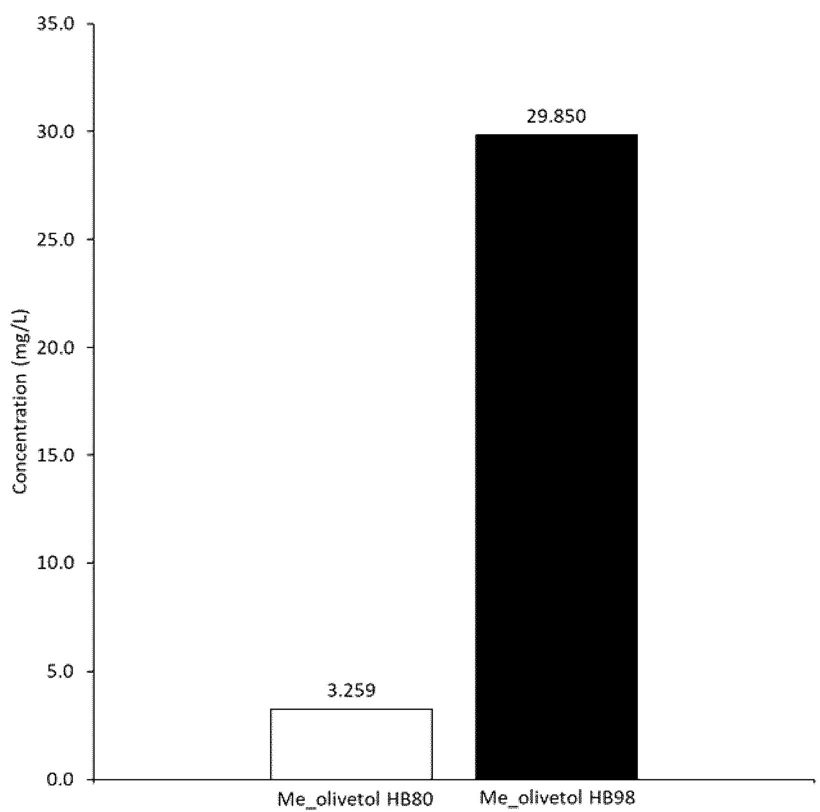
FIG. 11 shows production of methyl-olivetol by DiPKS in two separate strains of *S. cerevisiae;*

FIG. 11 shows concentrations of methyl-olivetol produced by HB80 ("Methyl_Olivetol HB80") from Example I, and of methyl-olivetol produced by HB98 ("Methyl_Olivetol HB98") from Example III. Samples of culture were taken at 72 hours. HB98 produced 29.85 mg/L methyl-olivetol while HB80 produced only 3.26 mg methyl-olivetol per L of culture. HB98 produced nearly 10× as much methyl-olivetol as HB80.

Example IV

The yeast strain HB102 as described above in Table 3 was cultured in the YNB+2% raffinose+2% galactose+1.6 g/L 4DO* media. Production of methyl-olivetol from raffinose and galactose was observed, demonstrating an increased production in yeast of methyl-olivetol at 42.44 mg/L as compared to strain HB98, which produced only 29.85 mg/L methyl-olivetol. This demonstrated that the genomically integrated version of NpgA is functional.

Figure 12:
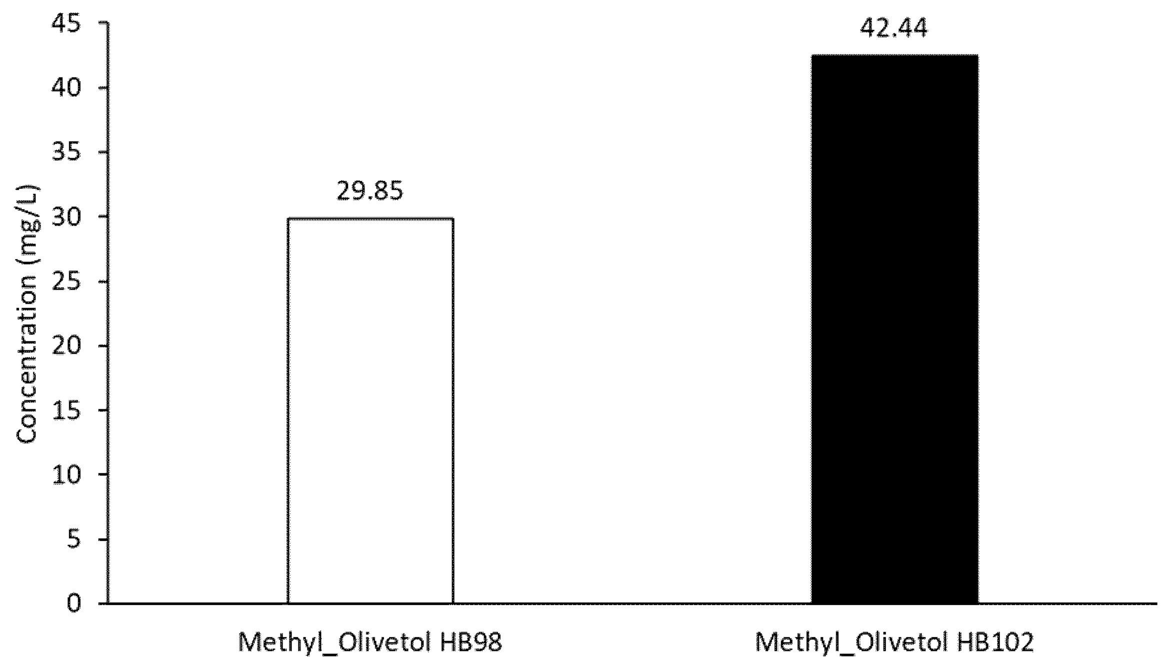
FIG. 12 shows production of methyl-olivetol by DiPKS in two separate strains of *S. cerevisiae;*

FIG. 12 shows concentrations of methyl-olivetol produced by HB102 ("Methyl_olivetol HB102") from Example IV as compared to the production of methyl-olivetol from strain HB98 in Example III ("Methyl_olivetol HB98").

Example V

The yeast strain HB135 as described above in Table 3 was cultured in the YNB+2% raffinose+2% galactose+1.6 g/L 4DO* media. Production of olivetol from raffinose and galactose was observed, demonstrating an production in yeast of olivetol without any hexanoic acid and at high titres of 49.24 mg/L and no production of methyl-olivetol. This is comparable to the production of methyl-olivetol by strain HB102 demonstrating that the mutation of DIPKS was effective in production of Olivetol as opposed to methyl-Olivetol.

Figure 13:
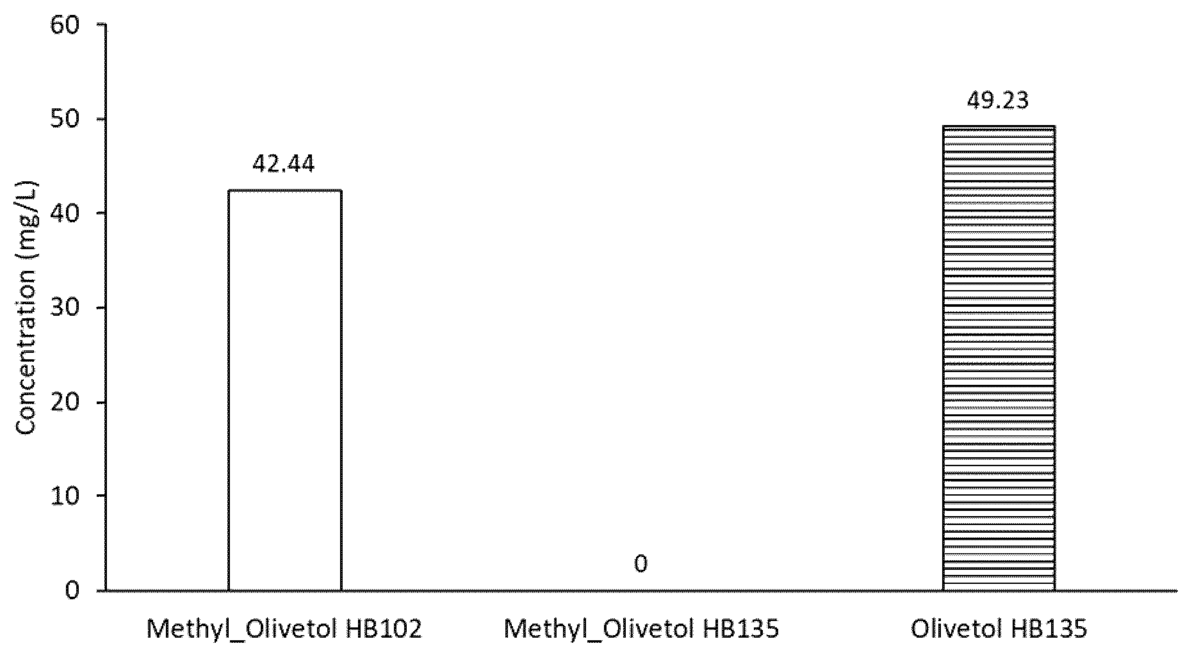
FIG. 13 shows production of methyl-olivetol by DiPKS, and of both methyl-olivetol and olivetol by DiPKS$^{G1516R}$ in two separate strains of *S. cerevisiae*.

FIG. 13 shows concentrations of olivetol and methyl-olivetol produced by HB135 ("Methyl_olivetol HB135" and "Olivetol HB135 respectively) from Example VI as compared to the production of methyl-olivetol from strain HB102 in Example IV ("Methyl_olivetol HB102").

Example VII

The yeast strains HB137 and HB138 as described above in Table 3 were cultured in the YNB+2% raffinose+2% galactose+1.6 g/L 4DO* media. Production of olivetol from raffinose and galactose was observed in both strains. Strain HB137 produced 61.26 mg/L of olivetol and strain HB138 produced 74.26 mg/L of olivetol demonstrating the positive effect of Maf1 integration and Acc1-promoter swap on olivetol titres.

Figure 14:
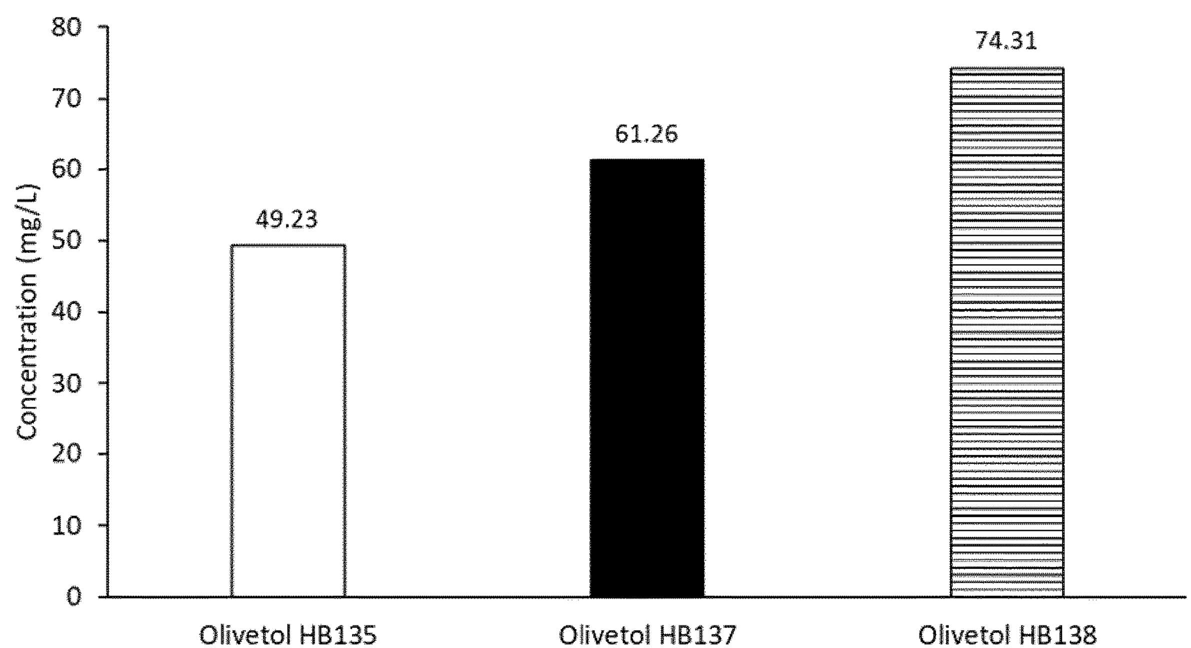
FIG. 14 shows production of olivetol by DiPKS$^{G1516R}$, in three separate strains of *S. cerevisiae.*

FIG. 14 shows the concentrations of olivetol produced by HB137 ("Olivetol HB137") and HB138 ("Olivetol HB138") from Example VII as compared to olivetol produced by HB135 ("Olivetol HB135") in Example VI.

REFERENCES

M. B. Austin, T. Saito, M. E. Bowman, S. Haydock, A. Kato, B. S. Moore, R. R. Kay and Noel, J. P. (2006) "Biosynthesis of *Dictyostelium discoideum* differentiation-inducing factor by a hybrid type I fatty acid-type III polyketide synthase" *Nature chemical biology,* 2(9), 494.

S. W. Baba, G. I. Belogrudov, J. C. Lee, P. T. Lee, J. Strahan and J. N. Shepherd, C. F. Clarke (2003) "Yeast Coq5 C-Methyltransferase Is Required for Stability of Other Polypeptides Involved in Coenzyme Q Biosynthesis" *The Journal of Biological Chemistry,* 279(11): 10052-10059.

C. Chambon, V. Ladeveze, A. Oulmouden, M. Servouse, and E Karst (1990) "Isolation and properties of yeast mutants affected in farnesyl diphosphate synthetase" *Curr Genet,* 18: 41-46.

M. J. C. Fischer, S. Meyer, P. Claudel, M. Bergdoll and F. Karst (2011) "Metabolic Engineering of Monoterpene Synthesis in Yeast" *Biotechnology and Bioengineering,* 108(8): 1883-1892.

Bai Flagfeldt, D., Siewers, V., Huang, L. and Nielsen, J. (2009) "Characterization of chromosomal integration sites for heterologous gene expression in *Saccharomyces cerevisiae" Yeast,* 26, 545-551.

S. Gagne. "The Polyketide Origins of Cannabinoids in *Cannabis sativa*." Diss. U of Saskatchewan, 2013.

R. Ghosh, A. Chhabra, P. A. Phatale, S. K. Samrat, J. Sharma, A. Gosain, D. Mohanty, S. Saran and R. S. Gokhale (2008) "Dissecting the Functional Role of Polyketide Synthases in *Dictyostelium discoideum* biosynthesis of the differentiation regulating factor 4-methyl-5-pentylbenzene-1,3-diol" *Journal of Biological Chemistry,* 283(17), 11348-11354.

C. Huang, H. Wu, Z. Liu, J. Cai, W. Lou and M. Zong (2012) "Effect of organic acids on the growth and lipid accumulation of oleaginous yeast *Trichosporon fermentans" Biotechnology for Biofuels,* 5:4.

Z. Hunkova and Z. Fencl (1977) "Toxic Effects of Fatty Acids on Yeast Cells: Dependence of Inhibitory Effects on Fatty Acid Concentration" *Biotechnology and Bioengineering*, XIX: 1623-1641.

J. Kaminska, K. Grabinska, M. Kwapisz, J. Sikora, W. J. Smagowicz, G. Palamarczyk, T. Zoladek, M. Boguta, "The isoprenoid biosynthetic pathway in *Saccharomyces cerevisiae* is affected in a maf1-1 mutant with altered tRNA synthesis" (2002) *FEMS Yeast Research* 2: 31-37.

D. Ro, E. M. Paradise, M. Ouellet, K. J. Fisher, K. L. Newman, J. M. Ndungu, K. A. Ho, R. A. Eachus, T. S. Ham, J. Kirby, M. C. Y. Chang, S. T. Withers, Y. Shiba, R. Sarpong and J. D. Keasling (2006) "Production of the antimalarial drug precursor artemisinic acid in engineered yeast" *Nature Letters* 440: 930-943.

S. Shi, Y. Chen, V. Siewers and J. Nielsen, "Improving Production of Malonyl Coenzyme A-Derived Metabolites by Abolishing Snf1-Dependent Regulation of Acc1" (2014) *American Society for Microbiology* 5(3): e01130-14. doi:10.1128/mBio.01130-14.

Y. Shiba, E. M. Paradise, J. Kirby, D. Ro and J. D. Keasling "Engineering of the pyruvate dehydrogenase bypass in *Saccharomyces cerevisiae* for high-level production of isoprenoids" (2007) *Metabolic Engineering* 9: 160-168.

M. A. Skiba, A. P. Sikkema, W. D. Fiers, W. H. Gerwick, D. H. Sherman, C. C. Aldrich and J. L. Smith "Domain Organization and Active Site Architecture of a Polyketide Synthase C-methyltransferase" *ACS Chem. Biol.*; Just Accepted Manuscript•DOI: 10.1021/ acschembio.6b00759•Publication Date (Web): 10 Oct. 2016. Downloaded from http://pubs.acs.org on Oct. 11, 2016.

M. Telloa, T. Kuzuyamab, L. Heidec, J. P. Noela and S. B. Richarda (2008) "The ABBA family of aromatic prenyltransferases: broadening natural product diversity" *Cell Mol Life Sci.;* 65(10): 1459-1463.

C. A. Viegas, M. F. Rosa, I. Sa-Correia and J. M. Novais "Inhibition of Yeast Growth by Octanoic and Decanoic Acids Produced during Ethanolic Fermentation" (1989) *Applied and Environmental Microbiology* 55(1): 21-28.

Examples Only

In the preceding description, for purposes of explanation, numerous details are set forth in order to provide a thorough understanding of the embodiments. However, it will be apparent to one skilled in the art that these specific details are not required.

The above-described embodiments are intended to be examples only. Alterations, modifications and variations can be effected to the particular embodiments by those of skill in the art without departing from the scope, which is defined solely by the claims appended hereto.

What is claimed is:

1. A yeast cell for producing at least one species of polyketide, the yeast cell comprising a first polynucleotide coding for a *D. discoideum* polyketide synthase (DiPKS) enzyme, which produces at least one species of polyketide from malonyl-CoA, the polyketide having structure I:

I

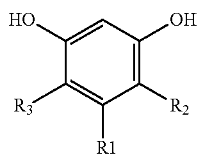

wherein, on structure I, R1 is an alkyl group having 5 carbons, and R2 and R3 are both H, or are methyl and H; and wherein the DiPKS polyketide synthase enzyme has a primary structure with between 99% and 100% amino acid residue sequence identity with a protein coded for by a reading frame defined by bases 523 to 9966 of SEQ ID NO: 13, with a charged amino acid residue at position 1516 in place of a glycine residue at position 1516; and the at least one species of polyketide comprises a first polyketide wherein R2 is H and R3 is H.

2. The yeast cell of claim 1 wherein amino acid residue 1516 of SEQ ID NO:13 is aspartate, amino acid residue 1518 of SEQ ID NO:13 is alanine, and the at least one species of polyketide comprises a second polyketide wherein R2 is methyl and R3 is H.

3. The yeast cell of claim 2 wherein the first polynucleotide comprises a coding sequence for a DiPKS polyketide synthase enzyme coded for by a reading frame defined by bases 523 to 9966 of SEQ ID NO: 9.

4. The yeast cell of claim 1 wherein amino acid residue 1516 of SEQ ID NO: 13 is arginine.

5. The yeast cell of claim 1 wherein the first polynucleotide comprises a coding sequence for a DiPKS polyketide synthase enzyme coded for by a reading frame defined by bases 523 to 9966 of SEQ ID NO: 10.

6. The yeast cell of claim 1 wherein the yeast cell comprises a phosphopantetheinyl transferase polynucleotide coding for a phosphopantetheinyl transferase enzyme for increasing the activity of the DiPKS polyketide synthase enzyme.

7. The yeast cell of claim 6 wherein the phosphopantetheinyl transferase comprises NpgA phosphopantetheinyl transferase enzyme from *A. nidulans*.

8. The yeast cell of claim 6 wherein the phosphopantetheinyl transferase polynucleotide comprises a coding sequence for a phosphopantetheinyl transferase enzyme with a primary structure having between 99% and 100% amino acid residue sequence identity with a protein coded for by a reading frame defined by bases 1170 to 2201 of SEQ ID NO: 8.

9. The yeast cell of claim 1 wherein the at least one species of polyketide comprises at least one of olivetol and methyl-olivetol.

10. The yeast cell of claim 1 wherein the at least one species of polyketide comprises a second polyketide wherein R2 is methyl and R3 is H.

11. The yeast cell of claim 1 wherein the yeast cell comprises a genetic modification to increase available malonyl-CoA.

12. The yeast cell of claim 11 wherein the genetic modification comprises increased expression of a Repressor of RNA polymerase III transcription (Maf1) from *S. cerevisiae*.

13. The yeast cell of claim 11 wherein the yeast cell comprises a Maf1 polynucleotide including a coding sequence for Maf1 coded for by a reading frame defined by bases 936 to 2123 of SEQ ID NO: 6.

14. The yeast cell of claim 11 wherein the genetic modification comprises cytosolic expression of an aldehyde dehydrogenase and an acetyl-coenzyme A synthase.

15. The yeast cell of claim 14 wherein the yeast cell comprises a polynucleotide including a coding sequence for an acetyl-coenzyme A synthase (Acs) with a primary structure having between 99% and 100% amino acid residue sequence identity with a protein coded for by a reading frame defined by bases 3938 to 5893 of SEQ ID NO: 2, and a coding sequence for an aldehyde dehydrogenase with a primary structure having between 99% and 100% amino acid residue sequence identity with a protein coded for by a reading frame defined by bases 1494 to 2999 of SEQ ID NO 2.

16. The yeast cell of claim 11 wherein the genetic modification comprises increased expression of malonyl-CoA synthase.

17. The yeast cell of claim 16 wherein the yeast cell comprises Acetyl-CoA carboxylase (Acc1) polynucleotide including a coding sequence for a coding sequence for $Acc1^{S659A;\ S1157A}$ from *S. cerevisiae.*

18. The yeast cell of claim 17 wherein the Acc1 polynucleotide includes a coding sequence for an Acc1 enzyme coded for by a reading frame defined by bases 9 to 1716 of SEQ ID NO: 5.

19. The yeast cell of claim 11 wherein the genetic modification comprises increased expression of an activator for sterol biosynthesis.

20. The yeast cell of claim 19 wherein the yeast cell comprises sterol uptake control protein 2 (Upc2) polynucleotide including a coding sequence for $Upc2^{E888D}$ from *S. cerevisiae* coded for by a reading frame defined by bases 975 to 3701 of SEQ ID NO: 7.

21. A method of transforming a yeast cell for production of at least one species of polyketide, the polyketide having structure I:

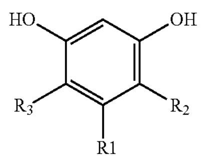

I wherein, on structure I, R1 is an alkyl group having 5 carbons, and R2 and R3 are both H, or are methyl and H; and the at least one species of polyketide comprises a first polyketide wherein R2 is H and R3 is H; and the method comprising introducing a first polynucleotide coding for a *D. discoideum* polyketide synthase (DiPKS) enzyme into the yeast cell line, wherein the DiPKS polyketide synthase enzyme has a primary structure with between 99% and 100% amino acid residue sequence identity with a protein coded for by a reading frame defined by bases 523 to 9966 of SEQ ID NO: 13, with a charged amino acid residue at position 1516 in place of a glycine residue at position 1516.

22. The method of claim 21 wherein amino acid residue 1516 of SEQ ID NO:13 is aspartate, amino acid residue 1518 of SEQ ID NO:13 is alanine, and the at least one species of polyketide comprises a second polyketide wherein R2 is methyl and R3 is H.

23. The method of claim 22 wherein the first polynucleotide comprises a coding sequence for a DiPKS polyketide synthase enzyme coded for by a reading frame defined by bases 523 to 9966 of SEQ ID NO: 9.

24. The method of claim 21 wherein amino acid residue 1516 of SEQ ID NO: 13 is arginine.

25. The method of claim 24 wherein the first polynucleotide comprises a coding sequence for a DiPKS polyketide synthase enzyme coded for by a reading frame defined by bases 523 to 9966 of SEQ ID NO: 10.

26. The method of claim 21 wherein the yeast cell comprises a phosphopantetheinyl transferase polynucleotide coding for a phosphopantetheinyl transferase enzyme for increasing the activity of the DiPKS polyketide synthase enzyme.

27. The method of claim 26 wherein the phosphopantetheinyl transferase comprises NpgA phosphopantetheinyl transferase enzyme from *A. nidulans.*

28. The method of claim 26 wherein the phosphopantetheinyl transferase polynucleotide comprises a coding sequence for the a phosphopantetheinyl transferase enzyme with a primary structure having between 99% and 100% amino acid residue sequence identity with a protein coded for by a reading frame defined by bases 1170 to 2201 of SEQ ID NO: 8.

29. The method of claim 21 wherein the at least one species of polyketide comprises at least one of olivetol and, methyl-olivetol.

30. The method of claim 21 wherein the at least one species of polyketide comprises a second polyketide wherein R2 is methyl and R3 is H.

31. The method of claim 21 wherein the yeast cell comprises a genetic modification to increase available malonyl-CoA.

32. The method of claim 31 wherein the genetic modification comprises increased expression of a Repressor of RNA polymerase III transcription (Maf1) from *S. cerevisiae.*

33. The method of claim 32 wherein the yeast cell comprises a Maf1 polynucleotide including a coding sequence for a Maf1 coded for by a reading frame defined by bases 936 to 2123 of SEQ ID NO: 6.

34. The method of claim 31 wherein the genetic modification comprises cytosolic expression of an aldehyde dehydrogenase and an acetyl-CoA synthase.

35. The method of claim 31 wherein the yeast cell comprises an Acs polynucleotide including a coding sequence for an Acs with a primary structure having between 99% and 100% amino acid residue sequence identity with a protein coded for by a reading frame defined by bases 3938 to 5893 of SEQ ID NO: 2, and a coding sequence for an aldehyde dehydrogenase with a primary structure having between 99% and 100% amino acid residue sequence identity with a protein coded for by a reading frame defined by bases 1494 to 2999 of SEQ ID NO 2.

36. The method of claim 31 wherein the genetic modification comprises increased expression of malonyl-CoA synthase.

37. The method of claim 36 wherein the yeast cell comprises an Acc1 polynucleotide including a coding sequence for a coding sequence for $Acc1^{S659A;\ S1157A}$ from *S. cerevisiae.*

38. The method of claim 37 wherein the Acc1 polynucleotide includes a coding sequence for the $Acc1^{S659A;\ S1157A}$ enzyme coded for by a reading frame defined by bases 9 to 1716 of SEQ ID NO: 5.

39. The method of claim 31 wherein the genetic modification comprises increased expression of an activator for sterol biosynthesis.

40. The method of claim 39 wherein the yeast cell comprises a sterol uptake control protein 2 (Upc2) polynucleotide including a coding sequence for Upc2$^{E888D}$ from *S. cerevisiae* protein coded for by a reading frame defined by bases 975 to 3701 of SEQ ID NO: 7.

* * * * *

SEQUENCE LISTING

```
<160> NUMBER OF SEQ ID NOS: 14

<210> SEQ ID NO 1
<211> LENGTH: 9444
<212> TYPE: DNA
<213> ORGANISM: Artificial Sequence
<220> FEATURE:
<223> OTHER INFORMATION: Yeast optimized DiPKS from Dictyostelium
      discoideum
<220> FEATURE:
<221> NAME/KEY: Motif 1
<222> LOCATION: (4528)..(4554)
<220> FEATURE:
<221> NAME/KEY: C-methyltransferase domain
<222> LOCATION: (4528)..(4890)
<220> FEATURE:
<221> NAME/KEY: Motif 2
<222> LOCATION: (4787)..(4809)
<220> FEATURE:
<221> NAME/KEY: Motif 3
<222> LOCATION: (4867)..(4899)

<400> SEQUENCE: 1

atgaacaaga actccaaaat ccagtcccca aactcttctg atgttgctgt tattggtgtt     60

ggttttagat tcccaggtaa ctctaatgac ccagaatctt tgtggaacaa cttgttggat    120

ggtttcgatg ctattaccca agtcccaaaa gaaagatggg ctacttcttt tagagagatg    180

ggtttgatca agaacaagtt cggtggtttc ttgaaggatt ctgaatggaa gaatttcgac    240

cctttgttct ttggtatcgg tccaaaagaa gctccattca ttgatccaca acaaaggttg    300

ttgttgtcca tcgtttggga atctttggaa gatgcttaca tcagaccaga tgaattgaga    360

ggttctaaca ctggtgtttt catcggtgtt tctaacaacg attacaccaa gttgggtttc    420

caagacaact actctatttc tccatacact atgaccggct ctaactcttc attgaactcc    480

aacagaattt cctactgctt cgattttaga ggtccatcca ttactgttga taccgcttgt    540

tcttcttcct tggtttctgt taatttgggt gtccaatcca tccaaatggg tgaatgtaag    600

attgctattt gcggtggtgt taacgctttg tttgatccat ctacatctgt tgccttttcc    660

aagttgggtg ttttgtctga aaatggcaga tgcaactctt ttagtgatca agcctctggt    720

tacgttagat ctgaaggtgc tggtgttgtt gttttgaagt ctttggaaca agctaagttg    780

gatggtgata gaatctacgg tgttatcaag ggtgtttcct ctaatgaaga tggtgcttct    840

aatggtgaca agaactcttt gactactcca tcttgtgaag cccaatccat taacatttct    900

aaggctatgg aaaaggcctc cttgtctcca tctgatatct attacattga agcccatggt    960

actggtactc cagttggtga tccaattgaa gttaaggcct tgtccaagat cttctccaac   1020

tctaacaaca accagttgaa caacttctct accgatggta atgataacga tgatgatgat   1080

gacgataaca cctctccaga accattattg attggctcat tcaagtccaa catcggtcat   1140
```

-continued

```
ttggaatctg ctgctggtat tgcttctttg attaagtgtt gcttgatgtt gaagaacagg   1200
atgttggttc catccattaa ctgctctaat ttgaacccat ccattccatt cgatcagtac   1260
aacatctccg ttatcagaga aatcagacaa ttcccaaccg ataagttggt taacatcggt   1320
atcaattctt tcggtttcgg tggttctaac tgccatttga ttattcaaga gtacaacaac   1380
aacttcaaga acaactctac catctgcaat aacaacaaca acaacaataa caacatcgac   1440
tacttgatcc caatctcctc taagactaag aagtccttgg ataagtactt gattttgatc   1500
aagaccaact ccaactacca caaggatatt tctttcgatg acttcgtcaa gttccaaatc   1560
aagtctaagc agtacaactt gtccaacaga atgactacca ttgctaacga ttggaactcc   1620
ttcattaagg gttctaacga attccacaac ttgatcgaat ctaaggatgg tgaaggtggt   1680
tcttcatctt ctaacagagg tattgattcc gccaatcaaa tcaacactac tactacctct   1740
accatcaacg atatcgaacc tttgttggtt ttcgttttct gtggtcaagg tccacaatgg   1800
aatggtatga ttaagacctt gtacaactcc gagaacgttt tcaagaacac cgttgatcat   1860
gttgacagca tcttgtacaa gtacttcggt tactccattt tgaacgtctt gtctaagatc   1920
gatgataacg acgattccat caaccatcca atagttgctc aaccatcttt gttcttgttg   1980
caaattggtt tggtcgagtt gtttaagtac tggggtatct acccatctat ctctgttggt   2040
cattctttcg gtgaagtctc ttcttattac ttgtccggta tcatctcttt ggaaaccgct   2100
tgtaaaatcg tctacgtcag atcctctaat cagaacaaaa ctatgggttc cggtaagatg   2160
ttggttgttt ctatgggttt taagcaatgg aacgatcaat tctctgctga atggtccgat   2220
attgaaattg cttgttacaa cgctccagat tccatagttg ttactggtaa cgaagaaaga   2280
ttgaaagaat tgtccatcaa gttgtccgac gaatccaatc aaattttcaa caccttcttg   2340
aggtccccat gttcttttca ttcttcccat caagaagtca tcaagggttc tatgttcgaa   2400
gagttgtcta acttgcaatc tactggtgaa accgaaatcc ctttgttctc tactgttact   2460
ggtagacaag ttttgtctgg tcatgttact gctcaacaca tctacgataa tgttagagaa   2520
ccagtcttgt tccaaaagac gattgaatcc attacctcct acatcaagtc tcactaccca   2580
tccaatcaaa aggttatcta cgttgaaatt gctccacacc caaccttgtt ttcattgatc   2640
aaaaagtcca tcccatcctc caacaagaat tcctcttctg ttttgtgtcc attgaacaga   2700
aaagaaaact ccaacaactc ctacaagaag ttcgtttctc agttgtactt caacggtgtt   2760
aacgttgact tcaacttcca gttgaactcc atttgcgata acgttaacaa cgatcaccat   2820
ttgaacaacg tcaagcaaaa ctccttcaaa gagactacca attccttgcc aagataccaa   2880
tgggaacaag atgaatattg gtccgaacca ttgatctcca gaaagaatag attggaaggt   2940
ccaactactt ccttgttggg tcatagaatt atctacagct tcccagtttt ccaatccgtt   3000
ttggacttgc aatctgacaa ctacaaatac ttgttggacc acttggttaa cggtaagcca   3060
gtttttccag gtgctggtta tttggatatc atcatcgaat tcttcgacta ccaaaagcag   3120
cagttgaatt cctctgattc ctctaactcc tacatcatca acgttgacaa gatccaattc   3180
ttgaacccaa ttcacttgac cgaaaacaag ttgcaaacct tgcaatcttc tttcgaacct   3240
atcgttacta agaagtctgc cttctctgtt aacttcttca tcaaggatac cgtcgaggat   3300
caatctaagg ttaagtctat gtctgacgaa acttggacta acacttgtaa ggctaccatt   3360
tccttggaac aacaacagcc atctccatct tctactttga ctttgtctaa gaagcaagac   3420
ttgcagatct tgagaaacag atgcgatatt agcaagctag acaagtttga gttgtacgac   3480
aagatctcta agaatttggg cttgcagtac aactccttgt ttcaagttgt tgataccatc   3540
```

```
gaaactggta aggattgctc ttttgctact ttgtctttgc cagaagatac tttgttcacc   3600
accattttga acccatgctt gttggataac tgtttccatg gtttgttgac cttgatcaac   3660
gaaaagggtt ctttcgttgt cgagtccatt tcttctgttt ctatctactt ggagaacatc   3720
ggttccttca atcaaacttc tgttggtaac gtccagttct acttgtacac cactatttct   3780
aaagccacct cctttagttc tgaaggtact tgtaagttgt tcaccaagga tggttccttg   3840
attttgtcta tcggtaagtt catcatcaag tccaccaatc caaagtctac taagaccaac   3900
gaaactatcg aatctccatt ggacgaaacc ttctctattg aatggcaatc taaggattct   3960
ccaattccaa ccccacaaca aatccaacaa caatctccat tgaactctaa cccatccttc   4020
attagatcta ccatcttgaa ggacatccag ttcgaacaat actgctcctc cattatccac   4080
aaagaattga tcaaccacga aaagtacaag aaccagcaat ccttcgatat caactccttg   4140
gaaaaccact tgaacgatga ccaattgatg gaatccttgt ccatctccaa agaatacttg   4200
agattcttca ccaggatcat ctccatcatt aagcaatacc caaagatctt gaacgaaaaa   4260
gagctaaaag aattgaaaga aatcatcgaa ttgaagtacc catccgaagt tcagttgttg   4320
gaattcgaag ttatcgagaa ggtgtccatg attatcccaa agttgttgtt cgaaaacgac   4380
aagcaatctt ccatgacctt gttccaagat aacttgttga ccaggttcta ctccaattct   4440
aactctacca gattctactt ggaaagggtt tccgaaatgg tcttggaatc tattagacca   4500
atcgtcagag aaaagagggt gttcagaatt ttggaaattg gtgctggtac aggctctttg   4560
tctaatgttg ttttgactaa gttgaacacc tacttgtcca ccttgaattc taatggtggt   4620
tctggttaca acatcatcat tgagtacacc ttcaccgata tttccgccaa cttcattatt   4680
ggtgaaatcc aagaaaccat gtgcaacttg tacccaaacg ttactttcaa gttctccgtc   4740
ttggacttgg agaaagagat tattaactcc tccgatttct tgatgggtga ttacgatata   4800
gttttgatgg cctacgttat ccatgccgtt tctaacatta agttctccat cgaacagttg   4860
tacaagttgt tgtctccaag aggttggttg ttgtgtattg aacctaagtc caacgttgtg   4920
ttctccgatt tggttttcgg ttgttttaat cagtggtgga actactacga tgatattaga   4980
actacccact gctccttgtc tgaatctcaa tggaatcagt tgttgttgaa ccagtccttg   5040
aacaacgaat cctcttcttc ttctaactgt tacggtggtt tctccaacgt ttcttttatt   5100
ggtggtgaaa aggatgtcga ctcccattct ttcatattgc actgccaaaa agaatccatc   5160
tcccaaatga agttagccac cactattaac aacggtttgt catctggttc catcgttatc   5220
gttttgaact ctcaacaatt gaccaacatg aagtcctacc caaaggttat tgagtatatt   5280
caagaggcta cctctttgtg caagaccatt gaaattatcg attccaagga cgtcttgaac   5340
tctaccaatt cagttttgga aaagatccaa aagtccttgt tggtgttctg tttgttgggt   5400
tatgacttgt tggagaacaa ctaccaagaa cagtctttcg aatacgttaa gttgttgaac   5460
ttgatctcta ctaccgcctc ttcatctaat gataagaaac caccaaaggt cttgttgatc   5520
accaagcaat ctgaaagaat ctccaggtct ttctactcca gatccttgat tggtatttcc   5580
agaacctcta tgaacgagta cccaaatttg tccattacct ctatcgattt ggataccaac   5640
gactactcat tgcagtcttt gttgaagcca atcttcagca actctaagtt ttccgacaac   5700
gagttcatct tcaaaaaggg cttgatgttc gtgtccagga tctttaagaa caagcagttg   5760
ctagaatcct ccaacgcttt tgaaactgac tcttctaact tgtactgtaa ggcctcttct   5820
gacttgtctt acaagtacgc tattaagcag tctatgttga ccgaaaatca gatcgaaatc   5880
```

```
aaggttgaat gcgtcggtat taacttcaag gacaacctat tctacaaggg cttgttgcca   5940
caagaaattt tcagaatggg tgacatctac aatccaccat atggtttgga atgctctggt   6000
gttattacca gaattggttc taacgtcacc gaatactcag ttggtcaaaa tgtttttggt   6060
ttcgccagac attctttggg ttctcatgtt gttaccaaca aggatttggt tatcttgaag   6120
ccagatacca tctcattttc tgaagctgct tctatcccag ttgtttactg tactgcttgg   6180
tactccttgt tcaacattgg tcagttgtct aacgaagaat ccatcctaat tcattctgct   6240
actggtggtg taggtttggc ttctttgaat ttgttgaaaa tgaagaatca gcaacagcaa   6300
ccattgacca atgtttatgc tactgttggc tctaacgaga agaagaagtt cttgatcgat   6360
aacttcaaca acttgttcaa agaggacggc gaaaacattt tctctaccag agacaaagaa   6420
tactccaacc agttggaatc caagatcgat gttattttga acaccttgtc cggtgaattc   6480
gtcgaatcta atttcaagtc cttgagatcc ttcggtagat tgattgattt gtctgctact   6540
cacgtttacg ccaatcaaca aattggtcta ggtaacttca agttcgacca cttgtattct   6600
gctgttgact tggaaagatt gatcgacgaa aaacctaagt tgttgcagtc catcttgcaa   6660
agaattacca actctatcgt caacggttcc ttggaaaaaa ttccaattac catcttccca   6720
tccaccgaaa ctaaggatgc tatcgaatta ttgtccaaga gatcccatat cggtaaagtt   6780
gttgtagatt gcaccgatat ctctaagtgt aatcctgttg gtgatgtgat caccaacttc   6840
tctatgagat tgccaaagcc aaactaccag ttgaatttga actccacctt gttgattact   6900
ggtcagtctg gtttgtctat ccctttgttg aattggttgt tgtctaagtc tggtggtaac   6960
gttaagaacg ttgtcatcat ttctaagtcc accatgaagt ggaagttgca gactatgatt   7020
tcccatttcg tttccggttt cggtatccat tttaactacg ttcaagtcga catctccaac   7080
tacgatgctt tgtctgaagc tattaagcaa ttgccatctg atttgccacc aatcacctct   7140
gtttttcatt tggctgctat ctacaacgat gttccaatgg atcaagttac catgtctacc   7200
gttgaatctg ttcataaccc taaagttttg ggtgccgtta acttgcatag aatctctgtt   7260
tcttttggtt ggaagttgaa ccacttcgtc ttgttctctt ctattactgc tattaccggt   7320
tacccagacc aatctatcta caattctgcc aactctattt tggacgcttt gtccaacttt   7380
agaaggttta tgggtttgcc atccttctcc attaacttgg gtccaatgaa ggatgaaggt   7440
aaggtttcta ccaacaagag catcaagaag ctattcaagt ctagaggttt gccaagccta   7500
tccttgaaca agttatttgg tttgttggag gtcgtcatca acaacccatc taatcatgtt   7560
atcccatccc aattgatttg ctccccaatc gatttcaaga cctacatcga atctttctca   7620
actatgaggc caaagttgtt acacttgcaa cctaccattt ccaagcagca atcttctatc   7680
attaacgatt ctaccaaggc ttcctccaac atttcattgc aagataagat cacctccaag   7740
gtgtctgatt tgttgtccat tccaatctcc aagatcaact tcgatcatcc attgaaacac   7800
tacggcttgg attctttgtt gaccgttcaa ttcaaatcct ggatcgacaa agaattcgaa   7860
aagaacttgt tcacccatat ccaattggcc accatctcta ttaactcatt cttggaaaag   7920
gtgaacggct tgtctacaaa caataacaac aacaacaatt ccaacgtcaa gtcctctcca   7980
tccattgtca aagaagaaat cgttaccttg gacaaggatc aacaaccatt gctattgaaa   8040
gaacaccagc acattatcat ctccccagat attagaatca acaagccaaa gagggaatcc   8100
ttgattagaa ccccaatctt gaacaaattc aaccagatca ccgaatccat tatcactcca   8160
tctacaccat ctttgtccca atccgatgtt ttgaaaactc caccaatcaa gtctttgaac   8220
aacactaaga actccagctt gattaacacc ccaccaattc aatctgtcca acaacatcaa   8280
```

```
aagcaacaac aaaaggtcca agtcatccaa caacagcaac aaccattatc cagattgtcc   8340

tacaagagca acaacaactc tttcgttttg ggtatcggta tttctgttcc aggtgaacct   8400

atttcccaac aatccttgaa agactccatc tccaatgact tttctgataa ggctgaaact   8460

aacgagaagg tcaagagaat ctttgagcaa tctcaaatca agaccagaca cttggttaga   8520

gattacacta agccagagaa ctccatcaag ttcagacatt tggaaaccat taccgatgtg   8580

aacaaccagt tcaagaaagt tgttccagat ttggctcaac aagcctgttt gagagctttg   8640

aaagattggg gtggtgataa gggtgatatt acccatatag tttctgttac ctccaccggt   8700

attatcatcc cagatgttaa tttcaagttg atcgacttgt tgggcttgaa caaggatgtt   8760

gaaagagtgt ctttgaacct aatgggttgt ttggctggtt tgagttcttt gagaactgct   8820

gcttctttgg ctaaggcttc tccaagaaat agaattttgg ttgtctgtac cgaagtctgc   8880

tccttgcatt tttctaatac tgatggtggt gatcaaatgg tcgcctcttc tatttttgct   8940

gatggttctg ctgcttacat tattggttgt aacccaagaa ttgaagaaac cccattatac   9000

gaagtcatgt gctccattaa cagatctttc ccaaataccg aaaacgccat ggtttgggat   9060

ttggaaaaag aaggttggaa cttgggtttg gatgcttcta ttccaattgt cattggttct   9120

ggtattgaag ccttcgttga tactttgttg gataaggcta agttgcaaac ttccactgct   9180

atttctgcta aggattgcga attcttgatt catactggtg gcaagtccat cttgatgaac   9240

atcgaaaatt ccttgggtat cgacccaaag caaactaaga atacttggga tgtttaccat   9300

gcctacggca atatgtcatc tgcctctgtt attttcgtta tggatcatgc cagaaagtcc   9360

aagtctttgc caacttactc aatttctttg gcttttggtc caggtttggc ttttgaaggt   9420

tgtttcttga agaacgtcgt ctaa                                          9444
```

<210> SEQ ID NO 2
<211> LENGTH: 14025
<212> TYPE: DNA
<213> ORGANISM: Artificial Sequence
<220> FEATURE:
<223> OTHER INFORMATION: Plasmid
<220> FEATURE:
<221> NAME/KEY: C1:p506 primer homology
<222> LOCATION: (1)..(50)
<220> FEATURE:
<221> NAME/KEY: 19 UP
<222> LOCATION: (51)..(761)
<220> FEATURE:
<221> NAME/KEY: L0
<222> LOCATION: (762)..(800)
<220> FEATURE:
<221> NAME/KEY: THD3p
<222> LOCATION: (801)..(1453)
<220> FEATURE:
<221> NAME/KEY: L1
<222> LOCATION: (1454)..(1493)
<220> FEATURE:
<221> NAME/KEY: ALD6
<222> LOCATION: (1494)..(2999)
<220> FEATURE:
<221> NAME/KEY: L2
<222> LOCATION: (3000)..(3039)
<220> FEATURE:
<221> NAME/KEY: LTP1
<222> LOCATION: (3364)..(3403)
<220> FEATURE:
<221> NAME/KEY: Tef1p
<222> LOCATION: (3404)..(3897)
<220> FEATURE:
<221> NAME/KEY: L3
<222> LOCATION: (3898)..(3937)
<220> FEATURE:

<221> NAME/KEY: Acs L641P
<222> LOCATION: (3938)..(5893)
<220> FEATURE:
<221> NAME/KEY: L4
<222> LOCATION: (5894)..(5933)
<220> FEATURE:
<221> NAME/KEY: PRM9t
<222> LOCATION: (5934)..(6471)
<220> FEATURE:
<221> NAME/KEY: LTP2
<222> LOCATION: (6472)..(6511)

<400> SEQUENCE: 2

```
taaccctcac taaagggaac aaaagctgga gctcgtttaa acggcgcgcc caccggagct     60

tggatatgat aaacgaaata ttcttgaatc gtgagatcgc ctgttttcaa aaccgttgga    120

ggcagaaaca attttgtcac aagatgggca ttctacccca tccttgctgt attattgtag    180

tctcgctttc ttttatgctg gacaaatgag actactgcac atttttatac gttcttggtt    240

tttttaaag gtgtggtttc ggcattatcc tgccgcacgt ttcttggata attcatcctg    300

attctctatt ttaaacgctt cagcctatca ggatttggtt ttgatacata ctgcaagagt    360

gtatctcggg aacagtcatt tattccgcaa caaacttaat tgcggaacgc gttaggcgat    420

ttctagcata tatcaaatac cgttcgcgat ttcttctggg ttcgtctctt ttcttttaaa    480

tacttattaa cgtactcaaa caactacact tcgttgtatc tcagaatgag atccctcagt    540

atgacaatac atcattctaa acgttcgtaa aacacatatg aaacaacttt ataacaaagc    600

gaacaaaatg ggcaacatga gatgaaactc cgcgtccctt agctgaacta cccaaacgta    660

cgaatgcctg aacaattagt ttagatccga gattccgcgc ttccatcatt tagtataatc    720

catattttat ataatatata ggataagtaa cagcccgcga aaaacaacaa ataatcataa    780

aaattttaga actagacata tcgagtttat cattatcaat actgccattt caaagaatac    840

gtaaataatt aatagtagtg attttcctaa ctttatttag tcaaaaaatt agccttttaa    900

ttctgctgta acccgtacat gcccaaaata gggggcgggt tacacagaat atataacatc    960

gtaggtgtct gggtgaacag tttattcctg gcatccacta aatataatgg agcccgcttt   1020

ttaagctggc atccagaaaa aaaaagaatc ccagcaccaa aatattgttt tcttcaccaa   1080

ccatcagttc ataggtccat tctcttagcg caactacaga gaacaggggc acaaacaggc   1140

aaaaaacggg cacaacctca atggagtgat gcaacctgcc tggagtaaat gatgacacaa   1200

ggcaattgac ccacgcatgt atctatctca ttttcttaca ccttctatta ccttctgctc   1260

tctctgattt ggaaaaagct gaaaaaaaag gttgaaacca gttccctgaa attattcccc   1320

tacttgacta ataagtatat aaagacggta ggtattgatt gtaattctgt aaatctattt   1380

cttaaacttc ttaaattcta cttttatagt tagtcttttt tttagtttta aaacaccaag   1440

aacttagttt cgactagaaa atttattata aaaggaagag aaataattaa acaatgacta   1500

agctacactt tgacactgct gaaccagtca agatcacact tccaaatggt ttgacatacg   1560

agcaaccaac cggtctattc attaacaaca agtttatgaa agctcaagac ggtaagacct   1620

atcccgtcga agatccttcc actgaaaaca ccgtttgtga ggtctcttct gccaccactg   1680

aagatgttga atatgctatc gaatgtgccg accgtgcttt ccacgacact gaatgggcta   1740

cccaagaccc aagagaaaga ggccgtctac taagtaagtt ggctgacgaa ttggaaagcc   1800

aaattgactt ggtttcttcc attgaagctt tggacaatgg taaaactttg gccttagccc   1860

gtggggatgt taccattgca atcaactgtc taagagatgc tgctgcctat gccgacaaag   1920

tcaacggtag aacaatcaac accggtgacg gctacatgaa cttcaccacc ttagagccaa   1980
```

```
tcggtgtctg tggtcaaatt attccatgga actttccaat aatgatgttg gcttggaaga   2040
tcgccccagc attggccatg ggtaacgtct gtatcttgaa acccgctgct gtcacacctt   2100
taaatgccct atactttgct tctttatgta agaaggttgg tattccagct ggtgtcgtca   2160
acatcgttcc aggtcctggt agaactgttg gtgctgcttt gaccaacgac ccaagaatca   2220
gaaagctggc ttttaccggt tctacagaag tcggtaagag tgttgctgtc gactcttctg   2280
aatctaactt gaagaaaatc actttggaac taggtggtaa gtccgcccat ttggtctttg   2340
acgatgctaa cattaagaag actttaccaa atctagtaaa cggtattttc aagaacgctg   2400
gtcaaatttg ttcctctggt tctagaattt acgttcaaga aggtatttac gacgaactat   2460
tggctgcttt caaggcttac ttggaaaccg aaatcaaagt tggtaatcca tttgacaagg   2520
ctaacttcca aggtgctatc actaaccgtc aacaattcga cacaattatg aactacatcg   2580
atatcggtaa gaaagaaggc gccaagatct taactggtgg cgaaaaagtt ggtgacaagg   2640
gttacttcat cagaccaacc gttttctacg atgttaatga agacatgaga attgttaagg   2700
aagaaatttt tggaccagtt gtcactgtcg caaagttcaa gactttagaa gaaggtgtcg   2760
aaatggctaa cagctctgaa ttcggtctag gttctatggg tatcgaaaca gaatctttga   2820
gcacaggttt gaaggtggcc aagatgttga aggccggtac cgtctggatc aacacataca   2880
acgattttga ctccagagtt ccattcggtg gtgttaagca atctggttac ggtagagaaa   2940
tgggtgaaga agtctaccat gcatacactg aagtaaaagc tgtcagaatt aagttgtaaa   3000
gacataaaac tgaaacaaca ccaattaata atagactttt ggacttcttc gccagaggtt   3060
tggtcaagtc tccaatcaag gttgtcggct tgtctacctt gccagaaatt tacgaaaaga   3120
tggaaaaggg tcaaatcgtt ggtagatacg ttgttgacac ttctaaataa gcgaatttct   3180
tatgatttat gatttttatt attaaataag ttataaaaaa aataagtgta tacaaatttt   3240
aaagtgactc ttaggtttta aaacgaaaat tcttattctt gagtaactct ttcctgtagg   3300
tcaggttgct ttctcaggta tagcatgagg tcgctcttat tgaccacacc tctaccggca   3360
tggcttaaat aacatactca tcactaaaca ttcttaacaa tcaaagcaac aggcgcgttg   3420
gacttttaat tttcgaggac cgcgaatcct tacatcacac ccaatccccc acaagtgatc   3480
ccccacacac catagcttca aaatgtttct actccttttt tactcttcca gattttctcg   3540
gactccgcgc atcgccgtac cacttcaaaa cacccaagca cagcatacta aatttcccct   3600
ctttcttcct ctagggtgtc gttaattacc cgtactaaag gtttggaaaa gaaaaaagag   3660
accgcctcgt ttctttttct tcgtcgaaaa aggcaataaa aatttttatc acgtttcttt   3720
ttcttgaaaa tttttttttt tgattttttt ctctttcgat gacctcccat tgatatttaa   3780
gttaataaac ggtcttcaat ttctcaagtt tcagtttcat ttttcttgtt ctattacaac   3840
tttttttact tcttgctcat tagaaagaaa gcatagcaat ctaatctaag ttttaataca   3900
tctaccagtc aacagccaac aattaactaa ttaaacaatg tcccaaactc ataagcacgc   3960
tattccagct aatattgctg atagatgctt gatcaaccca gaacagtacg aaactaagta   4020
caagcaatcc atcaacgatc cagatacttt ttggggtgaa caaggtaaga ttttggattg   4080
gattacccca taccaaaagg tcaagaatac ttcttttgct ccaggcaacg tttccattaa   4140
gtggtatgaa gatggtactt tgaacttggc tgctaactgt ttggatagac acttgcaaga   4200
aaacggtgat agaaccgcta ttatttggga aggtgatgat acctcccaat ccaaacatat   4260
ctcttacaga gaattgcaca gagatgtctg tagattcgct aacactttgt tggatttggg   4320
```

-continued

```
catcaaaaag ggtgatgttg ttgctatcta tatgccaatg gttcctgaag ctgctgttgc   4380
tatgttggct tgtgctagaa ttggtgctgt tcattctgtt attttcggtg gtttttcacc   4440
agaagctgtt gccggtagaa ttatcgattc ttcatccaga ttggttatca ccgctgatga   4500
aggtgttaga gctggtagat ctattccatt gaaaaagaac gttgatgacg ccttgaagaa   4560
cccaaatgtt acttctgttg aacacgtcat cgttttgaag agaactggtt ctgatatcga   4620
ttggcaagag ggtagagatt tgtggtggag agatttgatt gaaaaggctt ctccagaaca   4680
tcaaccagaa gctatgaacg ctgaagatcc tttgtttatc ttgtacactt ctggttctac   4740
tggtaagcca aaaggtgttt tacacactac tggtggttat ttggtttacg ctgctactac   4800
tttcaagtac gttttcgatt atcacccagg tgatatctat tggtgtactg ctgatgttgg   4860
ttgggttact ggtcattctt atttgttgta tggtccattg gcttgtggtg ctactacatt   4920
gatgtttgaa ggtgttccaa attggccaac tccagctaga atgtgtcaag ttgttgacaa   4980
acaccaagtc aacatcttgt atactgctcc aactgctatt agagctttga tggctgaagg   5040
tgataaggct attgaaggta ctgatagatc ctccttgaga atcttgggtt ctgttggtga   5100
acctattaac cctgaagcct gggaatggta ttggaagaaa attggtaaag aaaagtgccc   5160
agttgttgat acttggtggc aaactgaaac tggtggtttt atgattactc cattgccagg   5220
tgctattgaa ttgaaagctg gttctgctac tagaccattt tttggtgttc aaccagcttt   5280
ggttgataac gaaggtcatc cacaagaagg tgctactgaa ggtaatttgg ttattactga   5340
ttcttggcca ggtcaagcta gaactttgtt tggtgatcac gaaagattcg aacagactta   5400
cttctctacc ttcaagaaca tgtacttctc tggtgatggt gctagaagag atgaagatgg   5460
ttactattgg attaccggta gagttgatga tgtcttgaat gtttctggtc acagattagg   5520
tactgccgaa attgaatctg ctttggttgc tcatccaaag attgctgaag ctgcagttgt   5580
tggtattcca catgctatta agggtcaagc tatctacgct tacgttactt tgaatcatgg   5640
tgaagaacca tctccagaat tatacgctga agttagaaac tgggtcagaa aagaaattgg   5700
tccattagct accccagatg ttttacattg gactgattct ttgccaaaga ccagatcagg   5760
taagatcatg agaagaatct tgagaaagat tgctgctggt gatacttcta acttgggtga   5820
tacttcaaca ttagctgatc caggtgttgt tgaaaagcct ttggaagaaa aacaagctat   5880
tgccatgcca tcctaataat taaatactat tttcaaaatt ctacttaaaa ataacagaag   5940
acgggagaca ctagcacaca actttaccag gcaaggtatt tgacgctagc atgtgtccaa   6000
ttcagtgtca tttatgattt tttgtagtag gatataaata tatacagcgc tccaaatagt   6060
gcggttgccc caaaaacacc acggaacctc atctgttctc gtactttgtt gtgacaaagt   6120
agctcactgc cttattatca cattttcatt atgcaacgct tcggaaaata cgatgttgaa   6180
aatgcctcta gagatgaaaa acaatcgtaa aagggtcctg cgtaattgaa acatttgatc   6240
agtatgcagt ggcacagaaa caaccaggaa tactatagtc ataggcaata caaggtatat   6300
attggctatg cagacccctc cagaaagtac cgacgtcaag ttagatacac ttaacgaacc   6360
tagtgcacat ttaattgaga aaaatgtggc tcttcctaag gacatattcc gttcgtactt   6420
gagttattgg atctatgaaa tcgctcgcta tacaccagtc atgattttgt cattgcgaag   6480
actatactga tatatgaatt taaactagag cggaccaact atcatccgct aattactgac   6540
attaccaaat gagatctgtg aatgggcaag ataaaaaaca aaaattgaaa tgtttgacgt   6600
tatgtaaaac tattaattcc ttcgctttcg gcggtcacag aatttgcgtg tagctgactc   6660
ttgttcaatc aatatcattt gttactttat ttgaaagtct gtattactgc gcctattgtc   6720
```

```
atccgtacca aagaacgtca aaaagaaaca agataatttt tgtgcttaca ccatttatag   6780
atcactgagc ccagaatatc gctggagctc agtgtaagtg gcatgaacac aactctgact   6840
gatcgcacat attgccgtta tcataaatac tagttgtact tgtcaatgcg acgaatggca   6900
tcatgcctat tattacgttc ctctttttcc gtttcatgtt tccagaatgc tattgaatct   6960
aacacttcaa ttataaaaaa gaataaatcc gcaataattt taggctaatt gttgtactgt   7020
caagcgaacc taatggttaa aattcagagg aaccttcgac gtagtctgat cgctacttct   7080
atatcttatg ttcccagtca atcaaaagtt gatactataa tagctgccat ttatacctgt   7140
tagttatggc gatcgtttat cacggcggcc gcggtaccta ataacttcgt atagcataca   7200
ttatacgaag ttatattaag ggttctcgac gttttcgaca ctggatggcg gcgttagtat   7260
cgaatcgaca gcagtatagc gaccagcatt cacatacgat tgacgcatga tattactttc   7320
tgcgcactta acttcgcatc tgggcagatg atgtcgaggc gaaaaaaaat ataaatcacg   7380
ctaacatttg attaaaatag aacaactaca atataaaaaa actatacaaa tgacaagttc   7440
ttgaaaacaa gaatcttttt attgtcagta ctgattagaa aaactcatcg agcatcaaat   7500
gaaactgcaa tttattcata tcaggattat caataccata tttttgaaaa agccgtttct   7560
gtaatgaagg agaaaactca ccgaggcagt tccataggat ggcaagatcc tggtatcggt   7620
ctgcgattcc gactcgtcca acatcaatac aacctattaa tttcccctcg tcaaaaataa   7680
ggttatcaag tgagaaatca ccatgagtga cgactgaatc cggtgagaat ggcaaaagct   7740
tatgcatttc tttccagact tgttcaacag gccagccatt acgctcgtca tcaaaatcac   7800
tcgcatcaac caaaccgtta ttcattcgtg attgcgcctg agcgagacga aatacgcgat   7860
cgctgttaaa aggacaatta caaacaggaa tcgaatgcaa ccggcgcagg aacactgcca   7920
gcgcatcaac aatattttca cctgaatcag gatattcttc taatacctgg aatgctgttt   7980
tgccggggat cgcagtggtg agtaaccatg catcatcagg agtacggata aaatgcttga   8040
tggtcggaag aggcataaat tccgtcagcc agtttagtct gaccatctca tctgtaacat   8100
cattggcaac gctacctttg ccatgtttca gaaacaactc tggcgcatcg ggcttcccat   8160
acaatcgata gattgtcgca cctgattgcc cgacattatc gcgagcccat ttatacccat   8220
ataaatcagc atccatgttg gaatttaatc gcggcctcga aacgtgagtc ttttccttac   8280
ccatggttgt ttatgttcgg atgtgatgtg agaactgtat cctagcaaga ttttaaaagg   8340
aagtatatga aagaagaacc tcagtggcaa atcctaacct tttatatttc tctacagggg   8400
cgcggcgtgg ggacaattca acgcgtctgt gaggggagcg tttccctgct cgcaggtctg   8460
cagcgaggag ccgtaatttt tgcttcgcgc cgtgcggcca tcaaaatgta tggatgcaaa   8520
tgattataca tggggatgta tgggctaaat gtacgggcga cagtcacatc atgcccctga   8580
gctgcgcacg tcaagactgt caaggagggt attctgggcc tccatgtcgc tggccgggtg   8640
acccggcggg gacgaggcaa gctaaacaga tctctagacc taataacttc gtatagcata   8700
cattatacga agttatatta agggttgtct taattaaggg tgcccaattc gccctatagt   8760
gagtcgtatt acgcgcgctc actggccgtc gttttacaac gtcgtgactg ggaaaaccct   8820
ggcgttaccc aacttaatcg ccttgcagca catccccctt tcgccagctg gcgtaatagc   8880
gaagaggccc gcaccgatcg cccttcccaa cagttgcgca gcctgaatgg cgaatggcgc   8940
gacgcgccct gtagcggcgc attaagcgcg gcgggtgtgg tggttacgcg cagcgtgacc   9000
gctacacttg ccagcgccct agcgcccgct cctttcgctt tcttcccttc ctttctcgcc   9060
```

-continued

```
acgttcgccg gctttccccg tcaagctcta aatcgggggc tccctttagg gttccgattt   9120
agtgctttac ggcacctcga ccccaaaaaa cttgattagg gtgatggttc acgtagtggg   9180
ccatcgccct gatagacggt ttttcgccct ttgacgttgg agtccacgtt ctttaatagt   9240
ggactcttgt tccaaactgg aacaacactc aaccctatct cggtctattc ttttgattta   9300
taagggattt tgccgatttc ggcctattgg ttaaaaaatg agctgattta acaaaaattt   9360
aacgcgaatt ttaacaaaat attaacgttt acaatttcct gatgcggtat tttctcctta   9420
cgcatctgtg cggtatttca caccgcatag atccgtcgag ttcaagagaa aaaaaaagaa   9480
aaagcaaaaa gaaaaaagga aagcgcgcct cgttcagaat gacacgtata gaatgatgca   9540
ttaccttgtc atcttcagta tcatactgtt cgtatacata cttactgaca ttcataggta   9600
tacatatata cacatgtata tatatcgtat gctgcagctt taaataatcg gtgtcaatgt   9660
ctgcccctat gtctgcccct aagaagatcg tcgttttgcc aggtgaccac gttggtcaag   9720
aaatcacagc cgaagccatt aaggttctta aagctatttc tgatgttcgt tccaatgtca   9780
agttcgattt cgaaaatcat ttaattggtg gtgctgctat cgatgctaca ggtgtcccac   9840
ttccagatga ggcgctggaa gcctccaaga aggttgatgc cgttttgtta ggtgctgtgg   9900
gtggtcctaa atggggtgcc ggtagtgtta gacctgaaca aggtttacta aaaatccgta   9960
aagaacttca attgtacgcc aacttaagac catgtaactt tgcatccgac tctcttttag  10020
acttatctcc aatcaagcca caatttgcta aaggtactga cttcgttgtt gtcagagaat  10080
tagtgggagg tatttacttt ggtaagagaa aggaagacga tggtgatggt gtcgcttggg  10140
atagtgaaca atacaccgtt ccagaagtgc aaagaatcac aagaatggcc gctttcatgg  10200
ccctacaaca tgagccacca ttgcctattt ggtccttgga taaagctaat gttttggcct  10260
cttcaagatt atggagaaaa actgtggagg aaaccatcaa gaacgaattc cctacattga  10320
aggttcaaca tcaattgatt gattctgccg ccatgatcct agttaagaac ccaacccacc  10380
taaatggtat tataatcacc agcaacatgt ttggtgatat catctccgat gaagcctccg  10440
ttatcccagg ttccttgggt ttgttgccat ctgcgtcctt ggcctctttg ccagacaaga  10500
acaccgcatt tggtttgtac gaaccatgcc acggttctgc tccagatttg ccaaagaata  10560
aggttgaccc tatcgccact atcttgtctg ctgcaatgat gttgaaattg tcattgaact  10620
tgcctgaaga aggtaaggcc attgaagatg cagttaaaaa ggttttggat gcaggtatca  10680
gaactggtga tttaggtggt tccaacagta ccaccgaagt cggtgatgct gtcgccgaag  10740
aagttaagaa aatccttgct taactttgcc ttcgtttatc ttgcctgctc atttttttagt  10800
atattcttcg aagaaatcac attactttat ataatgtata attcattatg tgataatgcc  10860
aatcgctaag aaaaaaaaag agtcatccgc taggggaaaa aaaaaaatga aaatcattac  10920
cgaggcataa aaaaatatag agtgtactag aggaggccaa gagtaataga aaaagaaaat  10980
tgcgggaaag gactgtgtta tgacttccct gactaatgcc gtgttcaaac gatacctggc  11040
agtgactcct agcgctcacc aagctcttaa aacgggaatt tatggtgcac tctcagtaca  11100
atctgctctg atgccgcata gttaagccag ccccgacacc cgccaacacg cgctgacgcg  11160
ccctgacggg cttgtctgct cccggcatcc gcttacagac aagctgtgac cgtctccggg  11220
agctgcatgt gtcagaggtt ttcaccgtca tcaccgaaac gcgcgagacg aaagggcctc  11280
gtgatacgcc tatttttata ggttaatgtc atgataataa tggtttctta ggacggatcg  11340
cttgcctgta acttacacgc gcctcgtatc ttttaatgat ggaataattt gggaatttac  11400
tctgtgttta tttattttta tgttttgtat ttggatttta gaaagtaaat aaagaaggta  11460
```

```
gaagagttac ggaatgaaga aaaaaaaata aacaaaggtt taaaaaattt caacaaaaag  11520
cgtactttac atatatattt attagacaag aaaagcagat taaatagata tacattcgat  11580
taacgataag taaaatgtaa aatcacagga ttttcgtgtg tggtcttcta cacagacaag  11640
atgaaacaat tcggcattaa tacctgagag caggaagagc aagataaaag gtagtatttg  11700
ttggcgatcc ccctagagtc ttttacatct tcggaaaaca aaaactattt tttctttaat  11760
ttcttttttt actttctatt tttaatttat atatttatat taaaaaattt aaattataat  11820
tatttttata gcacgtgatg aaaaggaccc aggtggcact tttcggggaa atgtgcgcgg  11880
aacccctatt tgtttatttt tctaaataca ttcaaatatg tatccgctca tgagacaata  11940
accctgataa atgcttcaat aatattgaaa aaggaagagt atgagtattc aacatttccg  12000
tgtcgccctt attccctttt ttgcggcatt ttgccttcct gtttttgctc acccagaaac  12060
gctggtgaaa gtaaaagatg ctgaagatca gttgggtgca cgagtgggtt acatcgaact  12120
ggatctcaac agcggtaaga tccttgagag ttttcgcccc gaagaacgtt ttccaatgat  12180
gagcactttt aaagttctgc tatgtggcgc ggtattatcc cgtattgacg ccgggcaaga  12240
gcaactcggt cgccgcatac actattctca gaatgacttg gttgagtact caccagtcac  12300
agaaaagcat cttacggatg gcatgacagt aagagaatta tgcagtgctg ccataaccat  12360
gagtgataac actgcggcca acttacttct gacaacgatc ggaggaccga aggagctaac  12420
cgcttttttg cacaacatgg gggatcatgt aactcgcctt gatcgttggg aaccggagct  12480
gaatgaagcc ataccaaacg acgagcgtga caccacgatg cctgtagcaa tggcaacaac  12540
gttgcgcaaa ctattaactg gcgaactact tactctagct tcccggcaac aattaataga  12600
ctggatggag gcggataaag ttgcaggacc acttctgcgc tcggcccttc cggctggctg  12660
gtttattgct gataaatctg gagccggtga gcgtgggtct cgcggtatca ttgcagcact  12720
ggggccagat ggtaagccct cccgtatcgt agttatctac acgacgggga gtcaggcaac  12780
tatggatgaa cgaaatagac agatcgctga gataggtgcc tcactgatta agcattggta  12840
actgtcagac caagtttact catatatact ttagattgat ttaaaacttc atttttaatt  12900
taaaaggatc taggtgaaga tcctttttga taatctcatg accaaaatcc cttaacgtga  12960
gttttcgttc cactgagcgt cagaccccgt agaaaagatc aaaggatctt cttgagatcc  13020
tttttttctg cgcgtaatct gctgcttgca aacaaaaaaa ccaccgctac cagcggtggt  13080
ttgtttgccg gatcaagagc taccaactct ttttccgaag gtaactggct tcagcagagc  13140
gcagatacca aatactgtcc ttctagtgta gccgtagtta ggccaccact tcaagaactc  13200
tgtagcaccg cctacatacc tcgctctgct aatcctgtta ccagtggctg ctgccagtgg  13260
cgataagtcg tgtcttaccg ggttggactc aagacgatag ttaccggata aggcgcagcg  13320
gtcgggctga acggggggtt cgtgcacaca gcccagcttg gagcgaacga cctacaccga  13380
actgagatac ctacagcgtg agctatgaga aagcgccacg cttcccgaag ggagaaaggc  13440
ggacaggtat ccggtaagcg gcagggtcgg aacaggagag cgcacgaggg agcttccagg  13500
gggaaacgcc tggtatcttt atagtcctgt cgggtttcgc cacctctgac ttgagcgtcg  13560
atttttgtga tgctcgtcag gggggcggag cctatggaaa aacgccagca acgcggcctt  13620
tttacggttc ctggcctttt gctggccttt tgctcacatg ttctttcctg cgttatcccc  13680
tgattctgtg gataaccgta ttaccgcctt tgagtgagct gataccgctc gccgcagccg  13740
aacgaccgag cgcagcgagt cagtgagcga ggaagcggaa gagcgcccaa tacgcaaacc  13800
```

```
gcctctcccc gcgcgttggc cgattcatta atgcagctgg cacgacaggt ttcccgactg  13860

gaaagcgggc agtgagcgca acgcaattaa tgtgagttac ctcactcatt aggcacccca  13920

ggctttacac tttatgcttc cggctcctat gttgtgtgga attgtgagcg gataacaatt  13980

tcacacagga aacagctatg accatgatta cgccaagcgc gcaat                  14025
```

<210> SEQ ID NO 3
<211> LENGTH: 684
<212> TYPE: DNA
<213> ORGANISM: Saccharomyces cerevisiae
<220> FEATURE:
<221> NAME/KEY: Acc1 promoter
<222> LOCATION: (1)..(463)
<220> FEATURE:
<221> NAME/KEY: gRNA_3
<222> LOCATION: (53)..(72)
<220> FEATURE:
<221> NAME/KEY: gRNA_2
<222> LOCATION: (265)..(284)
<220> FEATURE:
<221> NAME/KEY: gRNA_1
<222> LOCATION: (339)..(358)

<400> SEQUENCE: 3

```
ggtagaaact tgatttttc taattttctg cgctgtttcg ggaacggaaa aaaattaagc     60

tagaagacga atcggttatt atactattat atttgtatag tatagtagcg tgtcgtatcg    120

tatcgtgtcg tatcgtatcg tatcgttaaa agaaaataca cgaataaata ataatatgtg    180

gagaagaaaa agggaagttt cttgtctctt gctctgaatc tgaattccaa ttcaagttca    240

aattgttctc tagtttattg tccaaaaata aggatgaagc gggagggaag ggcagaggga    300

aaagttcgta tagtagaatg aataaacttt tataaacaca tgcaccgatc actcacagag    360

gataaaaaaa tggcacaaca aatatatata tatagatgca aatggcgatt gcaaattagg    420

gaattggctt tgttgttttt tatcttcagg taaactgtac gaaagggata aaaagagtag    480

aataaggaaa ggaaaattga agagagcaga acaattgtag aaccgataac aattgtgaca    540

gtgattgtgc taggctatac tgtgccagaa tacgactggg agtgctgttc ttcttatata    600

tcttggcgct gattgagcgt atagcctagt tcaccaagca gtagagagag tggcaatgag    660

cggttgaatt tcgactgcga cttg                                           684
```

<210> SEQ ID NO 4
<211> LENGTH: 971
<212> TYPE: DNA
<213> ORGANISM: Artificial Sequence
<220> FEATURE:
<223> OTHER INFORMATION: PGK1 promoter and integration sequences for
Saccharomyces cerevisiae Acc1 promoter
<220> FEATURE:
<221> NAME/KEY: PGK1p
<222> LOCATION: (7)..(750)

<400> SEQUENCE: 4

```
tgttttatat ttgttgtaaa aagtagataa ttacttcctt gatgatctgt aaaaaagaga     60

aaaagaaagc atctaagaac ttgaaaaact acgaattaga aaagaccaaa tatgtatttc    120

ttgcattgac caatttatgc aagtttatat atatgtaaat gtaagtttca cgaggttcta    180

ctaaactaaa ccacccccctt ggttagaaga aaagagtgtg tgagaacagg ctgttgttgt    240

cacacgattc ggacaattct gtttgaaaga gagagagtaa cagtacgatc gaacgaactt    300

tgctctggag atcacagtgg gcatcatagc atgtggtact aaaccctttc ccgccattcc    360

agaaccttcg attgcttgtt acaaaacctg tgagccgtcg ctaggacctt gttgtgtgac    420
```

```
gaaattggaa gctgcaatca ataggaagac aggaagtcga gcgtgtctgg gtttttttcag    480

ttttgttctt tttgcaaaca aatcacgagc gacggtaatt tctttctcga taagaggcca    540

cgtgctttat gagggtaaca tcaattcaag aaggagggaa acacttcctt tttctggccc    600

tgataatagt atgagggtga agccaaaata aaggattcgc gcccaaatcg gcatctttaa    660

atgcaggtat gcgatagttc ctcactcttt ccttactcac gagtaattct tgcaaatgcc    720

tattatgcag atgttataat atctgtgcgt agggataaaa agagtagaat aaggaaagga    780

aaattgaaga gagcagaaca attgtagaac cgataacaat tgtgacagtg attgtgctag    840

gctatactgt gccagaatac gactgggagt gctgttcttc ttatatatct tggcgctgat    900

tgagcgtata gcctagttca ccaagcagta gagagagtgg caatgagcgg ttgaatttcg    960

actgcgactt g                                                        971


<210> SEQ ID NO 5
<211> LENGTH: 1724
<212> TYPE: DNA
<213> ORGANISM: Artificial Sequence
<220> FEATURE:
<223> OTHER INFORMATION: Cassette with Saccharomyces cerevisiae Acc1
      (S659A; S1167A) coding sequence, regulatory sequences and
      integration sequences
<220> FEATURE:
<221> NAME/KEY: T-G Ser659Ala
<222> LOCATION: (108)..(108)
<220> FEATURE:
<221> NAME/KEY: T-G ser1167ala
<222> LOCATION: (1602)..(1602)

<400> SEQUENCE: 5

ggcgcgccga gggtaaaaga tacaagttca cggtcgctaa atccggtaat gaccgctaca     60

cattatttat caatggttct aaatgtgata tcatactgcg tcaactagct gatggtgggc    120

tgctgatcgc tatcggcgct aaatcgcata ccatctattg gaaagaagaa gttgctgcta    180

caagattatc cgttgactct atgactactt tgttggaagt tgaaaacgat ccaacccagt    240

tgcgtactcc atcccctggt aaattggtta aattcttggt ggaaaatggt gaacacatta    300

tcaagggcca accatatgca gaaattgaag ttatgaaaat gcaaatgcct ttggtttctc    360

aagaaaatgg tatcgtccag ttattaaagc aacctggttc taccattgtt gcaggtgata    420

tcatggctat tatgactctt gacgatccat ccaaggtcaa gcacgctcta ccatttgaag    480

gtatgctgcc agattttggt tctccagtta tcgaaggaac caaacctgcc tataaattca    540

agtcattagt gtctactttg gaaaacattt tgaagggtta tgacaaccaa gttattatga    600

acgcttcctt gcaacaattg atagaagttt tgagaaatcc aaaactgcct tactcagaat    660

ggaaactaca catctctgct ttacattcaa gattgcctgc taagctagat gaacaaatgg    720

aagagttagt tgcacgttct ttgagacgtg gtgctgtttt cccagctaga caattaagta    780

aattgattga tatggccgtg aagaatcctg aatacaaccc cgacaaattg ctgggcgcag    840

tcgtggaacc attggcggat attgctcata agtactctaa cgggttagaa gcccatgaac    900

attctatatt tgtccatttc ttggaagaat attacgaagt tgaaaagtta ttcaatggtc    960

caaatgttcg tgaggaaaat atcattctga aattgcgtga tgaaaaccct aaagatctag   1020

ataaagttgc gctaactgtt ttgtctcatt cgaaagtttc agcgaagaat aacctgatcc   1080

tagctatctt gaaacattat caaccattgt gcaagttatc ttctaaagtt tctgccattt   1140

tctctactcc tctacaacat attgttgaac tagaatctaa ggctaccgct aaggtcgctc   1200
```

```
tacaagcaag agaaattttg attcaaggcg ctttaccttc ggtcaaggaa agaactgaac   1260

aaattgaaca tatcttaaaa tcctctgttg tgaaggttgc ctatggctca tccaatccaa   1320

agcgctctga accagatttg aatatcttga aggacttgat cgattctaat tacgttgtgt   1380

tcgatgtttt acttcaattc ctaacccatc aagacccagt tgtgactgct gcagctgctc   1440

aagtctatat tcgtcgtgct tatcgtgctt acaccatagg agatattaga gttcacgaag   1500

gtgtcacagt tccaattgtt gaatggaaat tccaactacc ttcagctgcg ttctccacct   1560

ttccgactgt gaagtctaag atgggtatga acagggctgt tgctgtttca gatttgtcat   1620

atgttgcaaa cagtcagtca tctccgttaa gagaaggtat tttgatggct gtggatcatt   1680

tagatgatgt tgatgaaatt ttgtcacaaa gtttggggcg cgcc                   1724


<210> SEQ ID NO 6
<211> LENGTH: 3256
<212> TYPE: DNA
<213> ORGANISM: Artificial Sequence
<220> FEATURE:
<223> OTHER INFORMATION: Cassette with Saccharomyces cerevisiae Maf1
      coding sequence, regulatory sequences and integration sequences
<220> FEATURE:
<221> NAME/KEY: L0
<222> LOCATION: (362)..(401)
<220> FEATURE:
<221> NAME/KEY: Tef1
<222> LOCATION: (402)..(895)
<220> FEATURE:
<221> NAME/KEY: L1
<222> LOCATION: (896)..(935)
<220> FEATURE:
<221> NAME/KEY: MAF1
<222> LOCATION: (936)..(2123)
<220> FEATURE:
<221> NAME/KEY: L2
<222> LOCATION: (2124)..(2163)
<220> FEATURE:
<221> NAME/KEY: PRM9t
<222> LOCATION: (2164)..(2701)
<220> FEATURE:
<221> NAME/KEY: LTP2
<222> LOCATION: (2702)..(2741)

<400> SEQUENCE: 6

aatgatttaa gcgtgcgtga agataacact acaatccatt ttaaagcaac atccacattg     60

agtgtataca ccacaaaggt tttttcaggg cgtttttctc gccactttat gttgaccaaa    120

attattaatg gaacttacaa cgtttccaaa agttagttaa atacatacgt ctatttacta    180

agcaagaaat atatcatgac aagcccaaat attatattgt tatgtttaca aaaaaaaaat    240

ggctatatac atcaagtctg gaggcttttt ataacaagca agtggggtaa cttagacata    300

agattgactt ctttgaattc aacaaaaata catacttttg atgatttcaa tggtagaagc    360

ataaacaaca aataatcata aaaattttag aactagacat aaagcaacag gcgcgttgga    420

cttttaattt tcgaggaccg cgaatcctta catcacaccc aatcccccac aagtgatccc    480

ccacacacca tagcttcaaa atgtttctac tccttttta ctcttccaga ttttctcgga    540

ctccgcgcat cgccgtacca cttcaaaaca cccaagcaca gcatactaaa tttcccctct    600

ttcttcctct agggtgtcgt taattacccg tactaaaggt ttggaaaaga aaaaagagac    660

cgcctcgttt ctttttcttc gtcgaaaaag gcaataaaaa tttttatcac gtttcttttt    720

cttgaaaatt tttttttttg atttttttct ctttcgatga cctcccattg atatttaagt    780

taataaacgg tcttcaattt ctcaagtttc agtttcattt ttcttgttct attacaactt    840

tttttacttc ttgctcatta gaaagaaagc atagcaatct aatctaagtt ttaatctaga    900
```

```
aaatttatta taaaaggaag agaaataatt aaacaatgaa atttattgat gagctagata    960
tagagagagt gaatcaaact ctcaatttcg agacaaatga ctgtaaaatc gtgggcagtt   1020
gcgatatttt cacaacaaag gcggttgcat cagatagaaa attatataaa actattgatc   1080
agcatttgga tactatttta caggaaaatg agaattacaa tgctaccctt cagcaacagc   1140
tagctgctcc cgaaacaaac caatcaccct gctcgtcgcc attttattct aataggaggg   1200
atagcaactc tttttgggag caaaagagaa gaatatcttt tagtgaatac aatagcaata   1260
ataacactaa caacagtaat ggcaatagca gtaataacaa taactattct ggacctaatg   1320
gttcttctcc agcaactttt cccaaaagtg ccaagctaaa tgaccaaaat ttaaaagaat   1380
tagtctcgaa ttacgattct ggctctatga gctcatcgtc tcttgattct tcttctaaga   1440
atgatgagag gataagaaga aggagcagta gcagtattag cagtttcaaa agtggtaaat   1500
catcgaacaa taattacagt tctggtacag caaccaacaa tgttaacaaa agaagaaaat   1560
cttcgataaa cgaaaggcca agcaatttaa gtttgggtcc gtttggtccc ataaacgaac   1620
cgtcaagccg caaaatattt gcttatctga ttgctatcct caacgcttct tatcctgacc   1680
atgatttttc atcggttgag ccaacggatt ttgtcaaaac atcattgaaa acttttattt   1740
ccaaatttga aaacacctta tattctcttg gtagacaacc agaggaatgg gtctgggagg   1800
taattaattc tcacatgact ctttctgatt gcgtcctttt tcaatattca ccttcaaact   1860
ctttttttgga agatgagcct ggctatcttt ggaatcttat aggttttctt tacaacagga   1920
aaaggaaaag agtggcttac ctttacttga tttgctcgcg tctaaattcg agtacaggcg   1980
aagtggaaga tgccttggca aaaaaacctc agggaaagct tataatagat gatggctcaa   2040
atgaatacga aggagaatac gatttcactt atgatgagaa tgtaatagat gataaatcag   2100
atcaagaaga atccctacag tagagacata aaactgaaac aacaccaatt aataatagac   2160
tttacagaag acgggagaca ctagcacaca actttaccag gcaaggtatt tgacgctagc   2220
atgtgtccaa ttcagtgtca tttatgattt tttgtagtag gatataaata tatacagcgc   2280
tccaaatagt gcggttgccc caaaaacacc acggaacctc atctgttctc gtactttgtt   2340
gtgacaaagt agctcactgc cttattatca cattttcatt atgcaacgct tcggaaaata   2400
cgatgttgaa aatgcctcta gagatgaaaa acaatcgtaa aagggtcctg cgtaattgaa   2460
acatttgatc agtatgcagt ggcacagaaa caaccaggaa tactatagtc ataggcaata   2520
caaggtatat attggctatg cagacccctc cagaaagtac cgacgtcaag ttagatacac   2580
ttaacgaacc tagtgcacat ttaattgaga aaaatgtggc tcttcctaag gacatattcc   2640
gttcgtactt gagttattgg atctatgaaa tcgctcgcta tacaccagtc atgattttgt   2700
ccttaaataa catactcatc actaaacatt cttaacaatc agaaaacaac gcgtcatgaa   2760
aaagagttac tgaaccttca gatcctactt attgtaatgc ttcgcgacat ccaatccatt   2820
taataatcaa tttaaaacta gagttggtag agttccttgt tgaacgtgat aacccaaaag   2880
cataatacga gtaatgtttc agtattgcta ttatatgttt acacaaggaa aacatataat   2940
aacaaacctc taatccggta gtacttaaga aactatagtt tctatgtaca aaaaggtaac   3000
tatgtaattc ttacatttac ataacgtata gaagggtcca ataaacttac taaacttact   3060
accttgttgt atataggcta gatcgtaatc cactacgtca acataaaaaa aacttaagaa   3120
gtttgaattt tatgtacaaa cagattgtta aaatataata taagattatg gaaacgaact   3180
tgctctaaaa aaaatttaaa gttttataaa atcctcgaac tatcgctgtt atacatgatg   3240
```

```
tccccaaagc gtgtac                                                   3256


<210> SEQ ID NO 7
<211> LENGTH: 4662
<212> TYPE: DNA
<213> ORGANISM: Artificial Sequence
<220> FEATURE:
<223> OTHER INFORMATION: Cassette with Saccharomyces cerevisiae
      UPC2E888D coding sequence, regulatory sequences and integration
      sequences
<220> FEATURE:
<221> NAME/KEY: L0
<222> LOCATION: (401)..(440)
<220> FEATURE:
<221> NAME/KEY: Tef1
<222> LOCATION: (441)..(934)
<220> FEATURE:
<221> NAME/KEY: L1
<222> LOCATION: (935)..(974)
<220> FEATURE:
<221> NAME/KEY: UPC2-1
<222> LOCATION: (975)..(3701)
<220> FEATURE:
<221> NAME/KEY: g-a G888D
<222> LOCATION: (3637)..(3637)
<220> FEATURE:
<221> NAME/KEY: L2
<222> LOCATION: (3702)..(3741)
<220> FEATURE:
<221> NAME/KEY: PRM9t
<222> LOCATION: (3742)..(4279)
<220> FEATURE:
<221> NAME/KEY: LTP2
<222> LOCATION: (4280)..(4319)

<400> SEQUENCE: 7

cccagttgtt tgtagctggt tcatatttag cggcaattct ctgttgcgta aatgaaaata     60

ttaatgtaaa caaaaaaaga ccaaaacatt ttagcagtgt aagaaggtgt actgatacaa    120

aatgtgttta gagtctactg atatgttact gaccgttcgt tgggaaaaaa atactgtatc    180

atttattaat caaaagcgac ttttggtgga atattatgat atgtgttgtt aaaatatgac    240

gtaattttag aattgtctga ttcgtattca aatttggtga aggaataacg cagagttgac    300

aatttaatag aatggattaa tcgtaatttt cagaaacgta gaaaaagaaa aacaattaaa    360

acattatatt aagattattg atttgccttt taagggtcca taaacaacaa ataatcataa    420

aaattttaga actagacata aagcaacagg cgcgttggac ttttaatttt cgaggaccgc    480

gaatccttac atcacaccca atcccccaca agtgatcccc cacacaccat agcttcaaaa    540

tgtttctact cctttttac tcttccagat tttctcggac tccgcgcatc gccgtaccac    600

ttcaaaacac ccaagcacag catactaaat ttcccctctt tcttcctcta gggtgtcgtt    660

aattacccgt actaaaggtt tggaaaagaa aaaagagacc gcctcgtttc tttttcttcg    720

tcgaaaaagg caataaaaat ttttatcacg tttcttttc ttgaaaattt tttttttga     780

ttttttctc tttcgatgac ctcccattga tatttaagtt aataaacggt cttcaatttc     840

tcaagtttca gtttcatttt tcttgttcta ttacaacttt ttttacttct tgctcattag    900

aaagaaagca tagcaatcta atctaagttt taatctagaa aatttattat aaaaggaaga    960

gaaataatta aacaatgagc gaagtcggta tacagaatca caagaaagcg gtgacaaaac   1020

ccagaagaag agaaaaagtc atcgagctaa ttgaagtgga cggcaaaaag gtgagtacga   1080

cttcaaccgg taaacgtaaa ttccataaca aatcaaagaa tgggtgcgat aactgtaaaa   1140

gaagaagagt taagtgtgat gaagggaagc cagcctgtag gaagtgcaca aatatgaagt   1200

tggaatgtca gtatacacca atccatttaa ggaaaggtag aggagcaaca gtagtgaagt   1260
```

```
atgtcacgag aaaggcagac ggtagcgtgg agtctgattc atcggtagat ttacctccta   1320
cgatcaagaa ggagcagaca ccgttcaatg atatccaatc agcggtaaaa gcttcaggct   1380
catccaatga ttcctttcca tcaagcgcct ctacaactaa gagtgagagc gaggaaaagt   1440
catcggcccc tatagaggac aaaaacaata tgactcctct aagtatgggc ctccagggta   1500
ccatcaataa gaaagatatg atgaataact ttttctctca aaatggcact attggttttg   1560
gttctcctga aagattgaat tcaggtatcg atggcttact attaccgcca ttgccttctg   1620
gaaatatggg tgcgttccaa cttcagcaac agcagcaagt gcagcagcaa tctcaaccac   1680
agacccaagc gcagcaagca agtggaactc caaacgagag atatggttca ttcgatcttg   1740
cgggtagtcc tgcattgcaa tccacgggaa tgagcttatc aaatagtcta agcgggatgt   1800
tactatgtaa caggattcct tccggccaaa actacactca acaacaatta caatatcaat   1860
tacaccagca gctgcaattg caacagcatc agcaagttca gctgcagcag tatcaacaat   1920
tacgtcagga acaacaccaa caagttcagc aacaacaaca ggaacaactc cagcaatacc   1980
aacaacattt tttgcaacag cagcaacaag tactgcttca gcaagagcaa caacctaacg   2040
atgaggaagg tggcgttcag gaagaaaaca gcaaaaaggt aaaggaaggg cctttacaat   2100
cacaaacaag cgaaactact ttaaacagcg atgctgctac attacaagct gatgcattat   2160
ctcagttaag taagatgggg ctaagcctaa agtcgttaag tacctttcca acagctggta   2220
ttggtggtgt ttcctatgac tttcaggaac tgttaggtat taagtttcca ataaataacg   2280
gcaattcaag agctactaag gccagcaacg cagaggaagc tttggccaat atgcaagagc   2340
atcatgaacg tgcagctgct tctgtaaagg agaatgatgg tcagctctct gatacgaaga   2400
gtccagcgcc atcgaataac gcccaagggg gaagtgctag tattatggaa cctcaggcgg   2460
ctgatgcggt ttcgacaatg gcgcctatat caatgattga aagaaacatg aacagaaaca   2520
gcaacatttc tccatcaacg ccctctgcag tgttgaatga taggcaagag atgcaagatt   2580
ctataagttc tctaggaaat ctgacaaaag cagccttgga gaacaacgaa ccaacgataa   2640
gtttacaaac atcacagaca gagaatgaag acgatgcatc gcggcaagac atgacctcaa   2700
aaattaataa cgaagctgac cgaagttctg tttctgctgg taccagtaac atcgctaagc   2760
ttttagatct ttctaccaaa ggcaatctga acctgataga catgaaactg tttcatcatt   2820
attgcacaaa ggtctggcct acgattacag cggccaaagt ttctgggcct gaaatatgga   2880
gggactacat accggagtta gcatttgact atccattttt aatgcacgct ttgttggcat   2940
tcagtgccac ccatctttcg aggactgaaa ctggactgga gcaatacgtt tcatctcacc   3000
gcctagacgc tctgagatta ttaagagaag ctgttttaga aatatctgag aataacaccg   3060
atgcgctagt tgccagcgcc ctgatactaa tcatggactc gttagcaaat gctagtggta   3120
acggcactgt aggaaaccaa agtttgaata gcatgtcacc aagcgcttgg atctttcatg   3180
tcaaaggtgc tgcaacaatt ttaaccgctg tgtggccttt gagtgaaaga tctaaatttc   3240
ataacattat atctgttgat cttagcgatt taggcgatgt cattaaccct gatgttggaa   3300
caattactga attggtatgt tttgatgaaa gtattgccga tttgtatcct gtcggcttag   3360
attcgccata tttgataaca ctagcttatt tagataaatt gcaccgtgaa aaaaaccagg   3420
gtgattttat tctgcgggta tttacatttc cagcattgct agacaagaca ttcctggcat   3480
tactgatgac aggtgattta ggtgcaatga gaattatgag atcatattat aaactacttc   3540
gaggatttgc cacagaggtc aaggataaag tctggtttct cgaaggagtc acgcaggtgc   3600
```

```
tgcctcaaga cgttgatgag tacaggggag gtggtgatat gcatatgatg ctaggattac   3660

catcgatgac aacaacaaat ttctctgatt tttcgttatg aagacataaa actgaaacaa   3720

caccaattaa taatagactt tacagaagac gggagacact agcacacaac tttaccaggc   3780

aaggtatttg acgctagcat gtgtccaatt cagtgtcatt tatgattttt tgtagtagga   3840

tataaatata tacagcgctc caaatagtgc ggttgcccca aaaacaccac ggaacctcat   3900

ctgttctcgt actttgttgt gacaaagtag ctcactgcct tattatcaca ttttcattat   3960

gcaacgcttc ggaaaatacg atgttgaaaa tgcctctaga gatgaaaaac aatcgtaaaa   4020

gggtcctgcg taattgaaac atttgatcag tatgcagtgg cacagaaaca accaggaata   4080

ctatagtcat aggcaataca aggtatatat tggctatgca gacccctcca gaaagtaccg   4140

acgtcaagtt agatacactt aacgaaccta gtgcacattt aattgagaaa aatgtggctc   4200

ttcctaagga catattccgt tcgtacttga gttattggat ctatgaaatc gctcgctata   4260

caccagtcat gattttgtcc ttaaataaca tactcatcac taaacattct taacaatcac   4320

gatggatgat gattggttct tatcataatt tgatttcggc agaagcaata ttagaggtat   4380

tgttgtaacg aaattccaat gtcatctgct tagtattatt aatgttacct gcatattatc   4440

acatgccgct taaaaatgtg ttataagtat taaaatctag tgaaagttga aatgtaatct   4500

aataggataa tgaaacatat gaaacggaat gaggaataat cgttgtatta ctatgtagag   4560

atatcgattt cattttgagg attcctatat tcttggggag aacttctact atattctgta   4620

tacatgatat aatagccttt accaacaatg gaatgccaac aa                      4662
```

```
<210> SEQ ID NO 8
<211> LENGTH: 3564
<212> TYPE: DNA
<213> ORGANISM: Artificial Sequence
<220> FEATURE:
<223> OTHER INFORMATION: Cassette with Aspergillus nidulans NpgA coding
      sequence, regulatory sequences and integration sequences
<220> FEATURE:
<221> NAME/KEY: LTP1 (L0)
<222> LOCATION: (596)..(635)
<220> FEATURE:
<221> NAME/KEY: Tef1p
<222> LOCATION: (636)..(1129)
<220> FEATURE:
<221> NAME/KEY: L1
<222> LOCATION: (1130)..(1169)
<220> FEATURE:
<221> NAME/KEY: NpgA
<222> LOCATION: (1170)..(2201)
<220> FEATURE:
<221> NAME/KEY: L2
<222> LOCATION: (2205)..(2244)
<220> FEATURE:
<221> NAME/KEY: PRM9t
<222> LOCATION: (2245)..(2782)
<220> FEATURE:
<221> NAME/KEY: LTP2
<222> LOCATION: (2783)..(2822)

<400> SEQUENCE: 8

tcaatcaaag caacccacaa atcctaggct gaatcatgat atcgatggaa gcaatcaaca     60

attttatcaa gaccgcacca aagcacgact atctgacagg cggagttcat cattctggta    120

atgtagacgt gttacaatta agcggcaata aagaagatgg tagtttagta tggaaccata    180

cttttgttga tgtagacaac aatgtggtag ctaagtttga agacgctctc gaaaaacttg    240

aaagtttgca ccggcgctca tcctcatcca caggcaatga agaacacgct aacgtttaac    300

cgaggggagt cacttcataa tgatgtgaga aataagtgaa tattgtaata attgttggga    360
```

```
ctccattgtc aacaaaagct ataatgtagg tatacagtat atactagaag ttctcctcga    420
ggatcttgga atccacaaaa gggagtcgat aaatctatat aataaaaatt actttatctt    480
ctttcgtttt atacgttgtc gtttattatc ctattacgtt atcaatcttc gcatttcagc    540
tttcattaga tttgatgact gtttctcaaa ctttatgtca ttttcttaca ccgcataaac    600
aacaaataat cataaaaatt ttagaactag acataaagca acaggcgcgt tggactttta    660
attttcgagg accgcgaatc cttacatcac acccaatccc ccacaagtga tcccccacac    720
accatagctt caaaatgttt ctactccttt tttactcttc cagattttct cggactccgc    780
gcatcgccgt accacttcaa aacacccaag cacagcatac taaatttccc ctctttcttc    840
ctctagggtg tcgttaatta cccgtactaa aggtttggaa aagaaaaaag agaccgcctc    900
gtttcttttt cttcgtcgaa aaaggcaata aaaattttta tcacgtttct ttttcttgaa    960
aatttttttt tttgattttt ttctctttcg atgacctccc attgatattt aagttaataa   1020
acggtcttca atttctcaag tttcagtttc atttttcttg ttctattaca actttttttta   1080
cttcttgctc attagaaaga aagcatagca atctaatcta agttttaatc tagaaaattt   1140
attataaaag gaagagaaat aattaaacaa tggttcaaga tacctcttct gcttctacct   1200
ctccaatttt gactagatgg tacattgata ccagaccatt gactgcttct actgctgctt   1260
tgccattatt ggaaacttta caaccagccg atcaaatctc cgttcaaaag tactatcact   1320
tgaaggacaa gcacatgtct ttggcttcta acttgttgaa gtacttgttc gttcacagaa   1380
actgcagaat tccatggtcc tctatcgtta tttctagaac tccagatcca catagaaggc   1440
catgttatat tccaccatct ggttctcaag aggattcttt taaagatggt tacaccggta   1500
tcaacgtcga gtttaatgtt tctcatcaag cctccatggt tgctattgct ggtactgctt   1560
ttactccaaa ttctggtggt gattctaagt tgaaaccaga agttggtatc gatattacct   1620
gcgtcaacga aagacaaggt agaaatggtg aagaaaggtc cttggaatct ttgagacagt   1680
acatcgatat cttctccgaa gttttctcta ctgctgaaat ggccaacatt agaagattgg   1740
atggtgtctc ttcttcctca ttgtctgctg atagattggt tgattatggc tacaggttgt   1800
tctatactta ctgggctttg aaagaagcct acattaagat gactggtgaa gccttgttgg   1860
ctccatggtt gagagaattg gaattctcta atgttgttgc tccagctgct gttgctgaat   1920
ctggtgattc tgctggtgat tttggtgaac catatactgg tgttagaacc accttgtaca   1980
agaacttggt tgaagatgtt agaattgaag ttgctgcttt gggtggtgat tacttgtttg   2040
ctactgctgc tagaggtggt ggtattggtg cttcttctag accaggtggt ggtccagatg   2100
gttctggtat tagatctcaa gatccttgga ggccattcaa gaagttggat attgaaaggg   2160
atattcaacc atgtgctact ggtgtatgta actgcttgtc ttaaagacat aaaactgaaa   2220
caacaccaat taataataga ctttacagaa gacgggagac actagcacac aactttacca   2280
ggcaaggtat ttgacgctag catgtgtcca attcagtgtc atttatgatt ttttgtagta   2340
ggatataaat atatacagcg ctccaaatag tgcggttgcc ccaaaaacac cacggaacct   2400
catctgttct cgtactttgt tgtgacaaag tagctcactg ccttattatc acattttcat   2460
tatgcaacgc ttcggaaaat acgatgttga aaatgcctct agagatgaaa aacaatcgta   2520
aaagggtcct gcgtaattga aacatttgat cagtatgcag tggcacagaa acaaccagga   2580
atactatagt cataggcaat acaaggtata tattggctat gcagacccct ccagaaagta   2640
ccgacgtcaa gttagataca cttaacgaac ctagtgcaca tttaattgag aaaaatgtgg   2700
```

```
ctcttcctaa ggacatattc cgttcgtact tgagttattg gatctatgaa atcgctcgct   2760

atacaccagt catgattttg tccttaaata acatactcat cactaaacat tcttaacaat   2820

cagaaaatgc aaccgataaa acattataaa tcttcgcggt tatctggcat tgttattaac   2880

caaaaaaatg ccggcctatt acaagctact gttcaataaa tattgttgta atgaagacgg   2940

tccaactgta caaatacagc aaactgtcat atataaggtg tcttatgtga cagcacttgc   3000

gttattgtca gccggagtat gtctttgtcg cattctgggc tttttacttt ctgctcagaa   3060

ggaagtacga acaagaaaaa aaaatcacca atgcttccct tttcagtatt agtttcatat   3120

ttgtttacgt tcaaactcgt cgtttgcgcg ataacctcta aaaaagtcag ttacgtaact   3180

atatcaatca gagaatgcaa aaagcactat cataaaaatg tctctagggg atgtgagaca   3240

tgtcaattat aagaagtgat ggtgtcatag tatatatatc ataaatgatt atcaaagttt   3300

caatcctttg tattttctag tttagcgcca acttttgaca aaacctaaac tttagataat   3360

catcattctt acaattttta tctggatggc aataatctcc tatataaagc ccagataaac   3420

tgtaaaaaga atccatcact atttgaaaaa aagtcatctg gcacgtttaa ttatcagagc   3480

agaaatgatg aagggtgtta gcgccgtcca ttgatgcgcc tggtagtcat gatttacgta   3540

taactaacac atcatgagga cggc                                          3564
```

<210> SEQ ID NO 9
<211> LENGTH: 10584
<212> TYPE: DNA
<213> ORGANISM: Artificial Sequence
<220> FEATURE:
<223> OTHER INFORMATION: Cassette with Dictyostelium discoideum DiPKS (G1516D; G1518A) coding sequence, regulatory sequences and integration sequences
<220> FEATURE:
<221> NAME/KEY: LV3
<222> LOCATION: (1)..(40)
<220> FEATURE:
<221> NAME/KEY: S. cerevisiae GAL1 promoter
<222> LOCATION: (41)..(482)
<220> FEATURE:
<221> NAME/KEY: L1
<222> LOCATION: (483)..(522)
<220> FEATURE:
<221> NAME/KEY: DiPKS
<222> LOCATION: (523)..(9966)
<220> FEATURE:
<221> NAME/KEY: C-methyltransferase domain
<222> LOCATION: (5050)..(5412)
<220> FEATURE:
<221> NAME/KEY: Motif 1
<222> LOCATION: (5050)..(5076)
<220> FEATURE:
<221> NAME/KEY: G1516D
<222> LOCATION: (5068)..(5070)
<220> FEATURE:
<221> NAME/KEY: G1518A
<222> LOCATION: (5074)..(5076)
<220> FEATURE:
<221> NAME/KEY: Motif 2
<222> LOCATION: (5309)..(5331)
<220> FEATURE:
<221> NAME/KEY: Motif 3
<222> LOCATION: (5389)..(5421)
<220> FEATURE:
<221> NAME/KEY: L2
<222> LOCATION: (9967)..(10006)
<220> FEATURE:
<221> NAME/KEY: PRM9t
<222> LOCATION: (10007)..(10544)
<220> FEATURE:
<221> NAME/KEY: LV5
<222> LOCATION: (10545)..(10584)

<400> SEQUENCE: 9

```
aggaatactc tgaataaaac aacttatata ataaaaatgc cggattagaa gccgccgagc     60
gggtgacagc cctccgaagg aagactctcc tccgtgcgtc ctcgtcttca ccggtcgcgt    120
tcctgaaacg cagatgtgcc tcgcgccgca ctgctccgaa caataaagat tctacaatac    180
tagcttttat ggttatgaag aggaaaaatt ggcagtaacc tggccccaca aaccttcaaa    240
tgaacgaatc aaattaacaa ccataggatg ataatgcgat tagtttttta gccttatttc    300
tggggtaatt aatcagcgaa gcgatgattt ttgatctatt aacagatata taaatgcaaa    360
aactgcataa ccactttaac taatactttc aacattttcg gtttgtatta cttcttattc    420
aaatgtaata aaagtatcaa caaaaaattg ttaatatacc tctatacttt aacgtcaagg    480
agctagaaaa tttattataa aaggaagaga aataattaaa caatgaacaa gaactccaaa    540
atccagtccc caaactcttc tgatgttgct gttattggtg ttggttttag attcccaggt    600
aactctaatg acccagaatc tttgtggaac aacttgttgg atggtttcga tgctattacc    660
caagtcccaa aagaaagatg ggctacttct tttagagaga tgggtttgat caagaacaag    720
ttcggtggtt tcttgaagga ttctgaatgg aagaatttcg accctttgtt ctttggtatc    780
ggtccaaaag aagctccatt cattgatcca caacaaaggt tgttgttgtc catcgtttgg    840
gaatctttgg aagatgctta catcagacca gatgaattga gaggttctaa cactggtgtt    900
ttcatcggtg tttctaacaa cgattacacc aagttgggtt tccaagacaa ctactctatt    960
tctccataca ctatgaccgg ctctaactct tcattgaact ccaacagaat ttcctactgc   1020
ttcgatttta gaggtccatc cattactgtt gataccgctt gttcttcttc cttggtttct   1080
gttaatttgg gtgtccaatc catccaaatg ggtgaatgta agattgctat ttgcggtggt   1140
gttaacgctt tgtttgatcc atctacatct gttgcctttt ccaagttggg tgttttgtct   1200
gaaaatggca gatgcaactc ttttagtgat caagcctctg gttacgttag atctgaaggt   1260
gctggtgttg ttgttttgaa gtctttggaa caagctaagt tggatggtga tagaatctac   1320
ggtgttatca agggtgtttc ctctaatgaa gatggtgctt ctaatggtga caagaactct   1380
ttgactactc catcttgtga agcccaatcc attaacattt ctaaggctat ggaaaaggcc   1440
tccttgtctc catctgatat ctattacatt gaagcccatg gtactggtac tccagttggt   1500
gatccaattg aagttaaggc cttgtccaag atcttctcca actctaacaa caaccagttg   1560
aacaacttct ctaccgatgg taatgataac gatgatgatg atgacgataa cacctctcca   1620
gaaccattat tgattggctc attcaagtcc aacatcggtc atttggaatc tgctgctggt   1680
attgcttctt tgattaagtg ttgcttgatg ttgaagaaca ggatgttggt tccatccatt   1740
aactgctcta atttgaaccc atccattcca ttcgatcagt acaacatctc cgttatcaga   1800
gaaatcagac aattcccaac cgataagttg gttaacatcg gtatcaattc tttcggtttc   1860
ggtggttcta actgccattt gattattcaa gagtacaaca acaacttcaa gaacaactct   1920
accatctgca ataacaacaa caacaacaat aacaacatcg actacttgat cccaatctcc   1980
tctaagacta agaagtcctt ggataagtac ttgattttga tcaagaccaa ctccaactac   2040
cacaaggata tttctttcga tgacttcgtc aagttccaaa tcaagtctaa gcagtacaac   2100
ttgtccaaca gaatgactac cattgctaac gattggaact ccttcattaa gggttctaac   2160
gaattccaca acttgatcga atctaaggat ggtgaaggtg gttcttcatc ttctaacaga   2220
ggtattgatt ccgccaatca aatcaacact actactacct ctaccatcaa cgatatcgaa   2280
cctttgttgg ttttcgtttt ctgtggtcaa ggtccacaat ggaatggtat gattaagacc   2340
```

```
ttgtacaact ccgagaacgt tttcaagaac accgttgatc atgttgacag catcttgtac   2400
aagtacttcg gttactccat tttgaacgtc ttgtctaaga tcgatgataa cgacgattcc   2460
atcaaccatc caatagttgc tcaaccatct ttgttcttgt tgcaaattgg tttggtcgag   2520
ttgtttaagt actggggtat ctacccatct atctctgttg gtcattcttt cggtgaagtc   2580
tcttcttatt acttgtccgg tatcatctct ttggaaaccg cttgtaaaat cgtctacgtc   2640
agatcctcta atcagaacaa aactatgggt tccggtaaga tgttggttgt ttctatgggt   2700
tttaagcaat ggaacgatca attctctgct gaatggtccg atattgaaat tgcttgttac   2760
aacgctccag attccatagt tgttactggt aacgaagaaa gattgaaaga attgtccatc   2820
aagttgtccg acgaatccaa tcaaattttc aacaccttct tgaggtcccc atgttctttt   2880
cattcttccc atcaagaagt catcaagggt tctatgttcg aagagttgtc taacttgcaa   2940
tctactggtg aaaccgaaat ccctttgttc tctactgtta ctggtagaca agttttgtct   3000
ggtcatgtta ctgctcaaca catctacgat aatgttagag aaccagtctt gttccaaaag   3060
acgattgaat ccattacctc ctacatcaag tctcactacc catccaatca aaaggttatc   3120
tacgttgaaa ttgctccaca cccaaccttg ttttcattga tcaaaaagtc catcccatcc   3180
tccaacaaga attcctcttc tgttttgtgt ccattgaaca gaaaagaaaa ctccaacaac   3240
tcctacaaga agttcgtttc tcagttgtac ttcaacggtg ttaacgttga cttcaacttc   3300
cagttgaact ccatttgcga taacgttaac aacgatcacc atttgaacaa cgtcaagcaa   3360
aactccttca aagagactac caattccttg ccaagatacc aatgggaaca agatgaatat   3420
tggtccgaac cattgatctc cagaaagaat agattggaag gtccaactac ttccttgttg   3480
ggtcatagaa ttatctacag cttcccagtt ttccaatccg ttttggactt gcaatctgac   3540
aactacaaat acttgttgga ccacttggtt aacggtaagc cagtttttcc aggtgctggt   3600
tatttggata tcatcatcga attcttcgac taccaaaagc agcagttgaa ttcctctgat   3660
tcctctaact cctacatcat caacgttgac aagatccaat tcttgaaccc aattcacttg   3720
accgaaaaca agttgcaaac cttgcaatct tctttcgaac ctatcgttac taagaagtct   3780
gccttctctg ttaacttctt catcaaggat accgtcgagg atcaatctaa ggttaagtct   3840
atgtctgacg aaacttggac taacacttgt aaggctacca tttccttgga acaacaacag   3900
ccatctccat cttctacttt gactttgtct aagaagcaag acttgcagat cttgagaaac   3960
agatgcgata ttagcaagct agacaagttt gagttgtacg acaagatctc taagaatttg   4020
ggcttgcagt acaactcctt gtttcaagtt gttgatacca tcgaaactgg taaggattgc   4080
tcttttgcta ctttgtcttt gccagaagat actttgttca ccaccatttt gaacccatgc   4140
ttgttggata actgtttcca tggtttgttg accttgatca acgaaaaggg ttctttcgtt   4200
gtcgagtcca tttcttctgt ttctatctac ttggagaaca tcggttcctt caatcaaact   4260
tctgttggta acgtccagtt ctacttgtac accactattt ctaaagccac ctcctttagt   4320
tctgaaggta cttgtaagtt gttcaccaag gatggttcct tgattttgtc tatcggtaag   4380
ttcatcatca agtccaccaa tccaaagtct actaagacca acgaaactat cgaatctcca   4440
ttggacgaaa ccttctctat tgaatggcaa tctaaggatt ctccaattcc aaccccacaa   4500
caaatccaac aacaatctcc attgaactct aacccatcct tcattagatc taccatcttg   4560
aaggacatcc agttcgaaca atactgctcc tccattatcc acaaagaatt gatcaaccac   4620
gaaaagtaca agaaccagca atccttcgat atcaactcct tggaaaacca cttgaacgat   4680
```

-continued

```
gaccaattga tggaatcctt gtccatctcc aaagaatact tgagattctt caccaggatc   4740
atctccatca ttaagcaata cccaaagatc ttgaacgaaa aagagctaaa agaattgaaa   4800
gaaatcatcg aattgaagta cccatccgaa gttcagttgt tggaattcga agttatcgag   4860
aaggtgtcca tgattatccc aaagttgttg ttcgaaaacg acaagcaatc ttccatgacc   4920
ttgttccaag ataacttgtt gaccaggttc tactccaatt ctaactctac cagattctac   4980
ttggaaaggg tttccgaaat ggtcttggaa tctattagac caatcgtcag agaaaagagg   5040
gtgttcagaa ttttggaaat tggtgctgat acagcctctt tgtctaatgt tgttttgact   5100
aagttgaaca cctacttgtc caccttgaat tctaatggtg gttctggtta caacatcatc   5160
attgagtaca ccttcaccga tatttccgcc aacttcatta ttggtgaaat ccaagaaacc   5220
atgtgcaact tgtacccaaa cgttactttc aagttctccg tcttggactt ggagaaagag   5280
attattaact cctccgattt cttgatgggt gattacgata tagttttgat ggcctacgtt   5340
atccatgccg tttctaacat taagttctcc atcgaacagt tgtacaagtt gttgtctcca   5400
agaggttggt tgttgtgtat tgaacctaag tccaacgttg tgttctccga tttggttttc   5460
ggttgtttta atcagtggtg gaactactac gatgatatta gaactaccca ctgctccttg   5520
tctgaatctc aatggaatca gttgttgttg aaccagtcct tgaacaacga atcctcttct   5580
tcttctaact gttacggtgg tttctccaac gtttctttta ttggtggtga aaaggatgtc   5640
gactcccatt ctttcatatt gcactgccaa aaagaatcca tctcccaaat gaagttagcc   5700
accactatta acaacggttt gtcatctggt tccatcgtta tcgttttgaa ctctcaacaa   5760
ttgaccaaca tgaagtccta cccaaaggtt attgagtata ttcaagaggc tacctctttg   5820
tgcaagacca ttgaaattat cgattccaag gacgtcttga actctaccaa ttcagttttg   5880
gaaaagatcc aaaagtcctt gttggtgttc tgtttgttgg gttatgactt gttggagaac   5940
aactaccaag aacagtcttt cgaatacgtt aagttgttga acttgatctc tactaccgcc   6000
tcttcatcta atgataagaa accaccaaag gtcttgttga tcaccaagca atctgaaaga   6060
atctccaggt ctttctactc cagatccttg attggtattt ccagaacctc tatgaacgag   6120
tacccaaatt tgtccattac ctctatcgat ttggatacca acgactactc attgcagtct   6180
ttgttgaagc caatcttcag caactctaag ttttccgaca acgagttcat cttcaaaaag   6240
ggcttgatgt tcgtgtccag gatctttaag aacaagcagt tgctagaatc ctccaacgct   6300
tttgaaactg actcttctaa cttgtactgt aaggcctctt ctgacttgtc ttacaagtac   6360
gctattaagc agtctatgtt gaccgaaaat cagatcgaaa tcaaggttga atgcgtcggt   6420
attaacttca aggacaacct attctacaag ggcttgttgc cacaagaaat tttcagaatg   6480
ggtgacatct acaatccacc atatggtttg gaatgctctg gtgttattac cagaattggt   6540
tctaacgtca ccgaatactc agttggtcaa aatgtttttg gtttcgccag acattctttg   6600
ggttctcatg ttgttaccaa caaggatttg gttatcttga agccagatac catctcattt   6660
tctgaagctg cttctatccc agttgtttac tgtactgctt ggtactcctt gttcaacatt   6720
ggtcagttgt ctaacgaaga atccatccta attcattctg ctactggtgg tgtaggtttg   6780
gcttctttga atttgttgaa aatgaagaat cagcaacagc aaccattgac caatgtttat   6840
gctactgttg gctctaacga gaagaagaag ttcttgatcg ataacttcaa caacttgttc   6900
aaagaggacg gcgaaaacat tttctctacc agagacaaag aatactccaa ccagttggaa   6960
tccaagatcg atgttatttt gaacaccttg tccggtgaat tcgtcgaatc taatttcaag   7020
tccttgagat ccttcggtag attgattgat ttgtctgcta ctcacgttta cgccaatcaa   7080
```

```
caaattggtc taggtaactt caagttcgac cacttgtatt ctgctgttga cttggaaaga   7140
ttgatcgacg aaaaacctaa gttgttgcag tccatcttgc aaagaattac caactctatc   7200
gtcaacggtt ccttggaaaa aattccaatt accatcttcc catccaccga aactaaggat   7260
gctatcgaat tattgtccaa gagatcccat atcggtaaag ttgttgtaga ttgcaccgat   7320
atctctaagt gtaatcctgt tggtgatgtg atcaccaact tctctatgag attgccaaag   7380
ccaaactacc agttgaattt gaactccacc ttgttgatta ctggtcagtc tggtttgtct   7440
atccctttgt tgaattggtt gttgtctaag tctggtggta acgttaagaa cgttgtcatc   7500
atttctaagt ccaccatgaa gtggaagttg cagactatga tttcccattt cgtttccggt   7560
ttcggtatcc attttaacta cgttcaagtc gacatctcca actacgatgc tttgtctgaa   7620
gctattaagc aattgccatc tgatttgcca ccaatcacct ctgtttttca tttggctgct   7680
atctacaacg atgttccaat ggatcaagtt accatgtcta ccgttgaatc tgttcataac   7740
cctaaagttt tgggtgccgt taacttgcat agaatctctg tttcttttgg ttggaagttg   7800
aaccacttcg tcttgttctc ttctattact gctattaccg gttacccaga ccaatctatc   7860
tacaattctg ccaactctat tttggacgct ttgtccaact ttagaaggtt tatgggtttg   7920
ccatccttct ccattaactt gggtccaatg aaggatgaag gtaaggtttc taccaacaag   7980
agcatcaaga agctattcaa gtctagaggt ttgccaagcc tatccttgaa caagttattt   8040
ggtttgttgg aggtcgtcat caacaaccca tctaatcatg ttatcccatc ccaattgatt   8100
tgctccccaa tcgatttcaa gacctacatc gaatctttct caactatgag gccaaagttg   8160
ttacacttgc aacctaccat ttccaagcag caatcttcta tcattaacga ttctaccaag   8220
gcttcctcca acatttcatt gcaagataag atcacctcca aggtgtctga tttgttgtcc   8280
attccaatct ccaagatcaa cttcgatcat ccattgaaac actacggctt ggattctttg   8340
ttgaccgttc aattcaaatc ctggatcgac aaagaattcg aaaagaactt gttcacccat   8400
atccaattgg ccaccatctc tattaactca ttcttggaaa aggtgaacgg cttgtctaca   8460
aacaataaca acaacaacaa ttccaacgtc aagtcctctc catccattgt caaagaagaa   8520
atcgttacct tggacaagga tcaacaacca ttgctattga aagaacacca gcacattatc   8580
atctccccag atattagaat caacaagcca aagagggaat ccttgattag aaccccaatc   8640
ttgaacaaat tcaaccagat caccgaatcc attatcactc catctacacc atctttgtcc   8700
caatccgatg ttttgaaaac tccaccaatc aagtctttga acaacactaa gaactccagc   8760
ttgattaaca ccccaccaat tcaatctgtc caacaacatc aaaagcaaca acaaaaggtc   8820
caagtcatcc aacaacagca acaaccatta tccagattgt cctacaagag caacaacaac   8880
tctttcgttt tgggtatcgg tatttctgtt ccaggtgaac ctatttccca acaatccttg   8940
aaagactcca tctccaatga cttttctgat aaggctgaaa ctaacgagaa ggtcaagaga   9000
atctttgagc aatctcaaat caagaccaga cacttggtta gagattacac taagccagag   9060
aactccatca agttcagaca tttggaaacc attaccgatg tgaacaacca gttcaagaaa   9120
gttgttccag atttggctca acaagcctgt ttgagagctt tgaaagattg ggggtggtgat   9180
aagggtgata ttacccatat agtttctgtt acctccaccg gtattatcat cccagatgtt   9240
aatttcaagt tgatcgactt gttgggcttg aacaaggatg ttgaaagagt gtctttgaac   9300
ctaatgggtt gtttggctgg tttgagttct ttgagaactg ctgcttcttt ggctaaggct   9360
tctccaagaa atagaatttt ggttgtctgt accgaagtct gctccttgca tttttctaat   9420
```

```
actgatggtg gtgatcaaat ggtcgcctct tctatttttg ctgatggttc tgctgcttac   9480

attattggtt gtaacccaag aattgaagaa accccattat acgaagtcat gtgctccatt   9540

aacagatctt tcccaaatac cgaaaacgcc atggtttggg atttggaaaa agaaggttgg   9600

aacttgggtt tggatgcttc tattccaatt gtcattggtt ctggtattga agccttcgtt   9660

gatactttgt tggataaggc taagttgcaa acttccactg ctatttctgc taaggattgc   9720

gaattcttga ttcatactgg tggcaagtcc atcttgatga acatcgaaaa ttccttgggt   9780

atcgacccaa agcaaactaa gaatacttgg gatgtttacc atgcctacgg caatatgtca   9840

tctgcctctg ttattttcgt tatggatcat gccagaaagt ccaagtcttt gccaacttac   9900

tcaatttctt tggcttttgg tccaggtttg gcttttgaag gttgtttctt gaagaacgtc   9960

gtctaaagac ataaaactga aacaacacca attaataata gactttacag aagacgggag  10020

acactagcac acaactttac caggcaaggt atttgacgct agcatgtgtc caattcagtg  10080

tcatttatga ttttttgtag taggatataa atatatacag cgctccaaat agtgcggttg  10140

ccccaaaaac accacggaac ctcatctgtt ctcgtacttt gttgtgacaa agtagctcac  10200

tgccttatta tcacattttc attatgcaac gcttcggaaa atacgatgtt gaaaatgcct  10260

ctagagatga aaaacaatcg taaaagggtc ctgcgtaatt gaaacatttg atcagtatgc  10320

agtggcacag aaacaaccag gaatactata gtcataggca atacaaggta tatattggct  10380

atgcagaccc ctccagaaag taccgacgtc aagttagata cacttaacga acctagtgca  10440

catttaattg agaaaaatgt ggctcttcct aaggacatat tccgttcgta cttgagttat  10500

tggatctatg aaatcgctcg ctatacacca gtcatgattt tgtccctctt tatattacat  10560

caaaataaga aaataattat aaca                                          10584
```

```
<210> SEQ ID NO 10
<211> LENGTH: 10584
<212> TYPE: DNA
<213> ORGANISM: Artificial Sequence
<220> FEATURE:
<223> OTHER INFORMATION: Cassette with Dictyostelium discoideum DiPKS
      (G1516R) coding sequence,  regulatory sequences and integration
      sequences
<220> FEATURE:
<221> NAME/KEY: LV3
<222> LOCATION: (1)..(40)
<220> FEATURE:
<221> NAME/KEY: S. cerevisiae GAL1 promoter
<222> LOCATION: (41)..(482)
<220> FEATURE:
<221> NAME/KEY: L1
<222> LOCATION: (483)..(522)
<220> FEATURE:
<221> NAME/KEY: DiPKS
<222> LOCATION: (523)..(9966)
<220> FEATURE:
<221> NAME/KEY: C-methyltransferase domain
<222> LOCATION: (5050)..(5412)
<220> FEATURE:
<221> NAME/KEY: G1516R
<222> LOCATION: (5069)..(5070)
<220> FEATURE:
<221> NAME/KEY: Motif 2
<222> LOCATION: (5309)..(5331)
<220> FEATURE:
<221> NAME/KEY: Motif 3
<222> LOCATION: (5389)..(5421)
<220> FEATURE:
<221> NAME/KEY: Type III PKS domain
<222> LOCATION: (8881)..(9966)
<220> FEATURE:
<221> NAME/KEY: L2
<222> LOCATION: (9967)..(10006)
```

```
<220> FEATURE:
<221> NAME/KEY: PRM9t
<222> LOCATION: (10007)..(10544)
<220> FEATURE:
<221> NAME/KEY: LV5
<222> LOCATION: (10545)..(10584)

<400> SEQUENCE: 10

aggaatactc tgaataaaac aacttatata ataaaaatgc cggattagaa gccgccgagc      60

gggtgacagc cctccgaagg aagactctcc tccgtgcgtc ctcgtcttca ccggtcgcgt     120

tcctgaaacg cagatgtgcc tcgcgccgca ctgctccgaa caataaagat tctacaatac     180

tagcttttat ggttatgaag aggaaaaatt ggcagtaacc tggccccaca aaccttcaaa     240

tgaacgaatc aaattaacaa ccataggatg ataatgcgat tagtttttta gccttatttc     300

tggggtaatt aatcagcgaa gcgatgattt ttgatctatt aacagatata taaatgcaaa     360

aactgcataa ccactttaac taatactttc aacattttcg gtttgtatta cttcttattc     420

aaatgtaata aaagtatcaa caaaaaattg ttaatatacc tctatacttt aacgtcaagg     480

agctagaaaa tttattataa aaggaagaga aataattaaa caatgaacaa gaactccaaa     540

atccagtccc caaactcttc tgatgttgct gttattggtg ttggttttag attcccaggt     600

aactctaatg acccagaatc tttgtggaac aacttgttgg atggtttcga tgctattacc     660

caagtcccaa aagaaagatg ggctacttct tttagagaga tgggtttgat caagaacaag     720

ttcggtggtt tcttgaagga ttctgaatgg aagaatttcg accctttgtt ctttggtatc     780

ggtccaaaag aagctccatt cattgatcca caacaaaggt tgttgttgtc catcgtttgg     840

gaatctttgg aagatgctta catcagacca gatgaattga gaggttctaa cactggtgtt     900

ttcatcggtg tttctaacaa cgattacacc aagttgggtt tccaagacaa ctactctatt     960

tctccataca ctatgaccgg ctctaactct tcattgaact ccaacagaat ttcctactgc    1020

ttcgatttta gaggtccatc cattactgtt gataccgctt gttcttcttc cttggtttct    1080

gttaatttgg gtgtccaatc catccaaatg ggtgaatgta agattgctat ttgcggtggt    1140

gttaacgctt tgtttgatcc atctacatct gttgcctttt ccaagttggg tgttttgtct    1200

gaaaatggca gatgcaactc ttttagtgat caagcctctg gttacgttag atctgaaggt    1260

gctggtgttg ttgttttgaa gtctttggaa caagctaagt tggatggtga tagaatctac    1320

ggtgttatca agggtgtttc ctctaatgaa gatggtgctt ctaatggtga caagaactct    1380

ttgactactc catcttgtga agcccaatcc attaacattt ctaaggctat ggaaaaggcc    1440

tccttgtctc catctgatat ctattacatt gaagcccatg gtactggtac tccagttggt    1500

gatccaattg aagttaaggc cttgtccaag atcttctcca actctaacaa caaccagttg    1560

aacaacttct ctaccgatgg taatgataac gatgatgatg atgacgataa cacctctcca    1620

gaaccattat tgattggctc attcaagtcc aacatcggtc atttggaatc tgctgctggt    1680

attgcttctt tgattaagtg ttgcttgatg ttgaagaaca ggatgttggt tccatccatt    1740

aactgctcta atttgaaccc atccattcca ttcgatcagt acaacatctc cgttatcaga    1800

gaaatcagac aattcccaac cgataagttg gttaacatcg gtatcaattc tttcggtttc    1860

ggtggttcta actgccattt gattattcaa gagtacaaca acaacttcaa gaacaactct    1920

accatctgca ataacaacaa caacaacaat aacaacatcg actacttgat cccaatctcc    1980

tctaagacta agaagtcctt ggataagtac ttgattttga tcaagaccaa ctccaactac    2040

cacaaggata tttctttcga tgacttcgtc aagttccaaa tcaagtctaa gcagtacaac    2100
```

-continued

```
ttgtccaaca gaatgactac cattgctaac gattggaact ccttcattaa gggttctaac   2160
gaattccaca acttgatcga atctaaggat ggtgaaggtg gttcttcatc ttctaacaga   2220
ggtattgatt ccgccaatca aatcaacact actactacct ctaccatcaa cgatatcgaa   2280
cctttgttgg ttttcgtttt ctgtggtcaa ggtccacaat ggaatggtat gattaagacc   2340
ttgtacaact ccgagaacgt tttcaagaac accgttgatc atgttgacag catcttgtac   2400
aagtacttcg gttactccat tttgaacgtc ttgtctaaga tcgatgataa cgacgattcc   2460
atcaaccatc caatagttgc tcaaccatct ttgttcttgt tgcaaattgg tttggtcgag   2520
ttgtttaagt actggggtat ctacccatct atctctgttg gtcattcttt cggtgaagtc   2580
tcttcttatt acttgtccgg tatcatctct ttggaaaccg cttgtaaaat cgtctacgtc   2640
agatcctcta atcagaacaa aactatgggt tccggtaaga tgttggttgt ttctatgggt   2700
tttaagcaat ggaacgatca attctctgct gaatggtccg atattgaaat tgcttgttac   2760
aacgctccag attccatagt tgttactggt aacgaagaaa gattgaaaga attgtccatc   2820
aagttgtccg acgaatccaa tcaaattttc aacaccttct tgaggtcccc atgttctttt   2880
cattcttccc atcaagaagt catcaagggt tctatgttcg aagagttgtc taacttgcaa   2940
tctactggtg aaaccgaaat ccctttgttc tctactgtta ctggtagaca agttttgtct   3000
ggtcatgtta ctgctcaaca catctacgat aatgttagag aaccagtctt gttccaaaag   3060
acgattgaat ccattacctc ctacatcaag tctcactacc catccaatca aaaggttatc   3120
tacgttgaaa ttgctccaca cccaaccttg ttttcattga tcaaaaagtc catcccatcc   3180
tccaacaaga attcctcttc tgttttgtgt ccattgaaca gaaaagaaaa ctccaacaac   3240
tcctacaaga agttcgtttc tcagttgtac ttcaacggtg ttaacgttga cttcaacttc   3300
cagttgaact ccatttgcga taacgttaac aacgatcacc atttgaacaa cgtcaagcaa   3360
aactccttca aagagactac caattccttg ccaagatacc aatgggaaca agatgaatat   3420
tggtccgaac cattgatctc cagaaagaat agattggaag gtccaactac ttccttgttg   3480
ggtcatagaa ttatctacag cttcccagtt ttccaatccg ttttggactt gcaatctgac   3540
aactacaaat acttgttgga ccacttggtt aacggtaagc cagtttttcc aggtgctggt   3600
tatttggata tcatcatcga attcttcgac taccaaaagc agcagttgaa ttcctctgat   3660
tcctctaact cctacatcat caacgttgac aagatccaat tcttgaaccc aattcacttg   3720
accgaaaaca agttgcaaac cttgcaatct tctttcgaac ctatcgttac taagaagtct   3780
gccttctctg ttaacttctt catcaaggat accgtcgagg atcaatctaa ggttaagtct   3840
atgtctgacg aaacttggac taacacttgt aaggctacca tttccttgga acaacaacag   3900
ccatctccat cttctacttt gactttgtct aagaagcaag acttgcagat cttgagaaac   3960
agatgcgata ttagcaagct agacaagttt gagttgtacg acaagatctc taagaatttg   4020
ggcttgcagt acaactcctt gtttcaagtt gttgatacca tcgaaactgg taaggattgc   4080
tcttttgcta ctttgtcttt gccagaagat actttgttca ccaccatttt gaacccatgc   4140
ttgttggata actgtttcca tggtttgttg accttgatca acgaaaaggg ttctttcgtt   4200
gtcgagtcca tttcttctgt ttctatctac ttggagaaca tcggttcctt caatcaaact   4260
tctgttggta acgtccagtt ctacttgtac accactattt ctaaagccac ctcctttagt   4320
tctgaaggta cttgtaagtt gttcaccaag gatggttcct tgattttgtc tatcggtaag   4380
ttcatcatca agtccaccaa tccaaagtct actaagacca acgaaactat cgaatctcca   4440
ttggacgaaa ccttctctat tgaatggcaa tctaaggatt ctccaattcc aaccccacaa   4500
```

```
caaatccaac aacaatctcc attgaactct aacccatcct tcattagatc taccatcttg   4560
aaggacatcc agttcgaaca atactgctcc tccattatcc acaaagaatt gatcaaccac   4620
gaaaagtaca agaaccagca atccttcgat atcaactcct tggaaaacca cttgaacgat   4680
gaccaattga tggaatcctt gtccatctcc aaagaatact tgagattctt caccaggatc   4740
atctccatca ttaagcaata cccaaagatc ttgaacgaaa aagagctaaa agaattgaaa   4800
gaaatcatcg aattgaagta cccatccgaa gttcagttgt tggaattcga agttatcgag   4860
aaggtgtcca tgattatccc aaagttgttg ttcgaaaacg acaagcaatc ttccatgacc   4920
ttgttccaag ataacttgtt gaccaggttc tactccaatt ctaactctac cagattctac   4980
ttggaaaggg tttccgaaat ggtcttggaa tctattagac caatcgtcag agaaaagagg   5040
gtgttcagaa ttttagagat cggtgctcgt acaggctctt tgtctaatgt tgttttgact   5100
aagttgaaca cctacttgtc caccttgaat tctaatggtg gttctggtta caacatcatc   5160
attgagtaca ccttcaccga tatttccgcc aacttcatta ttggtgaaat ccaagaaacc   5220
atgtgcaact tgtacccaaa cgttactttc aagttctccg tcttggactt ggagaaagag   5280
attattaact cctccgattt cttgatgggt gattacgata tagttttgat ggcctacgtt   5340
atccatgccg tttctaacat taagttctcc atcgaacagt tgtacaagtt gttgtctcca   5400
agaggttggt tgttgtgtat tgaacctaag tccaacgttg tgttctccga tttggttttc   5460
ggttgtttta atcagtggtg gaactactac gatgatatta gaactaccca ctgctccttg   5520
tctgaatctc aatggaatca gttgttgttg aaccagtcct tgaacaacga atcctcttct   5580
tcttctaact gttacggtgg tttctccaac gtttctttta ttggtggtga aaaggatgtc   5640
gactcccatt ctttcatatt gcactgccaa aaagaatcca tctcccaaat gaagttagcc   5700
accactatta acaacggttt gtcatctggt tccatcgtta tcgttttgaa ctctcaacaa   5760
ttgaccaaca tgaagtccta cccaaaggtt attgagtata ttcaagaggc tacctctttg   5820
tgcaagacca ttgaaattat cgattccaag gacgtcttga actctaccaa ttcagttttg   5880
gaaaagatcc aaaagtcctt gttggtgttc tgtttgttgg gttatgactt gttggagaac   5940
aactaccaag aacagtcttt cgaatacgtt aagttgttga acttgatctc tactaccgcc   6000
tcttcatcta atgataagaa accaccaaag gtcttgttga tcaccaagca atctgaaaga   6060
atctccaggt ctttctactc cagatccttg attggtattt ccagaacctc tatgaacgag   6120
tacccaaatt tgtccattac ctctatcgat ttggatacca acgactactc attgcagtct   6180
ttgttgaagc caatcttcag caactctaag ttttccgaca acgagttcat cttcaaaaag   6240
ggcttgatgt tcgtgtccag gatctttaag aacaagcagt tgctagaatc ctccaacgct   6300
tttgaaactg actcttctaa cttgtactgt aaggcctctt ctgacttgtc ttacaagtac   6360
gctattaagc agtctatgtt gaccgaaaat cagatcgaaa tcaaggttga atgcgtcggt   6420
attaacttca aggacaacct attctacaag ggcttgttgc cacaagaaat tttcagaatg   6480
ggtgacatct acaatccacc atatggtttg gaatgctctg gtgttattac cagaattggt   6540
tctaacgtca ccgaatactc agttggtcaa aatgtttttg gtttcgccag acattctttg   6600
ggttctcatg ttgttaccaa caaggatttg gttatcttga agccagatac catctcattt   6660
tctgaagctg cttctatccc agttgtttac tgtactgctt ggtactcctt gttcaacatt   6720
ggtcagttgt ctaacgaaga atccatccta attcattctg ctactggtgg tgtaggtttg   6780
gcttctttga atttgttgaa aatgaagaat cagcaacagc aaccattgac caatgtttat   6840
```

```
gctactgttg gctctaacga gaagaagaag ttcttgatcg ataacttcaa caacttgttc   6900
aaagaggacg gcgaaaacat ttctctacc agagacaaag aatactccaa ccagttggaa    6960
tccaagatcg atgttatttt gaacaccttg tccggtgaat tcgtcgaatc taatttcaag   7020
tccttgagat ccttcggtag attgattgat ttgtctgcta ctcacgttta cgccaatcaa   7080
caaattggtc taggtaactt caagttcgac cacttgtatt ctgctgttga cttggaaaga   7140
ttgatcgacg aaaaacctaa gttgttgcag tccatcttgc aaagaattac caactctatc   7200
gtcaacggtt ccttggaaaa aattccaatt accatcttcc catccaccga aactaaggat   7260
gctatcgaat tattgtccaa gagatcccat atcggtaaag ttgttgtaga ttgcaccgat   7320
atctctaagt gtaatcctgt tggtgatgtg atcaccaact tctctatgag attgccaaag   7380
ccaaactacc agttgaattt gaactccacc ttgttgatta ctggtcagtc tggtttgtct   7440
atccctttgt tgaattggtt gttgtctaag tctggtggta acgttaagaa cgttgtcatc   7500
atttctaagt ccaccatgaa gtggaagttg cagactatga tttcccattt cgtttccggt   7560
ttcggtatcc attttaacta cgttcaagtc gacatctcca actacgatgc tttgtctgaa   7620
gctattaagc aattgccatc tgatttgcca ccaatcacct ctgtttttca tttggctgct   7680
atctacaacg atgttccaat ggatcaagtt accatgtcta ccgttgaatc tgttcataac   7740
cctaaagttt tgggtgccgt taacttgcat agaatctctg tttcttttgg ttggaagttg   7800
aaccacttcg tcttgttctc ttctattact gctattaccg gttacccaga ccaatctatc   7860
tacaattctg ccaactctat tttggacgct ttgtccaact ttagaaggtt tatgggtttg   7920
ccatccttct ccattaactt gggtccaatg aaggatgaag gtaaggtttc taccaacaag   7980
agcatcaaga agctattcaa gtctagaggt ttgccaagcc tatccttgaa caagttattt   8040
ggtttgttgg aggtcgtcat caacaaccca tctaatcatg ttatcccatc ccaattgatt   8100
tgctccccaa tcgatttcaa gacctacatc gaatctttct caactatgag gccaaagttg   8160
ttacacttgc aacctaccat ttccaagcag caatcttcta tcattaacga ttctaccaag   8220
gcttcctcca acatttcatt gcaagataag atcacctcca aggtgtctga tttgttgtcc   8280
attccaatct ccaagatcaa cttcgatcat ccattgaaac actacggctt ggattctttg   8340
ttgaccgttc aattcaaatc ctggatcgac aaagaattcg aaaagaactt gttcacccat   8400
atccaattgg ccaccatctc tattaactca ttcttggaaa aggtgaacgg cttgtctaca   8460
aacaataaca acaacaacaa ttccaacgtc aagtcctctc catccattgt caaagaagaa   8520
atcgttacct tggacaagga tcaacaacca ttgctattga aagaacacca gcacattatc   8580
atctccccag atattagaat caacaagcca aagagggaat ccttgattag aaccccaatc   8640
ttgaacaaat tcaaccagat caccgaatcc attatcactc catctacacc atctttgtcc   8700
caatccgatg ttttgaaaac tccaccaatc aagtctttga acaacactaa gaactccagc   8760
ttgattaaca ccccaccaat tcaatctgtc caacaacatc aaaagcaaca acaaaaggtc   8820
caagtcatcc aacaacagca acaaccatta tccagattgt cctacaagag caacaacaac   8880
tctttcgttt tgggtatcgg tatttctgtt ccaggtgaac ctatttccca acaatccttg   8940
aaagactcca tctccaatga cttttctgat aaggctgaaa ctaacgagaa ggtcaagaga   9000
atctttgagc aatctcaaat caagaccaga cacttggtta gagattacac taagccagag   9060
aactccatca agttcagaca tttggaaacc attaccgatg tgaacaacca gttcaagaaa   9120
gttgttccag atttggctca acaagcctgt ttgagagctt tgaaagattg gggtggtgat   9180
aagggtgata ttacccatat agtttctgtt acctccaccg gtattatcat cccagatgtt   9240
```

```
aatttcaagt tgatcgactt gttgggcttg aacaaggatg ttgaaagagt gtctttgaac   9300

ctaatgggtt gtttggctgg tttgagttct ttgagaactg ctgcttcttt ggctaaggct   9360

tctccaagaa atagaatttt ggttgtctgt accgaagtct gctccttgca tttttctaat   9420

actgatggtg gtgatcaaat ggtcgcctct tctatttttg ctgatggttc tgctgcttac   9480

attattggtt gtaacccaag aattgaagaa accccattat acgaagtcat gtgctccatt   9540

aacagatctt tcccaaatac cgaaaacgcc atggtttggg atttggaaaa agaaggttgg   9600

aacttgggtt tggatgcttc tattccaatt gtcattggtt ctggtattga agccttcgtt   9660

gatactttgt tggataaggc taagttgcaa acttccactg ctatttctgc taaggattgc   9720

gaattcttga ttcatactgg tggcaagtcc atcttgatga acatcgaaaa ttccttgggt   9780

atcgacccaa agcaaactaa gaatacttgg gatgtttacc atgcctacgg caatatgtca   9840

tctgcctctg ttattttcgt tatggatcat gccagaaagt ccaagtcttt gccaacttac   9900

tcaatttctt tggcttttgg tccaggtttg gcttttgaag gttgtttctt gaagaacgtc   9960

gtctaaagac ataaaactga aacaacacca attaataata gactttacag aagacgggag  10020

acactagcac acaactttac caggcaaggt atttgacgct agcatgtgtc caattcagtg  10080

tcatttatga ttttttgtag taggatataa atatatacag cgctccaaat agtgcggttg  10140

ccccaaaaac accacggaac ctcatctgtt ctcgtacttt gttgtgacaa agtagctcac  10200

tgccttatta tcacattttc attatgcaac gcttcggaaa atacgatgtt gaaaatgcct  10260

ctagagatga aaaacaatcg taaaagggtc ctgcgtaatt gaaacatttg atcagtatgc  10320

agtggcacag aaacaaccag gaatactata gtcataggca atacaaggta tatattggct  10380

atgcagaccc ctccagaaag taccgacgtc aagttagata cacttaacga acctagtgca  10440

catttaattg agaaaaatgt ggctcttcct aaggacatat tccgttcgta cttgagttat  10500

tggatctatg aaatcgctcg ctatacacca gtcatgattt tgtccctctt tatattacat  10560

caaaataaga aaataattat aaca                                         10584
```

<210> SEQ ID NO 11
<211> LENGTH: 6034
<212> TYPE: DNA
<213> ORGANISM: Artificial Sequence
<220> FEATURE:
<223> OTHER INFORMATION: Plasmid
<220> FEATURE:
<221> NAME/KEY: LV5
<222> LOCATION: (1)..(40)
<220> FEATURE:
<221> NAME/KEY: pYES2-LEU2
<222> LOCATION: (1915)..(4123)
<220> FEATURE:
<221> NAME/KEY: LEU2 ORF
<222> LOCATION: (1996)..(3090)
<220> FEATURE:
<221> NAME/KEY: LEU2 promoter
<222> LOCATION: (3091)..(3999)
<220> FEATURE:
<221> NAME/KEY: misc_feature
<222> LOCATION: (3759)..(3760)
<223> OTHER INFORMATION: n is a, c, g, or t
<220> FEATURE:
<221> NAME/KEY: LV3
<222> LOCATION: (5995)..(6034)

<400> SEQUENCE: 11

```
cctctttata ttacatcaaa ataagaaaat aattataaca cctgcattaa tgaatcggcc     60

aacgcgcggg gagaggcggt ttgcgtattg ggcgctcttc cgcttcctcg ctcactgact    120
```

```
cgctgcgctc ggtcgttcgg ctgcggcgag cggtatcagc tcactcaaag gcggtaatac    180
ggttatccac agaatcaggg gataacgcag gaaagaacat gtgagcaaaa ggccagcaaa    240
agcccaggaa ccgtaaaaag gccgcgttgc tggcgttttt ccataggctc cgcccccctg    300
acgagcatca caaaaatcga cgctcaagtc agaggtggcg aaacccgaca ggactataaa    360
gataccaggc gtttccccct ggaagctccc tcgtgcgctc tcctgttccg accctgccgc    420
ttaccggata cctgtccgcc tttctccctt cgggaagcgt ggcgctttct catagctcac    480
gctgtaggta tctcagttcg gtgtaggtcg ttcgctccaa gctgggctgt gtgcacgaac    540
cccccgttca gcccgaccgc tgcgccttat ccggtaacta tcgtcttgag tccaacccgg    600
taagacacga cttatcgcca ctggcagcag ccactggtaa caggattagc agagcgaggt    660
atgtaggcgg tgctacagag ttcttgaagt ggtggcctaa ctacggctac actagaagga    720
cagtatttgg tatctgcgct ctgctgaagc cagttacctt cggaaaaaga gttggtagct    780
cttgatccgg caaacaaacc accgctggta gcggtggttt ttttgtttgc aagcagcaga    840
ttacgcgcag aaaaaaagga tctcaagaag atcctttgat cttttctacg gggtctgacg    900
ctcagtggaa cgaaaactca cgttaaggga ttttggtcat gagattatca aaaaggatct    960
tcacctagat ccttttaaat taaaaatgaa gttttaaatc aatctaaagt atatatgagt   1020
aaacttggtc tgacagttac caatgcttaa tcagtgaggc acctatctca gcgatctgtc   1080
tatttcgttc atccatagtt gcctgactcc ccgtcgtgta gataactacg atacgggagc   1140
gcttaccatc tggccccagt gctgcaatga taccgcgaga cccacgctca ccggctccag   1200
atttatcagc aataaaccag ccagccggaa gggccgagcg cagaagtggt cctgcaactt   1260
tatccgcctc cattcagtct attaattgtt gccgggaagc tagagtaagt agttcgccag   1320
ttaatagttt gcgcaacgtt gttggcattg ctacaggcat cgtggtgtca ctctcgtcgt   1380
ttggtatggc ttcattcagc tccggttccc aacgatcaag gcgagttaca tgatccccca   1440
tgttgtgcaa aaaagcggtt agctccttcg gtcctccgat cgttgtcaga agtaagttgg   1500
ccgcagtgtt atcactcatg gttatggcag cactgcataa ttctcttact gtcatgccat   1560
ccgtaagatg cttttctgtg actggtgagt actcaaccaa gtcattctga gaatagtgta   1620
tgcggcgacc gagttgctct tgcccggcgt caatacggga taatagtgta tcacatagca   1680
gaactttaaa agtgctcatc attggaaaac gttcttcggg gcgaaaactc tcaaggatct   1740
taccgctgtt gagatccagt tcgatgtaac ccactcgtgc acccaactga tcttcagcat   1800
cttttacttt caccagcgtt tctgggtgag caaaaacagg aaggcaaaat gccgcaaaaa   1860
agggaataag ggcgacacgg aaatgttgaa tactcatact cttccttttt caatgggtaa   1920
taactgatat aattaaattg aagctctaat ttgtgagttt agtatacatg catttactta   1980
taatacagtt ttttattaag caaggatttt cttaacttct tcggcgacag catcaccgac   2040
ttcggtggta ctgttggaac cacctaaatc accagttctg atacctgcat ccaaaacctt   2100
tttaactgca tcttcaatgg ccttaccttc ttcaggcaag ttcaatgaca atttcaacat   2160
cattgcagca gacaagatag tggcgatagg gttgacctta ttctttggca aatctggagc   2220
agaaccgtgg catggttcgt acaaaccaaa tgcggtgttc ttgtctggca aagaggccaa   2280
ggacgcagat ggcaacaaac ccaaggaacc tgggataacg gaggcttcat cggagatgat   2340
atcaccaaac atgttgctgg tgattataat accatttagg tgggttgggt tcttaactag   2400
gatcatggcg gcagaatcaa tcaattgatg ttgaaccttc aatgtaggga attcgttctt   2460
```

```
gatggtttcc tccacagttt ttctccataa tcttgaagag gccaaaacat tagctttatc   2520
caaggaccaa ataggcaatg gtggctcatg ttgtagggcc atgaaagcgg ccattcttgt   2580
gattctttgc acttctggaa cggtgtattg ttcactatcc caagcgacac catcaccatc   2640
gtcttccttt ctcttaccaa agtaaatacc tcccactaat tctctgacaa caacgaagtc   2700
agtaccttta gcaaattgtg gcttgattgg agataagtct aaaagagagt cggatgcaaa   2760
gttacatggt cttaagttgg cgtacaattg aagttcttta cggattttta gtaaaccttg   2820
ttcaggtcta acactaccgg taccccattt aggaccaccc acagcaccta acaaaacggc   2880
atcagccttc ttggaggctt ccagcgcctc atctggaagt ggaacacctg tagcatcgat   2940
agcagcacca ccaattaaat gattttcgaa atcgaacttg acattggaac gaacatcaga   3000
aatagcttta agaaccttaa tggcttcggc tgtgatttct tgaccaacgt ggtcacctgg   3060
caaaacgacg atcttcttag gggcagacat tagaatggta tatccttgaa atatatatat   3120
atattgctga aatgtaaaag gtaagaaaag ttagaaagta agacgattgc taaccaccta   3180
ttggaaaaaa caataggtcc ttaaataata ttgtcaactt caagtattgt gatgcaagca   3240
tttagtcatg aacgcttctc tattctatat gaaaagccgg ttccggcgct ctcacctttc   3300
ctttttctcc caatttttca gttgaaaaag gtatatgcgt caggcgacct ctgaaattaa   3360
caaaaaattt ccagtcatcg aatttgattc tgtgcgatag cgcccctgtg tgttctcgtt   3420
atgttgagga aaaaaataat ggttgctaag agattcgaac tcttgcatct tacgatacct   3480
gagtattccc acagttaact gcggtcaaga tatttcttga atcaggcgcc ttagaccgct   3540
cggccaaaca accaattact tgttgagaaa tagagtataa ttatcctata aatataacgt   3600
ttttgaacac acatgaacaa ggaagtacag gacaattgat tttgaagaga atgtggattt   3660
tgatgtaatt gttgggattc catttttaat aaggcaataa tattaggtat gtagatatac   3720
tagaagttct cctcgaggat ttaggaatcc ataaaaggnn atctgcaatt ctacacaatt   3780
ctagaaatat tattatcatc attttatatg ttaatattca ttgatcctat tacattatca   3840
atccttgcgt ttcagcttcc actaatttag atgactattt ctcatcattt gcgtcatctt   3900
ctaacaccgt atatgataat atactagtaa cgtaaatact agttagtaga tgatagttga   3960
tttttattcc aacataccac ccataatgta atagatctag cttatcgatg ataagctgtc   4020
aaagatgaga attaattcca cggactatag actataccta gtatactccg tctactgtac   4080
gatacacttc cgctcaggtc cttgtccttt aacgaggcct taccactctt ttgttactct   4140
attgatccag ctcagcaaag gcagtgtgat ctaagattct atcttcgcga tgtagtaaaa   4200
ctagctagac cgagaaagag actagaaatg caaaaggcac ttctacaatg gctgccatca   4260
ttattatccg atgtgacgct gcagcttctc aatgatattc gaatacgctt tgaggagata   4320
cagcctaata tccgacaaac tgttttacag atttacgatc gtacttgtta cccatcattg   4380
aattttgaac atccgaacct gggagttttc cctgaaacag atagtatatt tgaacctgta   4440
taataatata tagtctagcg ctttacggaa gacaatgtat gtatttcggt tcctggagaa   4500
actattgcat ctattgcata ggtaatcttg cacgtcgcat ccccggttca ttttctgcgt   4560
ttccatcttg cacttcaata gcatatcttt gttaacgaag catctgtgct tcattttgta   4620
gaacaaaaat gcaacgcgag agcgctaatt tttcaaacaa agaatctgag ctgcattttt   4680
acagaacaga aatgcaacgc gaaagcgcta ttttaccaac gaagaatctg tgcttcattt   4740
ttgtaaaaca aaaatgcaac gcgacgagag cgctaatttt tcaaacaaag aatctgagct   4800
gcatttttac agaacagaaa tgcaacgcga gagcgctatt ttaccaacaa agaatctata   4860
```

```
cttcttttt gttctacaaa aatgcatccc gagagcgcta tttttctaac aaagcatctt   4920

agattacttt ttttctcctt tgtgcgctct ataatgcagt ctcttgataa ctttttgcac   4980

tgtaggtccg ttaaggttag aagaaggcta ctttggtgtc tattttctct tccataaaaa   5040

aagcctgact ccacttcccg cgtttactga ttactagcga agctgcgggt gcattttttc   5100

aagataaagg catccccgat tatattctat accgatgtgg attgcgcata ctttgtgaac   5160

agaaagtgat agcgttgatg attcttcatt ggtcagaaaa ttatgaacgg tttcttctat   5220

tttgtctcta tatactacgt ataggaaatg tttacatttt cgtattgttt tcgattcact   5280

ctatgaatag ttcttactac aatttttttg tctaaagagt aatactagag ataaacataa   5340

aaaatgtaga ggtcgagttt agatgcaagt tcaaggagcg aaaggtggat gggtaggtta   5400

tatagggata tagcacagag atatatagca aagagatact tttgagcaat gtttgtggaa   5460

gcggtattcg caatgggaag ctccaccccg gttgataatc agaaaagccc caaaaacagg   5520

aagattgtat aagcaaatat ttaaattgta aacgttaata ttttgttaaa attcgcgtta   5580

aatttttgtt aaatcagctc attttttaac gaatagcccg aaatcggcaa aatcccttat   5640

aaatcaaaag aatagaccga gatagggttg agtgttgttc cagtttccaa caagagtcca   5700

ctattaaaga acgtggactc caacgtcaaa gggcgaaaaa gggtctatca gggcgatggc   5760

ccactacgtg aaccatcacc ctaatcaagt tttttggggt cgaggtgccg taaagcagta   5820

aatcggaagg gtaaacggat gcccccattt agagcttgac ggggaaagcc ggcgaacgtg   5880

gcgagaaagg aagggaagaa agcgaaagga gcgggggcta gggcggtggg aagtgtaggg   5940

gtcacgctgg gcgtaaccac cacacccgcc gcgcttaatg gggcgctaca gggcaggaat   6000

actctgaata aaacaactta tataataaaa atgc                                6034
```

<210> SEQ ID NO 12
<211> LENGTH: 5056
<212> TYPE: DNA
<213> ORGANISM: Artificial Sequence
<220> FEATURE:
<223> OTHER INFORMATION: Plasmid
<220> FEATURE:
<221> NAME/KEY: LV5
<222> LOCATION: (1)..(40)
<220> FEATURE:
<221> NAME/KEY: pYES backbone
<222> LOCATION: (41)..(5016)
<220> FEATURE:
<221> NAME/KEY: AmpR
<222> LOCATION: (1040)..(1699)
<220> FEATURE:
<221> NAME/KEY: URA3
<222> LOCATION: (1915)..(3022)
<220> FEATURE:
<221> NAME/KEY: LV3
<222> LOCATION: (5017)..(5056)

<400> SEQUENCE: 12

```
cctctttata ttacatcaaa ataagaaaat aattataaca cctgcattaa tgaatcggcc     60

aacgcgcggg gagaggcggt ttgcgtattg ggcgctcttc cgcttcctcg ctcactgact    120

cgctgcgctc ggtcgttcgg ctgcggcgag cggtatcagc tcactcaaag gcggtaatac    180

ggttatccac agaatcaggg gataacgcag gaaagaacat gtgagcaaaa ggccagcaaa    240

agcccaggaa ccgtaaaaag gccgcgttgc tggcgttttt ccataggctc cgcccccctg    300

acgagcatca caaaaatcga cgctcaagtc agaggtggcg aaacccgaca ggactataaa    360

gataccaggc gtttccccct ggaagctccc tcgtgcgctc tcctgttccg accctgccgc    420
```

```
ttaccggata cctgtccgcc tttctccctt cgggaagcgt ggcgctttct catagctcac    480

gctgtaggta tctcagttcg gtgtaggtcg ttcgctccaa gctgggctgt gtgcacgaac    540

ccccccgttca gcccgaccgc tgcgccttat ccggtaacta tcgtcttgag tccaacccgg    600

taagacacga cttatcgcca ctggcagcag ccactggtaa caggattagc agagcgaggt    660

atgtaggcgg tgctacagag ttcttgaagt ggtggcctaa ctacggctac actagaagga    720

cagtatttgg tatctgcgct ctgctgaagc cagttacctt cggaaaaaga gttggtagct    780

cttgatccgg caaacaaacc accgctggta gcggtggttt ttttgtttgc aagcagcaga    840

ttacgcgcag aaaaaaagga tctcaagaag atcctttgat cttttctacg gggtctgacg    900

ctcagtggaa cgaaaactca cgttaaggga ttttggtcat gagattatca aaaaggatct    960

tcacctagat ccttttaaat taaaaatgaa gttttaaatc aatctaaagt atatatgagt   1020

aaacttggtc tgacagttac caatgcttaa tcagtgaggc acctatctca gcgatctgtc   1080

tatttcgttc atccatagtt gcctgactcc ccgtcgtgta gataactacg atacgggagc   1140

gcttaccatc tggccccagt gctgcaatga taccgcgaga cccacgctca ccggctccag   1200

atttatcagc aataaaccag ccagccggaa gggccgagcg cagaagtggt cctgcaactt   1260

tatccgcctc cattcagtct attaattgtt gccgggaagc tagagtaagt agttcgccag   1320

ttaatagttt gcgcaacgtt gttggcattg ctacaggcat cgtggtgtca ctctcgtcgt   1380

ttggtatggc ttcattcagc tccggttccc aacgatcaag gcgagttaca tgatccccca   1440

tgttgtgcaa aaaagcggtt agctccttcg gtcctccgat cgttgtcaga agtaagttgg   1500

ccgcagtgtt atcactcatg gttatggcag cactgcataa ttctcttact gtcatgccat   1560

ccgtaagatg cttttctgtg actggtgagt actcaaccaa gtcattctga gaatagtgta   1620

tgcggcgacc gagttgctct tgcccggcgt caatacggga taatagtgta tcacatagca   1680

gaactttaaa agtgctcatc attggaaaac gttcttcggg gcgaaaactc tcaaggatct   1740

taccgctgtt gagatccagt tcgatgtaac ccactcgtgc acccaactga tcttcagcat   1800

cttttacttt caccagcgtt tctgggtgag caaaaacagg aaggcaaaat gccgcaaaaa   1860

agggaataag ggcgacacgg aaatgttgaa tactcatact cttccttttt caatgggtaa   1920

taactgatat aattaaattg aagctctaat ttgtgagttt agtatacatg catttactta   1980

taatacagtt ttttagtttt gctggccgca tcttctcaaa tatgcttccc agcctgcttt   2040

tctgtaacgt tcaccctcta ccttagcatc ccttcccttt gcaaatagtc ctcttccaac   2100

aataataatg tcagatcctg tagagaccac atcatccacg gttctatact gttgacccaa   2160

tgcgtctccc ttgtcatcta aacccacacc gggtgtcata atcaaccaat cgtaaccttc   2220

atctcttcca cccatgtctc tttgagcaat aaagccgata acaaaatctt tgtcgctctt   2280

cgcaatgtca acagtaccct tagtatattc tccagtagat agggagccct tgcatgacaa   2340

ttctgctaac atcaaaaggc ctctaggttc ctttgttact tcttctgccg cctgcttcaa   2400

accgctaaca atacctgggc ccaccacacc gtgtgcattc gtaatgtctg cccattctgc   2460

tattctgtat acacccgcag agtactgcaa tttgactgta ttaccaatgt cagcaaattt   2520

tctgtcttcg aagagtaaaa aattgtactt ggcggataat gcctttagcg gcttaactgt   2580

gccctccatg gaaaaatcag tcaagatatc cacatgtgtt tttagtaaac aaattttggg   2640

acctaatgct tcaactaact ccagtaattc cttggtggta cgaacatcca atgaagcaca   2700

caagtttgtt tgcttttcgt gcatgatatt aaatagcttg gcagcaacag gactaggatg   2760
```

-continued

```
agtagcagca cgttccttat atgtagcttt cgacatgatt tatcttcgtt tcctgcaggt   2820
ttttgttctg tgcagttggg ttaagaatac tgggcaattt catgtttctt caacactaca   2880
tatgcgtata tataccaatc taagtctgtg ctccttcctt cgttcttcct tctgttcgga   2940
gattaccgaa tcaaaaaaat ttcaaagaaa ccgaaatcaa aaaaaagaat aaaaaaaaaa   3000
tgatgaattg aattgaaaag ctagcttatc gatgataagc tgtcaaagat gagaattaat   3060
tccacggact atagactata ctagatactc cgtctactgt acgatacact tccgctcagg   3120
tccttgtcct ttaacgaggc cttaccactc ttttgttact ctattgatcc agctcagcaa   3180
aggcagtgtg atctaagatt ctatcttcgc gatgtagtaa aactagctag accgagaaag   3240
agactagaaa tgcaaaaggc acttctacaa tggctgccat cattattatc cgatgtgacg   3300
ctgcagcttc tcaatgatat tcgaatacgc tttgaggaga tacagcctaa tatccgacaa   3360
actgttttac agatttacga tcgtacttgt tacccatcat tgaattttga acatccgaac   3420
ctgggagttt tccctgaaac agatagtata tttgaacctg tataataata tatagtctag   3480
cgctttacgg aagacaatgt atgtatttcg gttcctggag aaactattgc atctattgca   3540
taggtaatct tgcacgtcgc atccccggtt cattttctgc gtttccatct tgcacttcaa   3600
tagcatatct ttgttaacga agcatctgtg cttcattttg tagaacaaaa atgcaacgcg   3660
agagcgctaa tttttcaaac aaagaatctg agctgcattt ttacagaaca gaaatgcaac   3720
gcgaaagcgc tattttacca acgaagaatc tgtgcttcat ttttgtaaaa caaaaatgca   3780
acgcgacgag agcgctaatt tttcaaacaa agaatctgag ctgcattttt acagaacaga   3840
aatgcaacgc gagagcgcta ttttaccaac aaagaatcta tacttctttt ttgttctaca   3900
aaaatgcatc ccgagagcgc tatttttcta acaaagcatc ttagattact ttttttctcc   3960
tttgtgcgct ctataatgca gtctcttgat aactttttgc actgtaggtc cgttaaggtt   4020
agaagaaggc tactttggtg tctattttct cttccataaa aaaagcctga ctccacttcc   4080
cgcgtttact gattactagc gaagctgcgg gtgcattttt tcaagataaa ggcatccccg   4140
attatattct ataccgatgt ggattgcgca tactttgtga acagaaagtg atagcgttga   4200
tgattcttca ttggtcagaa aattatgaac ggtttcttct attttgtctc tatatactac   4260
gtataggaaa tgtttacatt ttcgtattgt tttcgattca ctctatgaat agttcttact   4320
acaatttttt tgtctaaaga gtaatactag agataaacat aaaaaatgta gaggtcgagt   4380
ttagatgcaa gttcaaggag cgaaaggtgg atgggtaggt tatataggga tatagcacag   4440
agatatatag caaagagata cttttgagca atgtttgtgg aagcggtatt cgcaatggga   4500
agctccaccc cggttgataa tcagaaaagc cccaaaaaca ggaagattgt ataagcaaat   4560
atttaaattg taaacgttaa tattttgtta aaattcgcgt taaatttttg ttaaatcagc   4620
tcatttttta acgaatagcc cgaaatcggc aaaatccctt ataaatcaaa agaatagacc   4680
gagatagggt tgagtgttgt tccagtttcc aacaagagtc cactattaaa gaacgtggac   4740
tccaacgtca aagggcgaaa aagggtctat cagggcgatg gcccactacg tgaaccatca   4800
ccctaatcaa gtttttttggg gtcgaggtgc cgtaaagcag taaatcggaa gggtaaacgg   4860
atgcccccat ttagagcttg acggggaaag ccggcgaacg tggcgagaaa ggaagggaag   4920
aaagcgaaag gagcgggggc tagggcggtg ggaagtgtag gggtcacgct gggcgtaacc   4980
accacacccg ccgcgcttaa tggggcgcta cagggcagga atactctgaa taaaacaact   5040
tatataataa aaatgc                                                   5056
```

<210> SEQ ID NO 13
<211> LENGTH: 10584
<212> TYPE: DNA
<213> ORGANISM: Artificial Sequence
<220> FEATURE:
<223> OTHER INFORMATION: Cassette with Dictyostelium discoideum DiPKS coding sequence, regulatory sequences and integration sequences
<220> FEATURE:
<221> NAME/KEY: LV3
<222> LOCATION: (1)..(40)
<220> FEATURE:
<221> NAME/KEY: S. cerevisiae GAL1 promoter
<222> LOCATION: (41)..(482)
<220> FEATURE:
<221> NAME/KEY: L1
<222> LOCATION: (483)..(522)
<220> FEATURE:
<221> NAME/KEY: DiPKS
<222> LOCATION: (523)..(9966)
<220> FEATURE:
<221> NAME/KEY: Motif 1
<222> LOCATION: (5050)..(5076)
<220> FEATURE:
<221> NAME/KEY: C-methyltransferase domain
<222> LOCATION: (5050)..(5412)
<220> FEATURE:
<221> NAME/KEY: Motif 2
<222> LOCATION: (5309)..(5331)
<220> FEATURE:
<221> NAME/KEY: Motif 3
<222> LOCATION: (5389)..(5421)
<220> FEATURE:
<221> NAME/KEY: L2
<222> LOCATION: (9967)..(10006)
<220> FEATURE:
<221> NAME/KEY: PRM9t
<222> LOCATION: (10007)..(10544)
<220> FEATURE:
<221> NAME/KEY: LV5
<222> LOCATION: (10545)..(10584)

<400> SEQUENCE: 13
aggaatactc tgaataaaac aacttatata ataaaaatgc cggattagaa gccgccgagc 60
gggtgacagc cctccgaagg aagactctcc tccgtgcgtc ctcgtcttca ccggtcgcgt 120
tcctgaaacg cagatgtgcc tcgcgccgca ctgctccgaa caataaagat tctacaatac 180
tagcttttat ggttatgaag aggaaaaatt ggcagtaacc tggccccaca aaccttcaaa 240
tgaacgaatc aaattaacaa ccataggatg ataatgcgat tagtttttta gccttatttc 300
tggggtaatt aatcagcgaa gcgatgattt ttgatctatt aacagatata taaatgcaaa 360
aactgcataa ccactttaac taatactttc aacattttcg gtttgtatta cttcttattc 420
aaatgtaata aaagtatcaa caaaaaattg ttaatatacc tctatacttt aacgtcaagg 480
agctagaaaa tttattataa aaggaagaga aataattaaa caatgaacaa gaactccaaa 540
atccagtccc caaactcttc tgatgttgct gttattggtg ttggttttag attcccaggt 600
aactctaatg acccagaatc tttgtggaac aacttgttgg atggtttcga tgctattacc 660
caagtcccaa aagaaagatg ggctacttct tttagagaga tgggtttgat caagaacaag 720
ttcggtggtt tcttgaagga ttctgaatgg aagaatttcg accctttgtt ctttggtatc 780
ggtccaaaag aagctccatt cattgatcca caacaaaggt tgttgttgtc catcgtttgg 840
gaatctttgg aagatgctta catcagacca gatgaattga gaggttctaa cactggtgtt 900
ttcatcggtg tttctaacaa cgattacacc aagttgggtt tccaagacaa ctactctatt 960
tctccataca ctatgaccgg ctctaactct tcattgaact ccaacagaat ttcctactgc 1020
ttcgatttta gaggtccatc cattactgtt gataccgctt gttcttcttc cttggtttct 1080

```
gttaatttgg gtgtccaatc catccaaatg ggtgaatgta agattgctat ttgcggtggt   1140

gttaacgctt tgtttgatcc atctacatct gttgcctttt ccaagttggg tgttttgtct   1200

gaaaatggca gatgcaactc ttttagtgat caagcctctg gttacgttag atctgaaggt   1260

gctggtgttg ttgttttgaa gtctttggaa caagctaagt tggatggtga tagaatctac   1320

ggtgttatca agggtgtttc ctctaatgaa gatggtgctt ctaatggtga caagaactct   1380

ttgactactc catcttgtga agcccaatcc attaacattt ctaaggctat ggaaaaggcc   1440

tccttgtctc catctgatat ctattacatt gaagcccatg gtactggtac tccagttggt   1500

gatccaattg aagttaaggc cttgtccaag atcttctcca actctaacaa caaccagttg   1560

aacaacttct ctaccgatgg taatgataac gatgatgatg atgacgataa cacctctcca   1620

gaaccattat tgattggctc attcaagtcc aacatcggtc atttggaatc tgctgctggt   1680

attgcttctt tgattaagtg ttgcttgatg ttgaagaaca ggatgttggt tccatccatt   1740

aactgctcta atttgaaccc atccattcca ttcgatcagt acaacatctc cgttatcaga   1800

gaaatcagac aattcccaac cgataagttg gttaacatcg gtatcaattc tttcggtttc   1860

ggtggttcta actgccattt gattattcaa gagtacaaca acaacttcaa gaacaactct   1920

accatctgca ataacaacaa caacaacaat aacaacatcg actacttgat cccaatctcc   1980

tctaagacta agaagtcctt ggataagtac ttgattttga tcaagaccaa ctccaactac   2040

cacaaggata tttctttcga tgacttcgtc aagttccaaa tcaagtctaa gcagtacaac   2100

ttgtccaaca gaatgactac cattgctaac gattggaact ccttcattaa gggttctaac   2160

gaattccaca acttgatcga atctaaggat ggtgaaggtg gttcttcatc ttctaacaga   2220

ggtattgatt ccgccaatca aatcaacact actactacct ctaccatcaa cgatatcgaa   2280

cctttgttgg ttttcgtttt ctgtggtcaa ggtccacaat ggaatggtat gattaagacc   2340

ttgtacaact ccgagaacgt tttcaagaac accgttgatc atgttgacag catcttgtac   2400

aagtacttcg gttactccat tttgaacgtc ttgtctaaga tcgatgataa cgacgattcc   2460

atcaaccatc caatagttgc tcaaccatct ttgttcttgt tgcaaattgg tttggtcgag   2520

ttgtttaagt actggggtat ctacccatct atctctgttg gtcattcttt cggtgaagtc   2580

tcttcttatt acttgtccgg tatcatctct ttggaaaccg cttgtaaaat cgtctacgtc   2640

agatcctcta atcagaacaa aactatgggt tccggtaaga tgttggttgt ttctatgggt   2700

tttaagcaat ggaacgatca attctctgct gaatggtccg atattgaaat tgcttgttac   2760

aacgctccag attccatagt tgttactggt aacgaagaaa gattgaaaga attgtccatc   2820

aagttgtccg acgaatccaa tcaaattttc aacaccttct tgaggtcccc atgttctttt   2880

cattcttccc atcaagaagt catcaagggt tctatgttcg aagagttgtc taacttgcaa   2940

tctactggtg aaaccgaaat ccctttgttc tctactgtta ctggtagaca agttttgtct   3000

ggtcatgtta ctgctcaaca catctacgat aatgttagag aaccagtctt gttccaaaag   3060

acgattgaat ccattacctc ctacatcaag tctcactacc catccaatca aaaggttatc   3120

tacgttgaaa ttgctccaca cccaaccttg ttttcattga tcaaaaagtc catcccatcc   3180

tccaacaaga attcctcttc tgttttgtgt ccattgaaca gaaaagaaaa ctccaacaac   3240

tcctacaaga agttcgtttc tcagttgtac ttcaacggtg ttaacgttga cttcaacttc   3300

cagttgaact ccatttgcga taacgttaac aacgatcacc atttgaacaa cgtcaagcaa   3360

aactccttca aagagactac caattccttg ccaagatacc aatgggaaca agatgaatat   3420

tggtccgaac cattgatctc cagaaagaat agattggaag gtccaactac ttccttgttg   3480
```

```
ggtcatagaa ttatctacag cttcccagtt ttccaatccg ttttggactt gcaatctgac   3540
aactacaaat acttgttgga ccacttggtt aacggtaagc cagtttttcc aggtgctggt   3600
tatttggata tcatcatcga attcttcgac taccaaaagc agcagttgaa ttcctctgat   3660
tcctctaact cctacatcat caacgttgac aagatccaat tcttgaaccc aattcacttg   3720
accgaaaaca agttgcaaac cttgcaatct tctttcgaac ctatcgttac taagaagtct   3780
gccttctctg ttaacttctt catcaaggat accgtcgagg atcaatctaa ggttaagtct   3840
atgtctgacg aaacttggac taacacttgt aaggctacca tttccttgga acaacaacag   3900
ccatctccat cttctacttt gactttgtct aagaagcaag acttgcagat cttgagaaac   3960
agatgcgata ttagcaagct agacaagttt gagttgtacg acaagatctc taagaatttg   4020
ggcttgcagt acaactcctt gtttcaagtt gttgatacca tcgaaactgg taaggattgc   4080
tcttttgcta ctttgtcttt gccagaagat actttgttca ccaccatttt gaacccatgc   4140
ttgttggata actgtttcca tggtttgttg accttgatca acgaaaaggg ttctttcgtt   4200
gtcgagtcca tttcttctgt ttctatctac ttggagaaca tcggttcctt caatcaaact   4260
tctgttggta acgtccagtt ctacttgtac accactattt ctaaagccac ctcctttagt   4320
tctgaaggta cttgtaagtt gttcaccaag gatggttcct tgattttgtc tatcggtaag   4380
ttcatcatca agtccaccaa tccaaagtct actaagacca acgaaactat cgaatctcca   4440
ttggacgaaa ccttctctat tgaatggcaa tctaaggatt ctccaattcc aaccccacaa   4500
caaatccaac aacaatctcc attgaactct aacccatcct tcattagatc taccatcttg   4560
aaggacatcc agttcgaaca atactgctcc tccattatcc acaaagaatt gatcaaccac   4620
gaaaagtaca agaaccagca atccttcgat atcaactcct tggaaaacca cttgaacgat   4680
gaccaattga tggaatcctt gtccatctcc aaagaatact tgagattctt caccaggatc   4740
atctccatca ttaagcaata cccaaagatc ttgaacgaaa aagagctaaa agaattgaaa   4800
gaaatcatcg aattgaagta cccatccgaa gttcagttgt tggaattcga agttatcgag   4860
aaggtgtcca tgattatccc aaagttgttg ttcgaaaacg acaagcaatc ttccatgacc   4920
ttgttccaag ataacttgtt gaccaggttc tactccaatt ctaactctac cagattctac   4980
ttggaaaggg tttccgaaat ggtcttggaa tctattagac caatcgtcag agaaaagagg   5040
gtgttcagaa ttttggaaat tggtgctggt acaggctctt tgtctaatgt tgttttgact   5100
aagttgaaca cctacttgtc caccttgaat tctaatggtg gttctggtta caacatcatc   5160
attgagtaca ccttcaccga tatttccgcc aacttcatta ttggtgaaat ccaagaaacc   5220
atgtgcaact tgtacccaaa cgttactttc aagttctccg tcttggactt ggagaaagag   5280
attattaact cctccgattt cttgatgggt gattacgata tagttttgat ggcctacgtt   5340
atccatgccg tttctaacat taagttctcc atcgaacagt tgtacaagtt gttgtctcca   5400
agaggttggt tgttgtgtat tgaacctaag tccaacgttg tgttctccga tttggttttc   5460
ggttgtttta atcagtggtg gaactactac gatgatatta gaactaccca ctgctccttg   5520
tctgaatctc aatggaatca gttgttgttg aaccagtcct tgaacaacga atcctcttct   5580
tcttctaact gttacggtgg tttctccaac gtttctttta ttggtggtga aaaggatgtc   5640
gactcccatt ctttcatatt gcactgccaa aaagaatcca tctcccaaat gaagttagcc   5700
accactatta acaacggttt gtcatctggt tccatcgtta tcgttttgaa ctctcaacaa   5760
ttgaccaaca tgaagtccta cccaaaggtt attgagtata ttcaagaggc tacctctttg   5820
```

-continued

```
tgcaagacca ttgaaattat cgattccaag gacgtcttga actctaccaa ttcagttttg   5880
gaaaagatcc aaaagtcctt gttggtgttc tgtttgttgg gttatgactt gttggagaac   5940
aactaccaag aacagtcttt cgaatacgtt aagttgttga acttgatctc tactaccgcc   6000
tcttcatcta atgataagaa accaccaaag gtcttgttga tcaccaagca atctgaaaga   6060
atctccaggt ctttctactc cagatccttg attggtattt ccagaacctc tatgaacgag   6120
tacccaaatt tgtccattac ctctatcgat ttggatacca acgactactc attgcagtct   6180
ttgttgaagc caatcttcag caactctaag ttttccgaca acgagttcat cttcaaaaag   6240
ggcttgatgt tcgtgtccag gatctttaag aacaagcagt tgctagaatc ctccaacgct   6300
tttgaaactg actcttctaa cttgtactgt aaggcctctt ctgacttgtc ttacaagtac   6360
gctattaagc agtctatgtt gaccgaaaat cagatcgaaa tcaaggttga atgcgtcggt   6420
attaacttca aggacaacct attctacaag ggcttgttgc cacaagaaat tttcagaatg   6480
ggtgacatct acaatccacc atatggtttg gaatgctctg gtgttattac cagaattggt   6540
tctaacgtca ccgaatactc agttggtcaa aatgtttttg gtttcgccag acattctttg   6600
ggttctcatg ttgttaccaa caaggatttg gttatcttga agccagatac catctcattt   6660
tctgaagctg cttctatccc agttgtttac tgtactgctt ggtactcctt gttcaacatt   6720
ggtcagttgt ctaacgaaga atccatccta attcattctg ctactggtgg tgtaggtttg   6780
gcttctttga atttgttgaa aatgaagaat cagcaacagc aaccattgac caatgtttat   6840
gctactgttg gctctaacga gaagaagaag ttcttgatcg ataacttcaa caacttgttc   6900
aaagaggacg gcgaaaacat tttctctacc agagacaaag aatactccaa ccagttggaa   6960
tccaagatcg atgttatttt gaacaccttg tccggtgaat tcgtcgaatc taatttcaag   7020
tccttgagat ccttcggtag attgattgat ttgtctgcta ctcacgttta cgccaatcaa   7080
caaattggtc taggtaactt caagttcgac cacttgtatt ctgctgttga cttggaaaga   7140
ttgatcgacg aaaaacctaa gttgttgcag tccatcttgc aaagaattac caactctatc   7200
gtcaacggtt ccttggaaaa aattccaatt accatcttcc catccaccga aactaaggat   7260
gctatcgaat tattgtccaa gagatcccat atcggtaaag ttgttgtaga ttgcaccgat   7320
atctctaagt gtaatcctgt tggtgatgtg atcaccaact tctctatgag attgccaaag   7380
ccaaactacc agttgaattt gaactccacc ttgttgatta ctggtcagtc tggtttgtct   7440
atccctttgt tgaattggtt gttgtctaag tctggtggta acgttaagaa cgttgtcatc   7500
atttctaagt ccaccatgaa gtggaagttg cagactatga tttcccattt cgtttccggt   7560
ttcggtatcc attttaacta cgttcaagtc gacatctcca actacgatgc tttgtctgaa   7620
gctattaagc aattgccatc tgatttgcca ccaatcacct ctgtttttca tttggctgct   7680
atctacaacg atgttccaat ggatcaagtt accatgtcta ccgttgaatc tgttcataac   7740
cctaaagttt tgggtgccgt taacttgcat agaatctctg tttcttttgg ttggaagttg   7800
aaccacttcg tcttgttctc ttctattact gctattaccg gttacccaga ccaatctatc   7860
tacaattctg ccaactctat tttggacgct ttgtccaact ttagaaggtt tatgggtttg   7920
ccatccttct ccattaactt gggtccaatg aaggatgaag gtaaggtttc taccaacaag   7980
agcatcaaga agctattcaa gtctagaggt ttgccaagcc tatccttgaa caagttattt   8040
ggtttgttgg aggtcgtcat caacaaccca tctaatcatg ttatcccatc ccaattgatt   8100
tgctccccaa tcgatttcaa gacctacatc gaatctttct caactatgag gccaaagttg   8160
ttacacttgc aacctaccat ttccaagcag caatcttcta tcattaacga ttctaccaag   8220
```

-continued

```
gcttcctcca acatttcatt gcaagataag atcacctcca aggtgtctga tttgttgtcc   8280
attccaatct ccaagatcaa cttcgatcat ccattgaaac actacggctt ggattctttg   8340
ttgaccgttc aattcaaatc ctggatcgac aaagaattcg aaaagaactt gttcacccat   8400
atccaattgg ccaccatctc tattaactca ttcttggaaa aggtgaacgg cttgtctaca   8460
aacaataaca acaacaacaa ttccaacgtc aagtcctctc catccattgt caaagaagaa   8520
atcgttacct tggacaagga tcaacaacca ttgctattga aagaacacca gcacattatc   8580
atctccccag atattagaat caacaagcca aagagggaat ccttgattag aaccccaatc   8640
ttgaacaaat tcaaccagat caccgaatcc attatcactc catctacacc atctttgtcc   8700
caatccgatg ttttgaaaac tccaccaatc aagtctttga acaacactaa gaactccagc   8760
ttgattaaca ccccaccaat tcaatctgtc caacaacatc aaaagcaaca acaaaaggtc   8820
caagtcatcc aacaacagca acaaccatta tccagattgt cctacaagag caacaacaac   8880
tctttcgttt tgggtatcgg tatttctgtt ccaggtgaac ctatttccca acaatccttg   8940
aaagactcca tctccaatga cttttctgat aaggctgaaa ctaacgagaa ggtcaagaga   9000
atctttgagc aatctcaaat caagaccaga cacttggtta gagattacac taagccagag   9060
aactccatca agttcagaca tttggaaacc attaccgatg tgaacaacca gttcaagaaa   9120
gttgttccag atttggctca acaagcctgt ttgagagctt tgaaagattg gggtggtgat   9180
aagggtgata ttacccatat agtttctgtt acctccaccg gtattatcat cccagatgtt   9240
aatttcaagt tgatcgactt gttgggcttg aacaaggatg ttgaaagagt gtctttgaac   9300
ctaatgggtt gtttggctgg tttgagttct ttgagaactg ctgcttcttt ggctaaggct   9360
tctccaagaa atagaatttt ggttgtctgt accgaagtct gctccttgca tttttctaat   9420
actgatggtg gtgatcaaat ggtcgcctct tctatttttg ctgatggttc tgctgcttac   9480
attattggtt gtaacccaag aattgaagaa accccattat acgaagtcat gtgctccatt   9540
aacagatctt tcccaaatac cgaaaacgcc atggtttggg atttggaaaa agaaggttgg   9600
aacttgggtt tggatgcttc tattccaatt gtcattggtt ctggtattga agccttcgtt   9660
gatactttgt tggataaggc taagttgcaa acttccactg ctatttctgc taaggattgc   9720
gaattcttga ttcatactgg tggcaagtcc atcttgatga acatcgaaaa ttccttgggt   9780
atcgacccaa agcaaactaa gaatacttgg gatgtttacc atgcctacgg caatatgtca   9840
tctgcctctg ttattttcgt tatggatcat gccagaaagt ccaagtcttt gccaacttac   9900
tcaatttctt tggcttttgg tccaggtttg gcttttgaag gttgtttctt gaagaacgtc   9960
gtctaaagac ataaaactga aacaacacca attaataata gactttacag aagacgggag  10020
acactagcac acaactttac caggcaaggt atttgacgct agcatgtgtc caattcagtg  10080
tcatttatga tttttttgtag taggatataa atatatacag cgctccaaat agtgcggttg  10140
ccccaaaaac accacggaac ctcatctgtt ctcgtacttt gttgtgacaa agtagctcac  10200
tgccttatta tcacattttc attatgcaac gcttcggaaa atacgatgtt gaaaatgcct  10260
ctagagatga aaaacaatcg taaaagggtc ctgcgtaatt gaaacatttg atcagtatgc  10320
agtggcacag aaacaaccag gaatactata gtcataggca atacaaggta tatattggct  10380
atgcagaccc ctccagaaag taccgacgtc aagttagata cacttaacga acctagtgca  10440
catttaattg agaaaaatgt ggctcttcct aaggacatat tccgttcgta cttgagttat  10500
tggatctatg aaatcgctcg ctatacacca gtcatgattt tgtccctctt tatattacat  10560
```

caaaataaga aaataattat aaca 10584

<210> SEQ ID NO 14
<211> LENGTH: 4909
<212> TYPE: DNA
<213> ORGANISM: Artificial Sequence
<220> FEATURE:
<223> OTHER INFORMATION: Cassette with Cas9 coding sequence, regulatory sequences and integration sequences
<220> FEATURE:
<221> NAME/KEY: LV3
<222> LOCATION: (1)..(40)
<220> FEATURE:
<221> NAME/KEY: TEF1p
<222> LOCATION: (41)..(446)
<220> FEATURE:
<221> NAME/KEY: Cas9
<222> LOCATION: (470)..(4609)
<220> FEATURE:
<221> NAME/KEY: LV5
<222> LOCATION: (4870)..(4909)

<400> SEQUENCE: 14
aggaatactc tgaataaaac aacttatata ataaaaatgc atagcttcaa aatgtttcta 60
ctcctttttt actcttccag attttctcgg actccgcgca tcgccgtacc acttcaaaac 120
acccaagcac agcatactaa atttcccctc tttcttcctc tagggtgtcg ttaattaccc 180
gtactaaagg tttggaaaag aaaaaagaga ccgcctcgtt tctttttctt cgtcgaaaaa 240
ggcaataaaa atttttatca cgtttctttt tcttgaaaat tttttttttg atttttttct 300
ctttcgatga cctcccattg atatttaagt taataaacgg tcttcaattt ctcaagtttc 360
agtttcattt ttcttgttct attacaactt tttttacttc ttgctcatta gaaagaaagc 420
atagcaatct aatctaagtt ttctagaact agtggatccc ccgggaaaaa tggacaagaa 480
gtactccatt gggctcgata tcggcacaaa cagcgtcggc tgggccgtca ttacggacga 540
gtacaaggtg ccgagcaaaa aattcaaagt tctgggcaat accgatcgcc acagcataaa 600
gaagaacctc attggcgccc tcctgttcga ctccggggag acggccgaag ccacgcggct 660
caaaagaaca gcacggcgca gatatacccg cagaaagaat cggatctgct acctgcagga 720
gatctttagt aatgagatgg ctaaggtgga tgactctttc ttccataggc tggaggagtc 780
ctttttggtg gaggaggata aaaagcacga gcgccaccca atctttggca atatcgtgga 840
cgaggtggcg taccatgaaa agtacccaac catatatcat ctgaggaaga agcttgtaga 900
cagtactgat aaggctgact tgcggttgat ctatctcgcg ctggcgcata tgatcaaatt 960
tcggggacac ttcctcatcg agggggacct gaacccagac aacagcgatg tcgacaaact 1020
ctttatccaa ctggttcaga cttacaatca gcttttcgaa gagaacccga tcaacgcatc 1080
cggagttgac gccaaagcaa tcctgagcgc taggctgtcc aaatcccggc ggctcgaaaa 1140
cctcatcgca cagctccctg gggagaagaa gaacggcctg tttggtaatc ttatcgccct 1200
gtcactcggg ctgaccccca actttaaatc taacttcgac ctggccgaag atgccaagct 1260
tcaactgagc aaagacacct acgatgatga tctcgacaat ctgctggccc agatcggcga 1320
ccagtacgca gacctttttt tggcggcaaa gaacctgtca gacgccattc tgctgagtga 1380
tattctgcga gtgaacacgg agatcaccaa agctccgctg agcgctagta tgatcaagcg 1440
ctatgatgag caccaccaag acttgacttt gctgaaggcc cttgtcagac agcaactgcc 1500
tgagaagtac aaggaaattt tcttcgatca gtctaaaaat ggctacgccg gatacattga 1560
cggcggagca agccaggagg aattttacaa atttattaag cccatcttgg aaaaaatgga 1620

-continued

```
cggcaccgag gagctgctgg taaagcttaa cagagaagat ctgttgcgca aacagcgcac   1680
tttcgacaat ggaagcatcc cccaccagat tcacctgggc gaactgcacg ctatcctcag   1740
gcggcaagag gatttctacc cctttttgaa agataacagg gaaaagattg agaaaatcct   1800
cacatttcgg ataccctact atgtaggccc cctcgcccgg ggaaattcca gattcgcgtg   1860
gatgactcgc aaatcagaag agaccatcac tccctggaac ttcgaggaag tcgtggataa   1920
gggggcctct gcccagtcct tcatcgaaag gatgactaac tttgataaaa atctgcctaa   1980
cgaaaaggtg cttcctaaac actctctgct gtacgagtac ttcacagttt ataacgagct   2040
caccaaggtc aaatacgtca cagaagggat gagaaagcca gcattcctgt ctggagagca   2100
gaagaaagct atcgtggacc tcctcttcaa gacgaaccgg aaagttaccg tgaaacagct   2160
caaagaagac tatttcaaaa agattgaatg tttcgactct gttgaaatca gcggagtgga   2220
ggatcgcttc aacgcatccc tgggaacgta tcacgatctc ctgaaaatca ttaaagacaa   2280
ggacttcctg gacaatgagg agaacgagga cattcttgag gacattgtcc tcacccttac   2340
gttgtttgaa gatagggaga tgattgaaga acgcttgaaa acttacgctc atctcttcga   2400
cgacaaagtc atgaaacagc tcaagaggcg ccgatataca ggatgggggc ggctgtcaag   2460
aaaactgatc aatgggatcc gagacaagca gagtggaaag acaatcctgg attttcttaa   2520
gtccgatgga tttgccaacc ggaacttcat gcagttgatc catgatgact ctctcacctt   2580
taaggaggac atccagaaag cacaagtttc tggccagggg gacagtcttc acgagcacat   2640
cgctaatctt gcaggtagcc cagctatcaa aaagggaata ctgcagaccg ttaaggtcgt   2700
ggatgaactc gtcaaagtaa tgggaaggca taagcccgag aatatcgtta tcgagatggc   2760
ccgagagaac caaactaccc agaagggaca gaagaacagt agggaaagga tgaagaggat   2820
tgaagagggt ataaaagaac tggggtccca aatccttaag gaacacccag ttgaaaacac   2880
ccagcttcag aatgagaagc tctacctgta ctacctgcag aacggcaggg acatgtacgt   2940
ggatcaggaa ctggacatca atcggctctc cgactacgac gtggatcata tcgtgcccca   3000
gtcttttctc aaagatgatt ctattgataa taaagtgttg acaagatccg ataaaaatag   3060
agggaagagt gataacgtcc cctcagaaga agttgtcaag aaaatgaaaa attattggcg   3120
gcagctgctg aacgccaaac tgatcacaca acggaagttc gataatctga ctaaggctga   3180
acgaggtggc ctgtctgagt tggataaagc cggcttcatc aaaaggcagc ttgttgagac   3240
acgccagatc accaagcacg tggcccaaat tctcgattca cgcatgaaca ccaagtacga   3300
tgaaaatgac aaactgattc gagaggtgaa agttattact ctgaagtcta agctggtctc   3360
agatttcaga aaggactttc agttttataa ggtgagagag atcaacaatt accaccatgc   3420
gcatgatgcc tacctgaatg cagtggtagg cactgcactt atcaaaaaat atcccaagct   3480
tgaatctgaa tttgtttacg gagactataa agtgtacgat gttaggaaaa tgatcgcaaa   3540
gtctgagcag gaaataggca aggccaccgc taagtacttc ttttacagca atattatgaa   3600
tttttcaag accgagatta cactggccaa tggagagatt cggaagcgac cacttatcga   3660
aacaaacgga gaaacaggag aaatcgtgtg ggacaagggt agggatttcg cgacagtccg   3720
gaaggtcctg tccatgccgc aggtgaacat cgttaaaaag accgaagtac agaccggagg   3780
cttctccaag gaaagtatcc tcccgaaaag gaacagcgac aagctgatcg cacgcaaaaa   3840
agattgggac cccaagaaat acggcggatt cgattctcct acagtcgctt acagtgtact   3900
ggttgtggcc aaagtggaga aagggaagtc taaaaaactc aaaagcgtca aggaactgct   3960
gggcatcaca atcatggagc gatcaagctt cgaaaaaaac cccatcgact ttctcgaggc   4020
```

```
gaaaggatat aaagaggtca aaaaagacct catcattaag cttcccaagt actctctctt   4080

tgagcttgaa aacggccgga aacgaatgct cgctagtgcg ggcgagctgc agaaaggtaa   4140

cgagctggca ctgccctcta aatacgttaa tttcttgtat ctggccagcc actatgaaaa   4200

gctcaaaggg tctcccgaag ataatgagca gaagcagctg ttcgtggaac aacacaaaca   4260

ctaccttgat gagatcatcg agcaaataag cgaattctcc aaaagagtga tcctcgccga   4320

cgctaacctc gataaggtgc tttctgctta caataagcac agggataagc ccatcaggga   4380

gcaggcagaa aacattatcc acttgtttac tctgaccaac ttgggcgcgc ctgcagcctt   4440

caagtacttc gacaccacca tagacagaaa gcggtacacc tctacaaagg aggtcctgga   4500

cgccacactg attcatcagt caattacggg gctctatgaa acaagaatcg acctctctca   4560

gctcggtgga gacagcaggg ctgaccccaa gaagaagagg aaggtgtgat ctcttctcga   4620

gtcatgtaat tagttatgtc acgcttacat tcacgccctc cccccacatc cgctctaacc   4680

gaaaaggaag gagttagaca acctgaagtc taggtcccta tttatttttt tatagttatg   4740

ttagtattaa gaacgttatt tatatttcaa atttttcttt tttttctgta cagacgcgtg   4800

tacgcatgta acattatact gaaaaccttg cttgagaagg ttttgggacg ctcgaaggct   4860

ttaatttgcc ctctttatat tacatcaaaa taagaaaata attataaca               4909
```